US006194185B1

(12) United States Patent
Croteau et al.

(10) Patent No.: US 6,194,185 B1
(45) Date of Patent: Feb. 27, 2001

(54) RECOMBINANT MATERIALS AND METHODS FOR PRODUCTION OF LIMONENE HYDROXYLASES

(75) Inventors: Rodney Bruce Croteau, Pullman; Shari Lee Lupien, Colfax, both of WA (US); Frank Karp, Moscow, ID (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/292,768

(22) Filed: Apr. 14, 1999

Related U.S. Application Data

(63) Continuation-in-part of application No. 08/881,784, filed on Jun. 24, 1997, now Pat. No. 6,083,731.

(51) Int. Cl.$^7$ .............................. C12N 9/02; C12N 15/53; C12N 15/82

(52) U.S. Cl. ...................... 435/189; 435/252.3; 435/410; 435/320.1; 435/468; 435/476; 536/23.2

(58) Field of Search .............................. 435/320.1, 252.3, 435/189, 410, 468, 476; 536/23.2

(56) References Cited

FOREIGN PATENT DOCUMENTS

93/22441 * 11/1993 (WO) .

OTHER PUBLICATIONS

Alberts et al., *Molecular Biology of the Cell*, Second Ed., Garland Publishing, Inc., New York, NY, pp. 185–187 and 265–266 (1989).

Alonso et al., "Production and Characterization of Polyclonal Antibodies in Rabbits to 4S–Limonene Synthase from Spearmint (*Mentha spicata*)," *Arch. Biochem. Biophys.* 301(1):58–63 (1993).

Alonso et al., "Purification of 4S–Limonene Synthase, a Monoterpene Cyclase from the Glandular Trichomes of Peppermint (*Mentha x piperita*) and Spearmint (*Mentha spicata*)," *J. Biol. Chem.* 267(11):7582–7587 (1992).

Alonso and Croteau, "Comparison of Two Monoterpene Cyclases Isolated From Higher Plants; γ–Terpinene Synthase From *Thymus Vulgaris*, and Limonene Synthase From *Mentha x Piperita*," *Secondary–Metabolite Biosynthesis and Metabolism* (Petrosky and McCormick, eds.), Plenum Press, New York, NY, pp. 239–251 (1992).

Alonso and Croteau, "9. Prenyltransferases and Cyclases," *Methods Plant Biochem.* 9:239–260 (1993).

Ashby et al., in "Prenyltransferases: From Yeast to Man," *Molecular Biology of Atherosclerosis* (Attie, A.D., ed.), Elsevier Science Publishing Co., Inc., Amsterdam, pp. 27–34 (1990).

Bozak et al., "Sequence analysis of ripening–related cytochrome P–450 cDNAs from avocado fruit," *Proc. Natl. Acad. Sci. USA* 87:3904–3908 (1990).

Colby et al., 4S–Limonene Synthase from the Oil Glands of Spearmint (*Mentha spicata*), *J. Biol. Chem.* 268:23016–23024 (1993).

Colby et al., "Isolation and Characterization of cDNA Encoding Limonene Cyclase in Spearmint," *J. Cell Biochem.*, Suppl. 0, 16(F):230 (1992), Abstract Only.

Croteau and Cane, "[44] Monoterpene and Sesquiterpene Cyclases," *Methods of Enzymology* 110:383–405 (1985).

Croteau, "Biosynthesis and Catabolism of Monoterpenoids," *Chem. Rev.* 87:929–954 (1987).

Croteau and Satterwhite, "Biosynthesis of Monoterpenes," *J. Biol. Chem.* 264(26):15309–15315 (1989).

Croteau, "Metabolism of Plant Monoterpenes," *ISI Atlas of Science: Biochemistry*, 1:182–188 (1988).

Croteau and Johnson, "7. Biosynthesis of Terpenoids in Glandular Trichomes," *Biology and Chemistry of Plant Trichomes*, E. Rodriguez et al., Eds., Plenum Publishing Corporation (1984), pp. 133–185.h.

(List continued on next page.)

*Primary Examiner*—Charles L. Patterson, Jr.
(74) *Attorney, Agent, or Firm*—Christensen O'Connor Johnson Kindness PLLC

(57) ABSTRACT cDNA encoding (−)-limonene-6-hydroxylase from spearmint and (−)-limonene-3-hydroxylase from peppermint have been isolated and sequenced, and the corresponding amino acid sequences have been determined. Accordingly, isolated DNA sequences are provided which code for the expression of (−)-limonene-6-hydroxylase from spearmint (SEQ ID No:1, from *Mentha spicata*) and (−)-limonene-3-hydroxylase from peppermint (SEQ ID No:3 and SEQ ID No:5, from *Mentha piperita*). In other aspects, replicable recombinant cloning vehicles are provided which code for limonene hydroxylase or for a base sequence sufficiently complementary to at least a portion of the limonene hydroxylase DNA or RNA to enable hybridization therewith (e.g., antisense limonene hydroxylase RNA or fragments of complementary limonene hydroxylase DNA which are useful as polymerase chain reaction primers or as probes for limonene hydroxylase or related genes). In yet other aspects, modified host cells are provided that have been transformed, transfected, infected and/or injected with a recombinant cloning vehicle and/or DNA sequence encoding limonene hydroxylase. Thus, systems and methods are provided for the recombinant expression of limonene hydroxylase that may be used to facilitate the production, isolation and purification of significant quantities of recombinant limonene hydroxylase (or of the primary enzyme products, trans-carveol or trans-isopiperitenol, respectively) for subsequent use, to obtain expression or enhanced expression of limonene hydroxylase in plants to attain enhanced production of trans-carveol or trans-isopiperitenol as a predator or pathogen defense mechanism, or may be otherwise employed for the regulation or expression of limonene hydroxylase or the production of trans-carveol or trans-isopiperitenol.

16 Claims, 4 Drawing Sheets

OTHER PUBLICATIONS

Croteau and Gershenzon, "Chapter Eight. Genetic Control of Monoterpene Biosynthesis in Mints (Mentha: Lamiaceae)," *Genetic Engineering of Plant Secondary Metabolism*, B.E. Ellis et al., Eds., Plenum Press, New York (1994), pp. 193–229.

Croteau, "The Biosynthesis of Limonene in Mentha Species," In *Progress in Flavour Precursor Studies* (P. Schreier and P. Winterhalter, Eds.), Proceedings of the International Conference, Allured Publishing Corporation, Carol Stream, Illinois, pp 113–122 (1993).

Croteau, "Terpene Metabolism in Mint," *Mint Industry Research Council, Washington Mint Commission, Technical Report Summary Statement*, Jan. 22–24, 1997 (13 pages).

Croteau, "Metabolism of Monoterpenes in Mint (Mentha) Species," *Planta Med.* 57(S1):10–14 (1991).

Facchini and Chappell, "Gene family for an elicitor–induced sesquiterpene cyclase in tobacco," *Proc. Natl. Acad. Sci. USA* 89:11088–11092 (1992).

Gershenzon et al., "Isolation of Secretory Cells from Plant Glandular Trichomes and Their Use in Biosynthetic Studies of Monoterpenes and Other Glaqnd Products," *Anal. Biochem.* 200:130–138 (1992).

Gershenzon et al., "Chapter Ten. Biosynthetic Methods for Plant Natural Products: New Procedures for the Study of Glandular Trichome Constituents," *Modern Phytochemical Methods*, N.H. Fischer et al., Eds., Plenum Press, New York (1991), pp. 347–370.

Gershenzon and Croteau, "Chapter 5. Terpenoids," *Herbivores: Their Interactions with Secondary Plant Metabolites*, vol. I, 2nd Ed. (Rosenthal and Berenbaum, eds.), Academic Press, San Diego, CA, pp. 165–219 (1991).

Gershenzon and Croteau, in "Chapter Three. Regulation of Monoterpene Biosynthesis in Higher Plants," *Biochemistry of the Mevalonic Acid Pathway to Terpenoids* (Towers, G.H.N. and Stafford, H.A., eds.), Plenum Press, New York, NY, Ch. 3, pp. 99–160 (1990).

Harborne, "16 Recent advances in the ecological chemistry of plant terpenoids," *Ecological Chemistry and Biochemistry of Plant Terpenoids* (Harborne and Tomas–Barberan, eds.), Clarendon Press, Oxford, MA, pp. 399–426 (1991).

Hallahan and Croteau, "Monoterpene Biosynthesis: Mechanism and Stereochemistry of the Enzymatic Cyclization of Geranyl Pyrophosphate to (+)–cis–and (+)–trans–Sabinene Hydrate," *Arch. Biochem. Biophys.* 269(1):313–326 (1989).

Karp and Croteau, "Role of Hyrdoxylases in Monoterpene Biosynthesis," *Bioflavour '87*, Walter de Gruyter & Co., Berlin (1988), pp. 173–198.

Karp et al., "Monoterpene Biosynthesis: Specificity of the Hydroxylations of (3l )–Limonene by Enzyme Preparations from Peppermint (*Mentha piperita*), Spearmint (*Mentha spicata*), and Perilla (*Perilla frutescens*) Leaves," *Arch. Biochem. Biophys.* 276:219–226 (1990).

Karp and Croteau, "Hydroxylation of (−)–β–Pinene and (−)–β–Pinene by a Cytochrome P–450 System from Hyssop (*Hyssopus Officinalis*)," *Secondary–Metabolite Biosynthesis and Metabolism*, R.J. Petroski et al., Eds., Plenum Press, New York (1992), pp. 253–260.

Kjonaas and Croteau, "Demonstration that Limonene is the First Cyclic Intermediate in Biosynthesis of Oxygenated p–Menthane Monoterpenes in *Mentha piperita* and Other Metha Species," *Arch. Biochem. Biophys.* 220(1):79–89 (1983).

Lanznaster and Croteau, "Dye–Ligand and Immobilized Metal Ion Interaction Chromatography for the Purification of Enzymes of Prenyl Pyrophosphate Metabolism," *Protein Express. Purif.* 2:69–74 (1991).

Lupien et al., "Cytochrome P450 Limonene Hydroxylases of Mentha Species," *Drug Metabolism and Drug Interactions*, N. Kingsley, Ed., Freund Publishing House, London, England (1995), pp. 245–260.

Math et al., "The crtE gene in *Erwinia herbicola* encodes geranylgeranyl diphosphate synthase," *Proc. Natl. Acad. Sci. USA* 89:6761–6764 (1992).

McGarvey and Croteau, "Overexpression and mutagenesis of 4S–limonene synthase from spearmint (*Mentha spicata*)," *Plant Physiology* 105(1):89 (1994), Abstract Only.

Mihaliak et al., "10. Cytochrome P–450 Terpene Hydroxylases," *Meth. Plant Biochem.* 9:261–279 (1993).

Ponnamperuma and Croteau, "Purification and Characterization of an NADPH–Cytochrome P450 (Cytochrome c) Reductase from Spearmint (*Mentha spicata*) Glandular Trichomes," *Arch. Biochem. Biophys.* 329(1):9–16 (1996).

Rajaonarivony et al., "Evidence for an Essential Histidine Residue in 4S–Limonene Synthase and Other Terpene Cyclases," *Arch. Biochem. Biophys.* 299(1):77–82 (1992).

Rajaonarivony et al., "Characterization and Mechanism of (4S)–Limonene Synthase, a Monoterpene Cyclase from the Glandular Trichomes of Peppermint (*Mentha x piperita*)," *Arch. Biochem. Biophys.* 296(1):49–57 (1992).

Satterwhite and Croteau, "Resolution of Monoterpene Enantiomers by Gas Chromatography," *J. Chromatogr.* 407:243–252 (1987).

Satterwhite and Croteau, "Applications of Gas Chromatography to the Study of Terpenoid Metabolism," *J. Chromatography* 452:61–73, Elsevier Science Publishers B.V., Amsterdam (1988).

Savage et al., "Monoterpene Synthases of *Pinus contorta* and Related Conifers," *J. Biol. Chem.* 269(6):4012–4020 (1994).

Kang et al., "Isolation of a Genomic Clone for Cytochrome P450 Oxidase from *Mentha piperita*," *Mol. Cells.* 3(3):283–288 (1993).

\* cited by examiner

|  | | C-3 hydroxylase | C-6 hydroxylase |
|---|---|---|---|
| (+)-Limonene | Products: | (+)-*trans*-isopiperitenol (50%) | (+)-*cis*-carveol (25%) |
| (−)-*p*-Menth-1-ene | Products: | (−)-*trans*-isopiperitol (37%) | (−)-*trans*-carvotanacetol (74%) |
| (+)-*p*-Menth-1-ene | Products: | (+)-*trans*-piperitol (37%) | (+)-*cis*-carvotanacetol (30%)<br><br>(+)-*trans*-piperitol (31%) |

RECOMBINANT MATERIALS AND METHODS FOR PRODUCTION OF LIMONENE HYDROXYLASES

The present application is a continuation-in-part of U.S. application Ser. No. 08/881,784, filed Jun. 24, 1997 now U.S. Pat. No. 6,083,731.

This invention was supported in part by grant number MCB 96-04918 awarded by the National Science Foundation. The government has certain rights in the invention.

FIELD OF THE INVENTION

The present invention relates to nucleic acid sequences which code for cytochrome P450 limonene hydroxylases, such as (−)-limonene-6-hydroxylase from *Mentha spicata* and (−)-limonene-3-hydroxylase from *Mentha piperita*, and to vectors containing the sequences, host cells containing the sequences and methods of producing recombinant limonene hydroxylases and their mutants.

BACKGROUND OF THE INVENTION

Several hundred naturally occurring, monoterpenes are known, and essentially all are biosynthesized from geranyl pyrophosphate, the ubiquitous $C_{10}$ intermediate of the isoprenoid pathway (Croteau and Cane, *Methods of Enzymology* 110:383–405 [1985]; Croteau, *Chem. Rev.* 87:929–954 [1987]). Monoterpene synthases, often referred to as "cyclases," catalyze the reactions by which geranyl pyrophosphate is cyclized to the various monoterpene carbon skeletons. Many of the resulting carbon skeletons undergo subsequent oxygenation by cytochrome P450 hydroxylases to give rise to large families of derivatives. Research on biosynthesis has been stimulated by the commercial significance of the essential oils (Guenther, *The Essential Oils*, Vols. III–VI (reprinted) R. E. Krieger, Huntington, N.Y. [1972]) and aromatic resins (Zinkel and Russell, *Naval Stores: Production, Chemistry, Utilization*, Pulp Chemicals Association, New York [1989]) and by the ecological roles of these terpenoid secretions, especially in plant defense (Gershenzon and Croteau, in "Herbivores: Their Interactions with Secondary Plant Metabolites," Vol. I, 2nd Ed. (Rosenthal and Berenbaum, eds.) Academic Press, San Diego, Calif., pp. 165–219 [1991]; Harborne, in "Ecological Chemistry and Biochemistry of Plant Terpenoids," (Harborne and Tomas-Barberan eds.) Clarendon Press, Oxford, Mass., pp. 399–426 [1991]).

The reactions catalyzed by the cytochrome P450-(−)-limonene hydroxylases determine the oxidation pattern of the monoterpenes derived from limonene (see FIGS. 1A–1C). These reactions are completely regiospecific and are highly selective for (−)-limonene as substrate. The primary products of limonene hydroxylation (trans-carveol and trans-isopiperitenol) are important essential oil components and serve as precursors of numerous other monoterpenes of flavor or aroma significance (see FIGS. 1A–1C).

One of the major classes of plant monoterpenes is the monocyclic p-menthane (1-methyl-4-isopropylcyclohexane) type, found in abundance in members of the mint (Mentha) family. The biosynthesis of p-menthane monoterpenes in Mentha species, including the characteristic components of the essential oil of peppermint (i.e., (−)-menthol) and the essential oil of spearmint (i.e., (−)-carvone), proceeds from geranyl pyrophosphate via the cyclic olefin (−)-limonene and is followed by a series of enzymatic redox reactions that are initiated by cytochrome P450 limonene hydroxylases (e.g., limonene-3-hydroxylase in peppermint and limonene-6-hydroxylase in spearmint and related species; Karp et al., *Arch. Biochem. Biophys.* 276:219–226 [1990]; Gershenzon et al., *Rec. Adv. Phytochem.* 28:193–229 [1994]; Lupien et al., *Drug Metab. Drug Interact.* 12:245–260 [1995]). The products of limonene hydroxylation and their subsequent metabolites (as shown in FIGS. 1A–1C) also serve ecological roles in plant defense mechanisms against herbivores and pathogens, and may act as signals in other plant-insect relationships (e.g., as attractants for pollinators and seed dispersers).

A detailed understanding of the control of monoterpene biosynthesis and of the reaction mechanisms, enzymes and the relevant cDNA clones as tools for evaluating patterns of developmental and environmental regulation, for examining active site structure-function relationships and for the generation of transgenic organisms bearing such genes are disclosed in part in parent U.S. related application Ser. No. 08/582,802 filed Jan. 4, 1996 as a continuation of application Ser. No. 08/145,941 filed Oct. 28, 1993, the disclosures of which are incorporated herein by this reference, which disclose the isolation and sequencing of cDNAs encoding (−)4S-limonene synthase, the enzyme responsible for cyclizing geranyl pyrophosphate to obtain (−)-limonene. To date, however, no information has been available in the art regarding the protein and nucleotide sequences relating to the enzymes through which (−)-limonene is hydroxylated (by the action of (−)-limonene-6-hydroxylase to form trans-carveol or by the action of (−)-limonene-3-hydroxylase to form trans-isopiperitenol as shown in FIG. 1).

SUMMARY OF THE INVENTION

In accordance with the foregoing, cDNAs encoding (−)-limonene hydroxylase, particularly (−)-limonene-6-hydroxylase from spearmint and (−)-limonene-3-hydroxylase from peppermint, have been isolated and sequenced, and the corresponding amino acid sequences have been deduced. Accordingly, the present invention relates to isolated nucleic acid sequences which code for the expression of limonene hydroxylase, such as the sequence designated SEQ ID No:1 which encodes (−)-limonene-6-hydroxylase (SEQ ID No:2) from spearmint (*Mentha spicata*), or the sequence designated SEQ ID No:3 which encodes (−)-limonene-3-hydroxylase (SEQ ID No:4) from peppermint (*Mentha piperita*), or the sequence designated SEQ ID No:5 which encodes another (−)-limonene-3-hydroxylase (SEQ ID No:6) from peppermint (*Mentha piperita*). In other aspects, the present invention is directed to replicable recombinant cloning vehicles comprising a nucleic acid sequence, e.g., a DNA sequence, which codes for limonene hydroxylases or for a base sequence sufficiently complementary to at least a portion of the limonene hydroxylase DNA or RNA to enable hybridization therewith (e.g., antisense limonene hydroxylase RNA or fragments of complementary limonene hydroxylase DNA which are useful as polymerase chain reaction primers or as probes for limonene hydroxylases or related genes). In yet other aspects of the invention, modified host cells are provided that have been transformed, transfected, infected and/or injected with a recombinant cloning vehicle and/or DNA sequence of the invention. Thus, the present invention provides for the recombinant expression of limonene hydroxylases, and the inventive concepts may be used to facilitate the production, isolation and purification of significant quantities of recombinant limonene hydroxylase (or of the primary enzyme products, trans-carveol in the case of (−)-limonene-6-hydroxylase or trans-isopiperitenol in the case of (−)-limonene-3-hydroxylase) for subsequent use, to obtain expression, or enhanced expression, or altered expression, of limonene hydroxylase in plants to attain enhanced trans-carveol or trans-isopiperitenol production as a predator or pathogen defense mechanism, attractant or environmental signal, or may be otherwise employed in an environment where the regulation or expression of limonene hydroxylase is desired for the production of limonene hydroxylase or the enzyme products, trans-carveol or trans-isopiperitenol, or their derivatives.

In another aspect, the present invention is directed to isolated nucleic acid molecules that hybridize under stringent hybridization conditions to a fragment (having a length of at least 15 bases) of any one of the nucleic acid molecules of the present invention encoding a limonene-3-hydroxylase or limonene-6-hydroxylase.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

As shown in FIG. 1A, after geranyl pyrophosphate is cyclized to limonene, the limonene is acted on by (−)-limonene-6-hydroxylase (L6-OH in FIG. 1A) to form trans-carveol or by (−)-limonene-3-hydroxylase (L3-OH in FIG. 1A) to form trans-isopiperitenol. Subsequently, as shown in FIGS. 1B and 1C, a series of secondary redox transformations convert these olefinic intermediates to other monoterpenes; and FIG. 2 shows the monoterpene olefins, in addition to (−)-limonene, (i.e., (+)-limonene, (−)-p-menth-1-ene, and (+)-p-menth-1-ene) shown to be limonene-6-hydroxylase and limonene-3-hydroxylase substrates, and the percentage conversion to products as compared to the conversion of (−)-limonene at saturation.

DETAILED DESCRIPTION OF THE PREFERRED EMBODIMENT

Figure 1A:
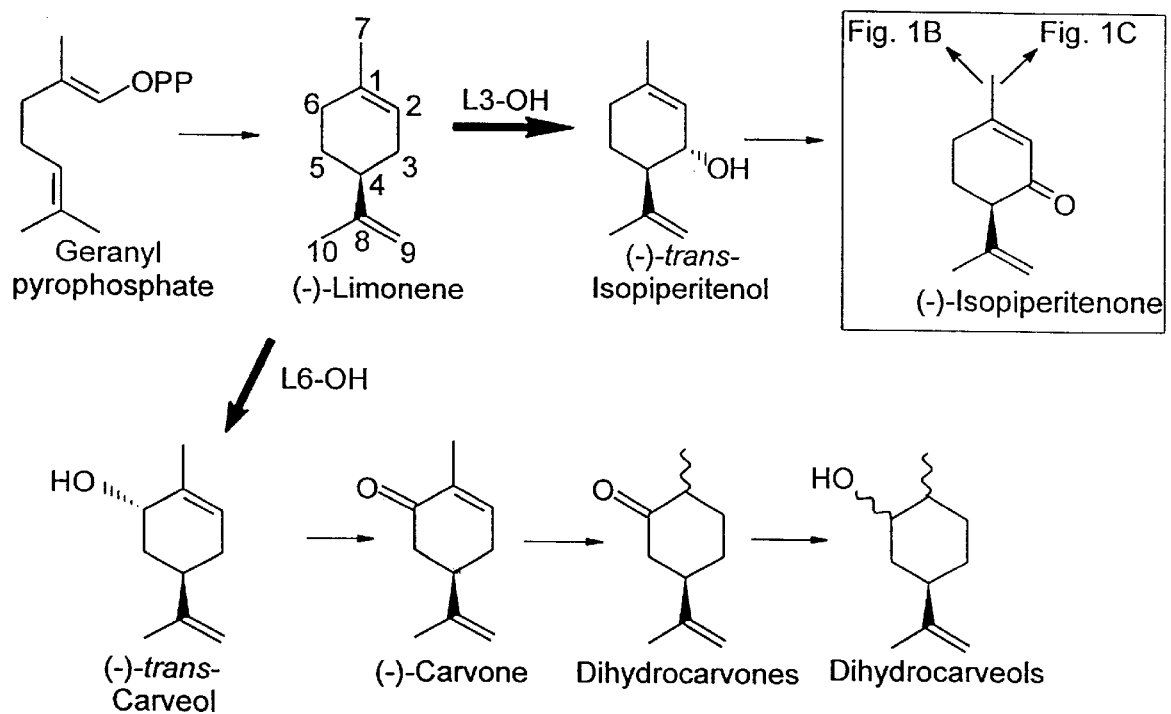
FIGS. 1A–1C are schematic representations of the principal pathways of monoterpene biosynthesis in spearmint leading to carvone and in peppermint leading to menthol.
Figure 1B:
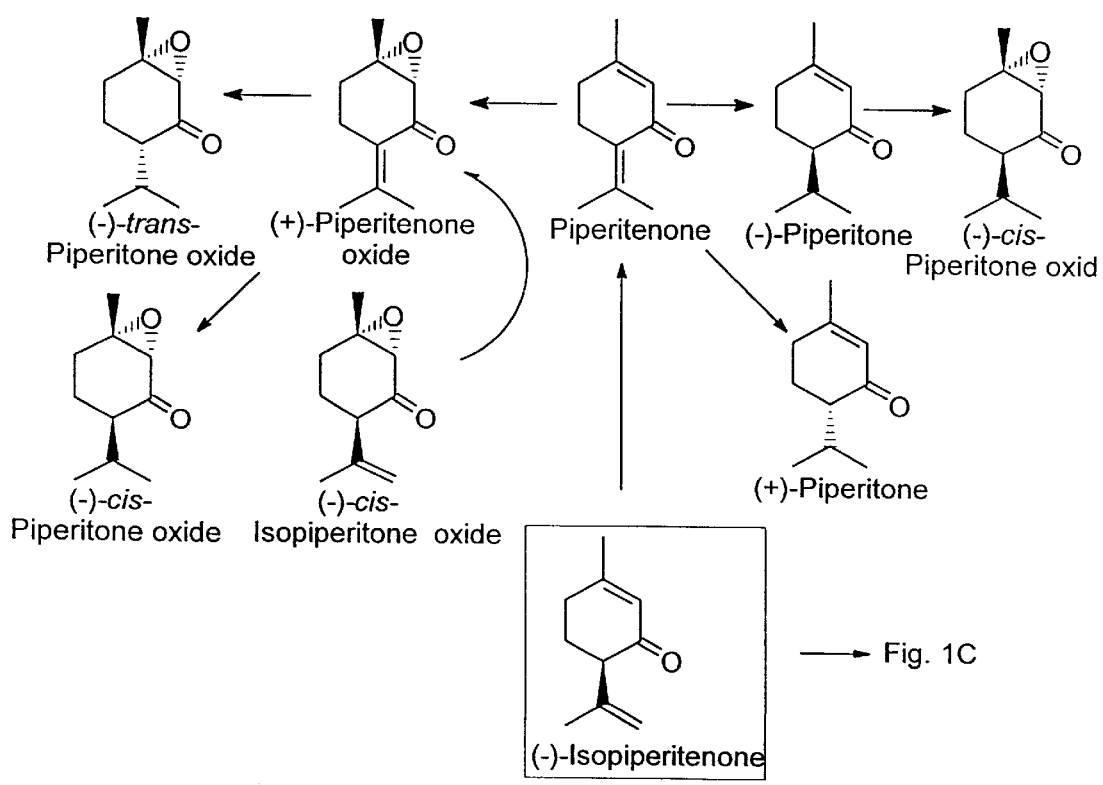
Figure 1C:
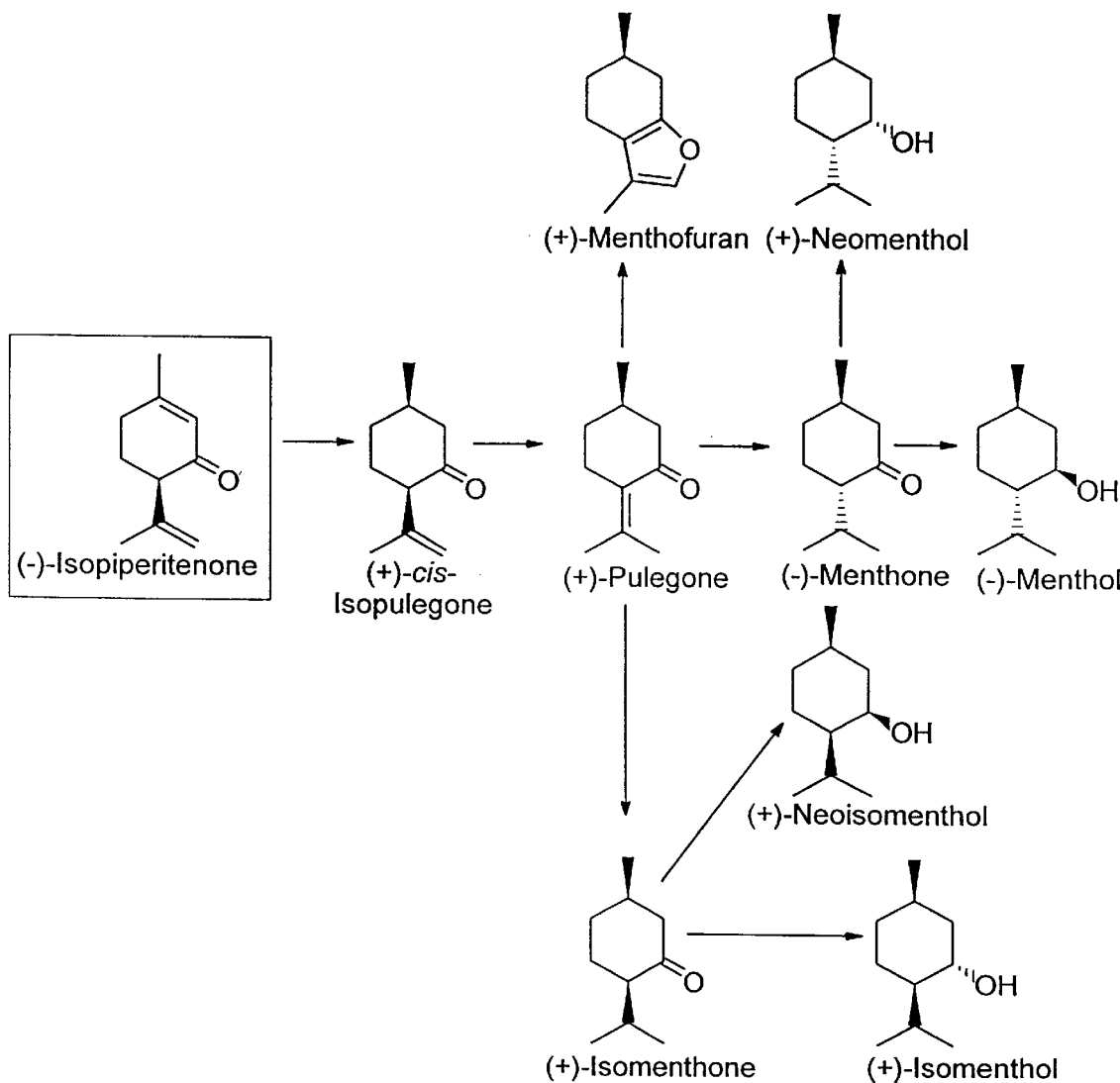

As used herein, the terms "amino acid" and "amino acids" refer to all naturally occurring L-α-amino acids or their residues. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nueleoside. The base characterizes the nucleotide with the four bases of DNA being adenine ("A"), guanine ("G"), cytosine ("C"), thymine ("T") and inosine ("I"). The four RNA bases are A,G,C and uracil ("U"). The nucleotide sequences described herein comprise a line array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified on polyacrylamide gels.

The term "limonene hydroxylase" is used herein to mean an enzyme capable of catalyzing the hydroxylation of limonene to its hydroxylated products, such as trans-carveol in the case of (−)-limonene-6-hydroxylase or trans-isopiperitenol in the case of (−)-limonene-3-hydroxylase, as described herein.

The terms "alteration", "amino acid sequence alteration", "variant" and "amino acid sequence variant" refer to limonene hydroxylase molecules with some differences in their amino acid sequences as compared to native limonene hydroxylase. Ordinarily, the variants will possess at least about 70% homology with native limonene hydroxylase, and preferably, they will be at least about 80% homologous with native limonene hydroxylase. The amino acid sequence variants of limonene hydroxylase falling within this invention possess substitutions, deletions, and/or insertions at certain positions. Sequence variants of limonene hydroxylase may be used to attain desired enhanced or reduced enzymatic activity, modified regiochemistry or stereochemistry, or altered substrate utilization or product distribution such as enhanced production of other products obtained from alternative substrates, such as those shown in FIG. 2.

Substitutional limonene hydroxylase variants are those that have at least one amino acid residue in the native limonene hydroxylase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the limonene hydroxylase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the limonene hydroxylase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional limonene hydroxylase variants are those with one or more amino acids inserted immediately adjacent to an amino acid at a particular position in the native limonene hydroxylase molecule. Immediately adjacent to an amino acid means connected to either the (α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native limonene hydroxylase molecule have been removed. Ordinarily, deletional variants will have one or two amino acids deleted in a particular region of the limonene hydroxylase molecule.

The terms "biological activity", "biologically active", "activity" and "active" refer to the ability of the limonene hydroxylase molecule to convert (−)-limonene to carveol and isopiperitenol and co-products as measured in an enzyme activity assay, such as the assay described in Example 7 below. Amino acid sequence variants of limonene hydroxylase may have desirable altered biological activity including, for example, altered reaction kinetics, substrate utilization product distribution or other characteristics such as regiochemistry and stereochemistry.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The term "essential oil plant," or "essential oil plants," refers to a group of plant species that produce high levels of monoterpenoid and/or sesquiterpenoid and/or diterpenoid oils, and/or high levels of monoterpenoid and/or sesquiterpenoid and/or diterpenoid resins. The foregoing oils and/or resins account for greater than about 0.005% of the fresh weight of an essential oil plant that produces them. The essential oils and/or resins are more fully described, for example, in E. Guenther, *The Essential Oils*, Vols. I–VI, R. E. Krieger Publishing Co., Huntington N.Y, 1975, incorporated herein by reference. The essential oil plants include, but are not limited to:

Lamiaceae, including, but not limited to, the following species: Ocimum (basil), Lavandula (Lavender), Origanum (oregano), Mentha (mint), Salvia (sage), Rosmecinus (rosemary), Thymus (thyme), Satureja and Monarda.

Umbelliferae, including, but not limited to, the following species: Carum (caraway), Anethum (dill), feniculum (fennel) and Daucus (carrot).

Asteraceae (Compositae), including, but not limited to, the following species: Artemisia (tarragon, sage brush), Tanacetum (tansy).

Rutaceae (e.g., citrus plants); Rosaceae (e.g., roses); Myrtaceae (e.g., eucalyptus, Melaleuca); the Gramineae (e.g. Cymbopogon (citronella)); Geranaceae (Geranium) and certain conifers including Abies (e.g., Canadian balsam), Cedrus (cedar) and Thuja and Juniperus.

The range of essential oil plants is more fully set forth in E. Guenther, *The Essential Oils*, Vols. I–VI, R. E. Krieger Publishing Co., Huntington N.Y, 1975, which is incorporated herein by reference.

The term "percent identity" means the percentage of amino acids or nucleotides that occupy the same relative position when two amino acid sequences, or two nucleic acid sequences, are aligned side by side.

The term "percent similarity" is a statistical measure of the degree of relatedness of two compared protein sequences. The percent similarity is calculated by the GAP program from GCG Version 9.0 (1996) which utilizes the algorithm of Needleman S. B. and Wunsch C. D., *J. Mol. Biol.* 48: 443–453 (1970), incorporated herein by reference.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell" and "transformed" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA.

In accordance with the present invention, cDNA encoding limonene hydroxylase was isolated and sequenced in the following manner. (−)-Limonene hydroxylase is located exclusively in the glandular trichome secretory cells and catalyzes the hydroxylation of (−)-limonene in these essential oil species. Known methods for selectively isolating secretory cell clusters from these epidermal oil glands and for extracting these structures were employed to obtain sufficient amounts of light membranes (microsomes). The light membranes were solubilized and the resulting protein subjected to hydrophobic interaction chromatography which served to purify a spectrally characterized (Omura et al., *J. Biol. Chem.* 239:2379–2385 [1964]) cytochrome P450 enzyme from spearmint secretory glands. This approach, however, does not differentiate between enzymatically distinct cytochrome P450 species. Amino acid sequence information derived from the purified protein was employed in a molecular approach to the isolation of gland specific cDNA clones encoding such cytochromes. Following isolation and sequencing of the cytochrome P450 cDNA (SEQ ID No:1) from spearmint, functional expression was required to confirm the catalytic identity of the enzyme encoded. A Spodoptera-Baculovirus expression system, combined with the in situ bioassay (feeding (−)-limonene substrate during recombinant protein expression), successfully confirmed that the target clone (limonene-6-hydroxylase) had been isolated. Sequence information from the full length spearmint limonene hydroxylase cDNA (SEQ ID No:1) was utilized to construct a selective probe for the isolation of the related (−)-limonene-3-hydroxylase gene (SEQ ID No:3) from peppermint secretory glands. Functional expression in the Spodoptera-Baculovirus expression system, by in situ bioassay, also confirmed the peppermint limonene-3-hydroxylase clone (SEQ ID No:3), which was fully sequenced. Sequence comparison showed the two regiospecific hydroxylases from spearmint and peppermint to be very similar, as expected, since spearmint (*M. spicata*) is a tetraploid and parent of peppermint (*M. piperita=Mentha aquatica×spicata*), a hexaploid (Harley and Brighton, *Bot. J. Linn. Soc.* 74:71–96 [1977]). In vitro studies confirmed the recombinant enzymes to resemble their native counterparts. An additional limonene-3-hydroxylase cDNA clone (SEQ ID No:5) was isolated from a peppermint cDNA library.

The isolation of the limonene hydroxylase cDNAs (SEQ ID No:1; SEQ ID No:3; SEQ ID No:5) permits the development of an efficient expression system for these functional enzymes with which detailed mechanistic structural studies can be undertaken. The limonene hydroxylase cDNAs (SEQ ID No:1; SEQ ID No:3; SEQ ID No:5) also provide useful tools for isolating other monoterpene hydroxylase genes and for examining the developmental regulation of monoterpene biosynthesis.

Although the limonene hydroxylase cDNA set forth in SEQ ID No:1 directs the enzyme to plastids, substitution of the targeting sequence (SEQ ID No:1, nucleotides 20 to 146) with other transport sequences well known in the art (see, e.g., Keegstra et al., supra; von Heijne et al., supra) may be employed to direct the limonene hydroxylase to other cellular or extracellular locations.

In addition to the native (−)-limonene-6-hydroxylase amino acid sequence of SEQ ID No:2, encoded by the DNA sequence of SEQ ID No:1, and the native (−)-limonene-3-hydroxylase amino acid sequences of SEQ ID No:4 and SEQ ID No:6, encoded by the DNA sequences set forth in SEQ ID No:3 and SEQ ID No:5, respectively, sequence variants produced by deletions, substitutions, mutations and/or insertions are intended to be within the scope of the invention except insofar as limited by the prior art. The limonene hydroxylase amino acid sequence variants of this invention may be constructed by mutating the DNA sequence that encodes wild-type limonene hydroxylase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

In the case of the hydrophobic cleft of the hydroxylases, a number of residues may be mutagenized in this region. Directed mutagenesis can also be used to create cassettes for saturation mutagenesis. Once a hydrophobic segment of the active site is identified, oligonucleotide-directed mutagenesis can be used to create unique restriction sites flanking that region to allow for the removal of the cassette and the subsequent replacement with synthetic cassettes containing any number of mutations within. This approach can be carried out with any plasmid, without need for subcloning or generation of single-stranded phagemids.

The verified mutant duplexes in the pET (or other) overexpression vector can be employed to transform *E. coli* such as strain *E. coli* BL21(DE3)pLysS, for high level production of the mutant protein, and purification by metal ion affinity chromatography and thrombin proteolysis. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native cyclase. If the residue is by this means demonstrated to be important by activity impairment, or knockout, then conservative substitutions can be made, such as Asp for Glu to alter side chain length, Ser for Cys, or Arg for His. For hydrophobic segments, it is largely size that we will alter, although aromatics can also be substituted for alkyl side chains. Changes in the normal product distribution can indicate which step(s) of the reaction sequence have been altered by the mutation. Modification of the hydrophobic pocket can be employed to change binding conformations for substrates and result in altered regiochemistry and/or stereochemistry.

Other site directed mutagenesis techniques may also be employed with the nucleotide sequences of the invention. For example, restriction endonuclease digestion of DNA followed by ligation may be used to generate limonene hydroxylase deletion variants, as described in section 15.3 of Sambrook et al. (*Molecular Cloning: A Laboratory Manual*, 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]). Generally, oligonucleotides of at least 25 nucleotides in length are used to insert, delete or substitute two or more nucleotides in the limonene hydroxylase molecule. An optimal oligonucleotide will have 12 to 15 perfectly matched nucleotides on either side of the nucleotides coding for the mutation. To mutagenize the wild-type limonene hydroxylase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type limonene hydroxylase inserted in the vector, and the second strand of DNA encodes the mutated form of limonene hydroxylase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type limonene hydroxylase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

The genes encoding the (−)-limonene hydroxylase enzymes may be incorporated into any organism (intact plant, animal, microbe or cell culture, etc.) that produces limonene (either as a native property or via transgenic manipulation of one or more of the enzymes involved in limonene synthesis, such as limonene synthase) to affect the conversion of limonene to carveol or isopiperitenol (and their subsequent metabolites, depending on the organism) to produce or modify flavor and aroma properties, to improve defense capability, or to alter other ecological interactions mediated by these metabolites or for the production of the metabolites themselves. The expressed hydroxylases may also be used outside of living cells as a reagent to catalyze the corresponding oxidations of limonene in vitro. Since (+)-limonene also serves as a substrate for these hydroxylases (albeit less efficiently, see FIG. 2), the methods and recombinant enzymes of the present invention are useful for the production of all stereoisomeric products derived by either C3- or C6-hydroxlyation of (+)- or (−)-limonene or related compounds.

Eukaryotic expression systems are commonly employed for cytochrome P450 expression since they carry out any required posttranslational modifications, direct the enzyme to the proper membrane location, and possess a compatible reductase to deliver electrons to the cytochrome. A representative eucaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Biotechnology* 6:47–55 [1987]) for expression of the limonene hydroxylases of the invention. Infection of insect cells (such as cells of the species *Spodoptera frugiperda*) with the recombinant baculoviruses allows for the production of large amounts of the limonene hydroxylase protein. In addition, the baculovirus system has other important advantages for the production of recombinant limonene hydroxylase. For example, baculoviruses do not infect humans and can therefore be safely handled in large quantities. In the baculovirus system, a DNA construct is prepared including a DNA segment encoding limonene hydroxylase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/limonene hydroxylase combination is flanked on both sides by 200–300 base pairs of baculovirus DNA (the flanking sequences).

To produce the limonene hydroxylase DNA construct, a cDNA clone encoding the full length limonene hydroxylase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full limonene hydroxylase. For example, an insect host cell can be cotransfected or transfected separately with the DNA construct and a functional baculovirus. Resulting recombinant baculoviruses can then be isolated and used to infect cells to effect production of the limonene hydroxylase. Host insect cells include, for example, *Spodoptera fru-* giperda cells, that are capable of producing a baculovirus-expressed limonene hydroxylase. Insect host cells infected with a recombinant baculovirus of the present invention are then cultured under conditions allowing expression of the baculovirus-encoded limonene hydroxylase. Limonene hydroxylase thus produced is then extracted from the cells using methods known in the art. For a detailed description of the use of the baculovirus/Spodoptera expression system, see Examples 5 and 6, infra.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature* 282:39 [1979]; Kingsman et al., *Gene* 7:141 [1979]; Tschemper et al., *Gene* 10:157 [1980]) is commonly used as an expression vector in Saccharomyces. This plasmid contains the trp1 gene that provides a selection marker for a mutant strain of yeast lacking the ability to grow in tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978]).

Suitable promoting sequences in yeast vectors include the promoters for 3-phosphoglycerate kinase (Hitzeman et al., *J. Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase glucose-6-phosphate isomerase, 3-phosphoglycerate mutase, pyruvate kinase, triose-phosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms and multicellular organisms, such as plants, may be used as hosts to practice this invention. For example, transgenic plants can be obtained such as by transferring plasmids that encode limonene hydroxylase and a selectable marker gene, e.g., the kan gene encoding resistance to kanamycin, into Agrobacterium tumifaciens containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through Agrobacterium tumifaciens, as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al., *EMBO J.* 1:841 [1982]), and direct microinjection into nuclei (Capecchi, *Cell* 22:479 [1980]) may also be used. Transformed plant calli may be selected through the selectable marker by growing the cells on a medium containing e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating limonene hydroxylase production can be incorporated into the plant along with a necessary promoter which is inducible. In the practice of this embodiment of the invention, a promoter that only responds to a specific external or internal stimulus is fused to the target cDNA. Thus the gene will not be transcribed except in response to the specific stimulus. As long as the gene is not being transcribed, its gene product is not produced (nor is the corresponding hydroxylation product of limonene).

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a limonene hydroxylase gene that previously has had its native promoter removed. This engineered gene is the combination of a promoter that responds to an external chemical stimulus and a gene responsible for successful production of limonene hydroxylase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology*, CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science,* 240(4849):204–207 [1988]); treatment of protoplasts with polyethylene glycol (Lyznik et al., *Plant Molecular Biology,* 13:151–161 [1989]); and bombardment of cells with DNA-laden microprojectiles which are propelled by explosive force or compressed gas to penetrate the cell wall (Klein et al., *Plant Physiol.* 91:440–444 [1989] and Boynton et al., *Science,* 240(4858):1534–1538 [1988]). Transformation of gymnosperm species can be achieved, for example, by employing the methods set forth in Han et al, *Plant Science,* 95:187–196 (1994), incorporated by reference herein. A method that has been applied to Rye plants (*Secale cereale*) is to directly inject plasmid DNA, including a selectable marker gene, into developing floral tillers (de la Pena et al., Nature 325:274–276 (1987)). Further, plant viruses can be used as vectors to transfer genes to plant cells. Examples of plant viruses that can be used as vectors to transform plants include the Cauliflower Mosaic Virus (Brisson et al., *Nature* 310: 511–514 (1984)). Additionally, plant transformation strategies and techniques are reviewed in Birch, R. G., *Ann Rev Plant Phys Plant Mol Biol,* 48:297 (1997); Forester et al., *Exp. Agric.,* 33:15–33 (1997). The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Another screenable gene is a transcriptional activator for anthocyanin biosynthesis, as described in the copending application of Bowen et al., U.S. patent application Ser. No. 387,739, filed Aug. 1, 1989. This gene causes the synthesis of the pigment anthocyanin. Cells transformed with a plasmid containing this gene turn red. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Mather et al., *Annals N.Y. Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

Satisfactory amounts of limonene hydroxylase are produced by transformed cell cultures. However, the use of a secondary DNA coding sequence can enhance production levels. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coil* K12 strain 294 (ATCC No. 31,446), *E. coli* strain W3110 (ATCC No. 27,325) *E. Coli* X1776 (ATCC No. 31,537), and *E coli* B; however many other strains of *E. coli*, such as HB0101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells.

As a representative example, cDNA sequences encoding limonene hydroxylase may be transferred to the $(His)_6$. Tag pET vector commercially available (from Novagen) for overexpression in *E Coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein within thrombin, and the limonene hydroxylase again purified by immobilized metal ion affinity chromatography, this time using a shallower imidazole gradient to elute the recombinant hydroxylase while leaving the histidine block still adsorbed. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

As described above, the limonene-6-hydroxylase amino terminal membrane insertion sequence resides at SEQ ID No:2, residues 1 through 42, and in the embodiment shown in SEQ ID No:2 directs the enzyme to endoplasmic reticulum membranes. Alternative trafficking sequences from plants, animals and microbes can be employed in the practice of the invention to direct the gene product to the cytoplasm, plastids, mitochondria or other cellular components, or to target the protein for export to the medium. These considerations apply to the overexpression of (−)-limonene-6-hydroxylase or (−)-limonene-3-hydroxylase, and to direction of expression within cells or intact organisms to permit gene product function in any desired location.

The construction of suitable vectors containing DNA encoding replication sequences, regulatory sequences, phenotypic selection genes and the limonene hydroxylase DNA of interest are prepared using standard recombinant DNA procedures. Isolated plasmids and DNA fragments are cleaved, tailored, and ligated together in a specific order to generate the desired vectors, as is well known in the art (see, for example, Maniatis, supra, and Sambrook et al., supra).

As discussed above, limonene hydroxylase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 [1982]), and Goeddel et al. (*Nucleic Acids Res.*, supra).

The following examples merely illustrate the best mode now contemplated for practicing the invention, but should not be construed to limit the invention. All literature citations herein are expressly incorporated by reference.

EXAMPLES

Example 1

Plant Material and Limonene-6-Hydroxylase Isolation

Plant materials—Spearmint (*Mentha spicata*) plants were propagated from rhizomes or stem cuttings in peat moss:pumice:sand (58:35:10, v/v/v) and were grown in a greenhouse with supplemental lighting (16 h, 21,000 lux minimum) and a 30°/15° C. (day/night) temperature cycle. Plants were watered as needed and fertilized daily with a complete fertilizer (N:P:K, 20:20:20) plus iron chelate and micronutrients. Apical buds of vegetative stems (3–7 weeks old) were used for the preparation of glandular trichome cells for enzyme extraction and for nucleic acid isolation. (−)-4S-Limonene (97%) and other monoterpene standards were part of the lab collection or were purchased from Sigma or Aldrich and were purified by standard chromatographic methods.

Limonene-6-hydroxylase isolation—Limonene-6-hydroxylase was extracted from a purified preparation of glandular trichome secretory cell clusters isolated from spearmint (*Mentha spicata*). To obtain these clusters, plant material was soaked in ice-cold, distilled water for 1 h and gently abraded in a cell disrupter of our own design (Colby et al., *J. Biol. Chem.* 268:23016–23024 [1993]). Batches of 45–60 g of spearmint apical tissue were abraded in the 600 ml polycarbonate cell disruption chamber with 140 ml of glass beads (500 $\mu$m diameter, Bio-Spec Products), 35 g Amberlite XAD-4 resin and ~300 ml of extraction buffer consisting of (25 mM MOPSO, 0.5 mM sodium phosphate (pH 7.4), 200 mM sorbitol, 10 mM sucrose. 10 mM sodium-metabisulfite, 10 mM ascorbate, 1% (w/v) polyvinylpyrrolidone ($M_r$ 40,000), 0.6% methyl cellulose, and 1 mM DTT). Removal of glandular trichome secretory cells was accomplished by three 1 min pulses of operation with the rotor speed controlled by a rheostat set at 85–95 V. This procedure was carried out at 4° C., and after each pulse the chamber was allowed to cool for 1 min. The isolated secretory cell clusters were separated from the glass beads, XAD-4 resin and residual plant material by sieving through a series of nylon meshes. The secretory cell clusters (approximately 60 $\mu$m in diameter) readily passed through meshes of 350 and 105 $\mu$m and were collected on a mesh of 20 $\mu$m. After filtration, cell clusters were washed to remove chloroplasts and other contaminates, and suspended in 50 ml of cell disruption (sonication) buffer (100 mM sodium phosphate (pH 7.4), 250 mM sucrose, 1 mM DTT, 1 mM PMSF, 1 mM sodium EDTA, and 5 $\mu$M flavins (FAD and FMN)). Suspensions (50 ml) of isolated secretory cell clusters (~1.6×10$^6$ cells/ml) were disrupted by sonication in the presence of 25% (v/v) XAD-4 resin and 0.5–0.9 g of Polyvinylpolypyrrolidone (added based on the level of phenolics observed during tissue harvesting) with the probe (Braun-Sonic 2000) at maximum power; five times for 15 see with 1 min cooling periods between each 15 sec burst. After sonication, protein was extracted by gentle stirring at 4° C. for 20 min. The resulting extract was filtered through, and washed on, a 20 $\mu$m nylon mesh on a Buchner funnel under vacuum to remove XAD-4 beads, PVPP, and cell debris. The resulting filtrate (~80 ml) was homogenized in a chilled Tenbroek glass homogenizer and brought to 100 ml with sonication buffer. The sonicate was then centrifuged at 18,000×g to remove cellular debris and the resulting supernatant was centrifuged at 195,000×g to yield the glandular microsomal fraction. Microsomal pellets prepared from gland sonicates (originating from 110 g of spearmint apical tissue) were resuspended and homogenized in 6 ml of solubilization buffer (25 mM Tris (pH 7.4), 30% glycerol, 1 mM DTT, 1 mM EDTA, 20 mM octylglucoside) and incubated on ice at 4° C. overnight (under $N_2$). Insoluble material was removed by centrifugation at (195,000×g) for 90 min at 4° C. to provide the soluble supernatant used as the enzyme source for further purification.

Example 2

(−)-Limonene-6-Hydroxylase Purification

The solubilized protein fraction from Example 1 containing the (−)-limonene-6-hydroxylase was subjected to two rounds of hydrophobic interaction chromatography on methyl-agarose (Sigma Lot #97F9710, Aug. 6, 1992), followed by further purification by SDS-PAGE (Laemmli, *Nature* 227:680–685 [1970]). Hydrophobic interaction chromatography was performed at room temperature. Samples were kept on ice before loading and as fractions were collected. Typically, 3 to 6 nmol of solubilized cytochrome P450 measured by the method of Omura and Sato (Omura et al., *J. Biol. Chem.* 239:2379–2385 [1964]) were loaded onto a 3 ml methyl-agarose column (C-1), that was prepared and equilibrated with solubilization buffer. The flow-through of the first C-1 column (12 ml) was collected and loaded onto a second C-1 column (equilibrated as before). Following the removal of contaminants achieved on the first C-1 column, the cytochrome P450 bound to the second column and was selectively eluted with solubilization buffer plus substrate (2 $\mu$l/ml (−)-limonene mixed to an emulsion in buffer). Although this procedure proved useful for purification of the (−)-limonene-6-hydroxylase and for obtaining amino acid micro-sequence data from the pure enzyme, it was not reproducible with additional lots of methyl-agarose from Sigma and recovery yields varied greatly between individual protein preparations. To establish this example, it was therefore necessary to develop an alternative, reproducible protein purification strategy which is described for the first time in the following paragraph.

Alternative protein purification method—Microsomal pellets prepared from gland sonicates originating from 200–250 g of spearmint leaves (16–20) were resuspended in 5 ml of 25 mM HEPES buffer (pH 7.2), containing 20% glycerol, 25 mM KCl, 10 mM $MgCl_2$, 5 mM DTT, 0.2 mM PMSF, 50 µM BHT, and 10 mg/liter leupeptin using a glass Tenbroeck homogenizer. An equal volume of the same buffer containing 1% Emulgen 911 was added slowly dropwise while stirring on ice, and the stirring continued for 1 h. The suspension was then centrifuged for 90 min at 195,000× g. The resulting solubilized microsomes were used as the source of (−)-limonene hydroxylase for further purification, which consisted of a polyethylene glycol, (PEG) precipitation step followed by anion-exchange chromatography on DEAE Sepharose and chromatography on ceramic hydroxylapatite (the latter serves a dual function as a final purification step and a detergent removal step which is required to reconstitute (−)-limonene-6-hydroxylase catalytic activity in homogeneous protein preparations).

A 60% suspension of polyethylene glycol ($M_r$ 3,350) in HEPES buffer (above) with out detergent was added slowly dropwise to the solubilized microsomes while stirring on ice to give a final PEG concentration of 30%; stirring was continued for 30 min. The suspension was then centrifuged at 140,000×g for 60 min and the supernatant discarded. The resultant 0–30% PEG pellet was then resuspended in 5 ml of buffer containing 25 mM Tris-Cl (pH 7.0), 20% glycerol, 1 mM DTT and 50 µM BHT using a glass homogenizer. To this suspension was slowly added (dropwise) an equal volume of the same buffer containing 0.2% Emulgen 911 followed by stirring on ice for an additional 30 min. The suspension was then clarified by centrifugation at 140,000×g for 30 min.

The clarified PEG suspension was applied to a 3.5×1.75 cm column of DEAE Sepharose (Sigma or Pharmacia) equilibrated and washed with buffer (25 mM Tris-Cl (pH 7.0) containing 20% glycerol, 1 mM DTT, 50 µM BHT, and 0.1% Emulgen 911), at a rate of 1.75 ml/min. The remaining bound protein was eluted stepwise (75 ml/step) with the same buffer containing 50, 125, 250, and 1000 mM KCl. DEAE anion-exchange chromatography performed in this manner yields 45–60% of the microsomal P-450 measured by the method of Omura and Sato (Omura, supra) as an essentially homogeneous 57 kD protein (with a 21% P-450 yield relative to the glandular sonicate). Cytochrome P-450 containing fractions from the anion-exchange column were concentrated by Amicon YM-30 ultrafiltration (Amicon) and bound to ceramic hydroxylapatite (Sigma). Emulgen 911 was removed by washing the matrix with 5 mM potassium, 40 µm (Bio-Rad Laboratories) phosphate buffer (pH 7.4) containing 20% glycerol, 1 mM DTT, and 10 mM CHAPS. The matrix was further washed with the same phosphate buffer containing no detergent, after which the (−)-limonene-6-hydroxylase is eluted from hydroxylapatite with 240 mM potassium phosphate buffer containing 20% glycerol and 1 mM DTT.

Purified cytochrome P-450-containing fractions were combined and concentrated by TCA precipitation in preparation for SDS-PAGE. This protocol was shown to provide pure samples suitable for amino acid sequence analysis. TCA was added to protein samples at 8% (v/v), and the mixture was vigorously vortexed and incubated on ice for 40 min. Precipitated protein was pelleted by centrifugation for 15 min at 10,000×g at 4° C. The pellets were washed twice with ice cold acetone and vacuum desiccated to remove traces of organic solvent. The resulting pellets were resuspended in 75 µl of 1×Laemmli loading buffer (Laemmli, supra), frozen at −80° C. overnight and then heated for 15 min at 55° C. prior to SDS-PAGE.

Example 3

Amino Acid Analysis and Protein Sequencing

For obtaining N-terminal amino acid sequence data, the gels were electroblotted to polyvinyldifluoride membranes (Immobilon-$P^{SQ}$, Millipore) in 25 mM Tris, 192 mM glycine (pH 8.3) containing 20% (v/v) methanol (Towbin et al., Proc. Natl. Acad. Sci. USA 76:4350–4354 [1979]). Membranes were stained in 0.1% Coomassie Brilliant Blue R-250 in (methanol:acetic acid:water (50:10:40, v/v/v)) and destained with methanol:acetic acid:water (50:5:45). The resolved bands containing cytochrome P450 at ~57 kDa ((−)-limonene-6-hydroxylase) were excised, washed by vortexing in distilled water, and the membrane fragments containing the target proteins were subjected to sequence analysis via edman degradation on an Applied Biosystems 470 sequenator (at The Washington State University Laboratory for Bioanalysis and Biotechnology, Pullman, Wash.).

In order to obtain internal amino acid sequence information, protein samples were subjected to SDS-PAGE as described above. In this case, however, the gels were not directly electroblotted but were visualized by staining with 0.2% Coomassie Brilliant Blue R-250 in methanol:acetic acid:water (30:10:60, v/v/v) and destained with methanol:acetic acid:water (5:8:93, v/v/v) to avoid gel shrinkage. The gel band at 57 kDa was excised, washed with distilled water, and equilibrated in SDS-sample buffer (Laemmli, supra) for 5 min at room temperature. In a second SDS-PAGE step, the gels were polymerized with an extra large stacking gel and pre-electrophoresed as described above. The equilibrated gel slices from above were inserted into the sample well of the second SDS-10% polyacrylamide vertical slab gel (16 cm×18 cm×1.0 mm) which was previously filled with SDS-running buffer (Laemmli, supra). V-8 protease (2 µg) from Sigma was added to SDS sample buffer with 20% (v/v) glycerol and loaded using a Hamilton syringe into the sample well surrounding the gel slice. The samples were electrophoresed at 90 V (~⅔ of the way into the stacking gel). The power was turned off for 30 min in order to allow proteolytic cleavage. Electrophoresis was then continued at 90 V until the Bromophenol Blue dye front had entered the resolving gel. At this time, cooling was maintained at 20° C. and electrophoresis was continued at 20 mA constant current for ~3 h. Following electrophoresis, the gel was electroblotted, the resulting membrane was coomassie stained, and the resolved peptide bands were prepared for microsequence analysis as described above. This method of proteolytic cleavage routinely yielded three peptide fragments whose combined molecular weights equaled approximately 57 kDa.

Peptides were sequenced via Edman degradation on an Applied Biosystems 470 sequenator at the Washington State University Laboratory for Bioanalysis and Biotechnology, Pullman, Wash.

These methods yielded 20–25 residues of amino acid sequence data from each of the three V-8 derived peptides, as well as from the N-terminus of uncleaved (native) protein. The sequence of the second largest proteolytic peptide, V-8.2 (SEQ ID No:7) was identical to that of the corresponding region of the uncleaved protein (amino acid residues 1–21 of the sequence set forth in SEQ ID No:2) representing the N-terminus of the native enzyme. The V-8.3 (SEQ ID No:8) sequenced fragment could be most easily aligned with the C-terminal region of an avocado P450 (Bozak et al., *Proc. Natl. Acad Sci. USA* 87:3904–3908 [1990]) suggesting its origin from the same C-terminal region on the (−)-limonene hydroxylase. The V-8.3 fragment (SEQ ID No:8) corresponds to amino acids 375–398 of the amino acid sequence set forth in SEQ ID No:2. The third peptide fragment, V-8.1, (SEQ ID No:9) was assumed to be located somewhere between V-8.2 (SEQ ID No:7) and V-8.3 (SEQ ID No:8). [The avocado P450 was not a useful probe for limonene hydroxylases as it was not sufficiently similar]. The V-8.1 fragment (SEQ ID No:9) corresponds to amino acids 176–200 of the amino acid sequence set forth in SEQ ID No:2.

Example 4

PCR-based Probe Generation

Degeneracy considerations prevented the direct use for library screening of the amino acid sequence data generated from the purified (−)-limonene-6-hydroxylase from spearmint. PCR methods were employed to amplify the nucleotide sequences corresponding to the amino acid data. Six short, degenerate PCR primers were designed to prime the termini of each encoded peptide fragment. These primers are shown in the following Table 1:

cessfully employed to amplify the 75 bp nucleotide sequence encoding the V-8.1 peptide fragment (SEQ ID No:9).

Primer 1.AG (SEQ ID No:11) was designed for the same purpose as primer 1.AC (SEQ ID No:10). Primers 1.AC (SEQ ID No:10) and 1.AG (SEQ ID No:11) were synthesized separately and combined to create the primer 1.A in order to reduce the population degeneracy level in the primer pool.

Primer 1.C (SEQ ID No:13) primes the central region of the V-8.1 peptide fragment (SEQ ID No:9). This primer is a non-degenerate primer oriented in the forward direction and was successfully employed when combined with the primer 3.C (SEQ ID No:19) to amplify the nucleotide sequence spanning the V-8.1 (SEQ ID No:9) and V-8.3 (SEQ ID No:8) proteolytic peptide fragments. The amplified nucleotide sequence was utilized as a cDNA hybridization probe and named LH-1 (SEQ ID No:20).

Primer 2.AA (SEQ ID No:14) was designed to prime the amino-terminus of the nucleotide sequence based on the 5' end of the V-8.2 peptide fragment (SEQ ID No:7). This primer is oriented in the forward direction and was combined with the primer 2.AT (SEQ ID No:15) during PCR to achieve a lower degeneracy level in the primer pool.

Primer 2.AT (SEQ ID No:15) was designed for the same purpose and at the same location as the primer 2.AA (SEQ ID No:14).

TABLE 1

PCR Primers

```
Primer
Name    Primer Sequence (5' to 3')                              SEQ ID No.

1.AC    GTI ACI AAA ATG AC                                          10
            TG  G       T

1.AG    GTI ACI AAA ATG AG                                          11
            TG  G       T

1.B     GC CTC IGA ICC CTG ATC CTT                                  12
        T    CT      T   G   T

1.C     G TGT GTC GTC GTG TGC AGG GCG GCG TTC G                     13

2.AA    ATG GAG CTI GAC CTI CTI A                                   14
            A T G     T T G T G
                A         A   A

2.AT    ATG GAG CTI GAC CTI CTI T                                   15
            A T G     T T G T G
                A         A   A

2.B     TC IAT ATA IGT IGC IAC                                      16
               G

3.A     ATG GAG GTI AAC GGI TAC AC                                  17
                    A       T       T

3.B     TTT TTT TTT TTT TTT TTT A                                   18
                                T
                                C

3.C     CC GAT IGC GAT IAC GTT IAT AAA AAT ICT IGT CTT IGC IGG      19
              T       T       A         G   G   G       T
              A       A                     T
```

I = Inosine

Primer 1.AC (SEQ ID No:10) was designed to prime the 5' end of the proteolytic peptide fragment V-8.1 (SEQ ID No:9) in the forward orientation. This primer was combined with primer 1.AG (SEQ ID No:11) during PCR to create the oligonucleotide mixture called primer 1.A which was suc- Primer 2.B (SEQ ID No:16) was designed to prime the 3' end of the V-8.2 peptide fragment (SEQ ID No:9) in the reverse orientation.

Primer 3.A (SEQ ID No:17) designed to prime the 5' end of the V-8.3 peptide (SEQ ID No:8) fragment in the forward direction.

Primer 3.B (SEQ ID No:18) primes the poly(A) tail on cDNA molecules. This primer was designed in the reverse orientation to amplify nucleotide fragments when combined with any of the other forward primers.

Primer 3.C (SEQ ID No:19) was designed to prime the 3' end of the V-8.3 peptide fragment (SEQ ID No:8) in the reverse orientation.

Additional primers were designed to amplify regions spanning the three peptide fragments.

The PCR primers were employed in all possible combinations with a range of amplification conditions using spearmint gland cDNA as template. Analysis of PCR products by gel electrophoresis indicated that one primer set (1.A (the mixture of SEQ ID No:10 plus SEQ ID No:11) and 1.B (SEQ ID No:12)) had amplified the appropriate sized DNA fragment corresponding to the V-8.1 peptide (SEQ ID No:9). This 75 bp fragment was cloned into pT7Blue (Novagen), sequenced (by the chain termination method using Sequenase Version 2.0, United States Biochemical Corp.), and shown to code for the V-8.1 peptide (SEQ ID No:9). A non-degenerate forward primer (1.C) (SEQ ID No:13) was then designed from the internal coding sequence of V-8.1 (SEQ ID No:9) which, when combined with the degenerate reverse primer 3.C (SEQ ID No:19) designed to the V-8.3 peptide (SEQ ID No:8), permitted the amplification of a specific 700 bp DNA fragment (SEQ ID No:20). This fragment was cloned in to pT7Blue and sequenced as above, confirming that it coded for the sequence which spanned the V-8.1 (SEQ ID No:9) and V-8.3 (SEQ ID No:8) peptides. This fragment (LH-1, SEQ ID No:20) was then labeled with [$\alpha$-$^{32}$P-dATP] via the random hexamer reaction (Tabor et al., in *Current Protocols in Molecular Biology.* Sections 3.5.9–3.5.10, John Wiley and Sons Inc. New York [1991]) and was used as a hybridization probe to screen the spearmint oil gland cDNA library.

Example 5

Plasmid Formation and Screening cDNA Library Construction—Spearmint (*Mentha spicata*) and peppermint (*Mentha piperita*) oil gland specific cDNA libraries were constructed. As published (Gershenzon et al., *Anal. Biochem.* 200:130–138 [1992]), the glandular trichome secretory cell isolation procedure does not protect RNA from degrading during a long water imbibition prior to surface abrasion. To protect RNA from degradation, published RNA purification protocols require either immediate freezing of tissue in liquid nitrogen or immersion in either strong organic solvents or chaotropic salts (see prior RNA isolation methods submitted with limonene synthase patent). These protocols have proven themselves to be incompatible with gland cluster isolation. Additionally, most tissues do not have the high levels of RNA degrading phenolics found in mint secretory glands. Therefore, a reproducible procedure was developed that protects the RNA from degradation during leaf imbibition and subsequent gland isolation and extraction. Additions of the low molecular weight RNase inhibitor, aurintricarboxylic acid (ATCA) (Gonzales et al., *Biochemistry* 19:4299–4303 [1980]) and the low molecular weight polyphenyloxidase inhibitor, thiourea (Van Driessche et al.,*Anal. Biochem.* 141:184–188 [1984]), to the water used during imbibition were tested. These additions were shown not to adversely effect water imbibition and gland isolation, yet to greatly improve the yield and quality of subsequent RNA isolation. Optimum concentrations for ATCA and thiourea were found to be 5 mM and 1 mM, respectively. These modifications allowed gland clusters to be isolated that consistently contained undegraded RNA. RNA extraction and purification using the improved method of Logemann et al. (Logemann et al., *Anal. Biochem.* 163:16–20 [1987]) was compromised by phenolics released during initial disruption of the purified gland cells. The inclusion of insoluble polyvinylpolypyrrolidone (PVPP) (Lewinsohn et al., *Plant Mol. Biol. Rep.* 12(1):20–25 [1994]) to the RNA extraction buffer of Logemann et al., sufficiently sequestered phenolics and eliminated degradation. These modifications to the gland cell cluster isolation and RNA purification protocols consistently yield intact RNA that is useful for further manipulation. Poly (A)+ RNA was isolated on oligo (dT)-cellulose (Pharmacia Biotech, Inc.), and 5 $\mu$g of the resulting purified mRNA was utilized to construct a $\lambda$ZAP cDNA library for each Mentha species according to the manufacturer's instructions (Stratagene).

Spearmint gland cDNA Library Screening—The 700 bp nucleotide probe (LH-1, SEQ ID No:20) generated by the PCR strategy of Example 4 was employed to screen replicate filter lifts of $1 \times 10^5$ primary plaques grown in *E. coli* XL1-Blue MRF' using Stratagene protocols. Hybridization according to the DuPont-New England Nuclear protocol was for 24 h at 65° C. in 25 ml of hybridization solution consisting of 5×SSPE (1×SSPE=150 mM NaCl, 10 mM sodium phosphate, and 1 mM EDTA), 5×Denhardts, 1% SDS and 100 $\mu$g/ml denatured sheared salmon sperm DNA. Blots were washed twice for 10 min with 2×SSPE at room temperature, twice with 2×SSPE containing 2% SDS for 45 min at 65° C., and, finally, twice with 0.1×SSPE for 15 min at room temperature.

Of the plaques affording positive signals, 35 were purified through two additional cycles of hybridization. Thirty pure clones were in vivo excised as Bluescript SK (–) phagemids and their insert sizes were determined by PCR using T3 and T7 promoter primers. The largest 6 clones (~1.6 kb) were partially sequenced using T3 and T7 promoter primers. Three of these cDNA clones, 8A, 11A and 22C, were completely sequenced using nested deletion subclones generated with the Exo III/MungBean Nuclease Deletion Kit (Stratagene) as per manufacturer's instructions; additional sequencing primers, shown in the following Table 2 were also employed.

TABLE 2

Sequencing Primers

| Designation | Sequence | | SEQ ID No. |
|---|---|---|---|
| 22CR3 | CACGACATCTTCGACACCTCCTCC | | 21 |
| 22CF1 | GCAACCTACATCGTATCCCTCC | ** | 22 |
| NTREV1 | GGCTCGGAGGTAGGTTTTGTTGGG | | 23 |
| NTREV2 | GATTAGGAGGGATACGATGTAGGTTGC | | 24 |
| 11A4.25R6 | CTGGGCTCAGCAGCTCTGTCAA | | 25 |
| 4.25R5 | GGGCTCAGCAGCTCTCTC | | 26 |
| 4.25R3 | CTTCACCAACTCCGCCAACG | ** | 27 |
| 11A4.25R2 | GCTCTTCTTCTCCCTATGC | | 28 |
| 11A4.25R | TAGCTCTTGCACCTCGCTC | | 29 |
| 11A.1F4 | TTCGGGAGTGTGCTCAAGGACCAGG | | 30 |
| 11A1F3 | GTTGGTGAAGGAGTTCGCTG | | 31 |
| 11A.1F2 | CTTACAACGATCACTGG | | 32 |
| S12.2PF1 | GACATCGTCGACGTTCTTTTCAGG | | 33 |
| S12.2PF2 | CTACCACTTCGACTGGAAATTGC | | 34 |
| S12.2PF3 | CTGAGATCGGTGTTAAAGGAGAC | | 35 |
| S12.2PR1 | GCCACCTCTATAAGACACTCCTC | | 36 |
| S12-2PR2 | GATCTCAACATTTGCCAGC | | 37 |
| S12BF | GAAACCATGGAGCTCGACC | | 38 |
| P17.1F2 | CGACGACATCATCTTCAGC | | 39 |

TABLE 2-continued

Sequencing Primers

| Designation | Sequence | SEQ ID No. |
|---|---|---|
| P17F1 | AGTACGGTCCAGTGGTGCACGTGC | 40 |
| P17.1.2F3 | GAGGAGCTGGTGGAGCTGGTGAAG | 41 |
| P17.1.2F5 | CGAGATCATGCAGAGAAGAATGC | 42 |
| P17R1 | ATGGGACCTCAACATTTGGCAAC | 43 |
| P17.1R2 | ATGTTCTTGGCCTTATTCG | 44 |
| P17.1.2R4 | CAGAGCAAGTTGAGGAGCTTGGAGG | 45 |
| P17.1.2F4 | CCATCACCACCAACGCCATCAAAGC | 46 |
| P17.1.2R6 | GTACTGCTTCGCCACGCTGG | 47 |
| BLUT3 | CGCGCAATTAACCCTCACTAAAGGG | 48 |
| 11A4.10F | GCTGAATGGGCAATGG | 49 |
| 11A.1F-A | CACCTCCACTTCCTGTGG | 50 |
| P17.1.2R5 | GCTGAAGAGCTCGGAGACGCAGATC | 51 |

**These primers were used as PCR primers to construct the cDNA hybridization probe LH-2 (SEQ ID No:52) in addition to being used as sequencing primers.

DNA fragments were assembled, and the sequence was analyzed using Seq AID II version 3.8 (a public domain program provided by Rhodes, D. D., and Roufa, D. J., Kansas State University) and the Genetics Computer Group Packet (The Genetics Computer Group, *Program Manual for the Wisconsin Packet, Version* 8, Genetics Computer Group, Madison, Wis. [1994]). Following alignment of the cDNA sequences with the peptide sequences obtained, it was determined that all three of these cDNA clones were truncated at the N-terminus; clone 22C was also truncated at the C-terminus and clone 8A was shuffled. Therefore, a second nucleotide probe (LH-2, SEQ ID No:52) was generated by PCR using a new forward primer (22CF, SEQ ID No:53), homologous to the 20 most N-terminal bases of clone 22C and a new reverse primer 4.25R3, SEQ ID No:54 (priming a region 500 bp downstream on clone 22C). The resulting DNA fragment (probe LH-2, SEQ ID No:52) was employed to re-screen the spearmint gland library as above. The second screen yielded 30 purified clones, which were in vivo excised and partially sequenced (Dye Deoxy Terminator Cycle Sequencing. Applied Biosystems). A single full-length clone, designated pSM12.2 (SEQ ID No:1), was isolated (1762 bp in length) and found to encode the entire protein (SEQ ID No:2) by comparison to the original amino acid sequence data. The limonene-6-hydroxylase protein set forth in SEQ ID No:2 includes a membrane insertion sequence at amino acids 1–42; a halt-transfer signal at amino acids 38–42, and a heme-binding region at amino acids 423–448.

Isolation of peppermint cytochrome P450 cDNA clones— One hundred thousand primary (peppermint gland cDNA) plaques were grown and screened by hybridization with probe LH-2 (SEQ ID No:52) employing the same methods, as described above, used to isolate the spearmint cDNA clone pSM12.2 (SEQ ID No:1). Of the 25 plaques that were purified, ten were in vivo excised and partially sequenced with T3 and T7 promoter primers. Sequence alignment indicated that seven of these were representatives of the same gene (one of which, pPM17, was a full length clone and was completely sequenced). The nucleotide sequences for both cloned inserts, pSM12.2 ((−)-limonene-6-hydroxylase), and pPM17 ((−)-limonene-3-hydroxylase) are shown in SEQ ID No:1 and SEQ ID No:3, respectively.

Baculovirus Constructs—Site directed mutagenesis PCR was employed to subclone the (−)-limonene-6-hydroxylase cDNA (pSM12.2, SEQ ID No:1) into the baculovirus transfer vector pBlueBac3 (Invitrogen). PCR primers (see Table 3, below) were designed to add restriction sites (NcoI) at the 5' translation initiation codon extending to a second primer at a position 20 bp downstream of the translation termination codon, thus creating a HindIII site. The resulting fragment was digested, gel purified, ligated into NcoI-HindIII restricted pBlueBac3, and transformed into *E. coli* DH5α cells, thus creating the baculovirus transfer vector pBac12.2.

TABLE 3

PCR Primers used to construct the baculovirus transfer vectors pSM12.2 and pPM17.35:

| Designation | Sequence | SEQ ID No. |
|---|---|---|
| P17START | ATGGAGCTTCAGATTTCG | 55 |
| p17RSTOP | GCACTCTTTATTCAAAGG AGC | 56 |
| S12BF | GAAACCATGGAGCTCGACC | 57 |
| S12BR | TATGCTAAGCTTCTTAGTGG | 58 |
| BAC4PCR-F | TTTACTGTTTTCGTAACAGTTTTG | 59 |
| BAC4PCR-R | CAACAACGCACAGAATCTAGC | 60 |
| BAC3PCR-F | TTTACTGTTTTCGTAACAGTTTTG | 61 |
| BAC3PCR-R | CAACAACGCACAGAATCTAGC | 62 |

The (−)-limonene-3-hydroxylase cDNA (pPM17, SEQ ID No:3) was cloned into the baculovirus transfer vector pBlueBac4 (Invitrogen) by PCR using the thermal stable, high fidelity, blunting polymerase Pfu I (Stratagene) with PCR primers pE17Start (at the translation initiation ATG) and pE17Stop (extending 21 bp downstream of the translation termination codon) into the 3' untranslated region. The resulting blunt-ended fragment was ligated into Nhe I digested pBlueBac4 (Invitrogen), that had been filled in via Klenow enzyme (Boehringer Mannheim), and was transformed into *E. coli* DH5α, thus yielding the baculovirus transfer vector pBac17.35. Both transfer vectors were completely resequenced to verify cloning junctions; no errors were introduced by polymerase reactions.

Recombinant baculovirus was constructed as described by Summers and Smith (Summers et al, *A Manual of Methods for Baculovirus Vectors and Insect Cell Culture Procedures*, Bulletin No. 1555, Texas Agricultural Experiment Station, College Station, Tex. [1988]). Briefly, CsCl banded transfer vector was cotransfected into *Spodoptera frugiperda* (Sf9) cells with purified, linearized AcMNPV DNA by the method of cationic liposome mediated transfection (Invitrogen) as per the manufacturer's instructions. Recombinant virus was identified by the formation of blue (occlusion negative) plaques using established plaque assay procedures (Summers et al., supra; O'Reilly et al., *Baculovirus Expression Vectors, A Laboratory Manual*, Oxford: Oxford University Press, pp. 45–50, 109–166 [1994]; Smith et al., *Lancet* 339:1375–1377 [1992]). Putative recombinant viruses were monitored for purity by PCR analysis and gel electrophoresis.

Example 6 cDNA Expression

Sf9 Cell Culture and Recombinant Protein Expression— *Spodoptera frugiperda* (Sf9) cells were maintained as monolayers or in suspension (85–90 RPM) culture at 27° C. in Grace's media (Gibco BRL supplemented with 600 mg/L L-glutamine, 4 g/L yeastolate, 3.3 g/L, lactoalbumin hydrolyste, 10% (v/v) fetal bovine serum, 0.1% pluronic F-68, and 10 μg gentamicin/ml). For the generation of high titer viral stocks, suspension cultures of log phase cells (1.1 to $1.6 \times 10^6$ cells/ml) were infected at a multiplicity of infection (MOI) equal to ~0.1 PFU/cell, and then allowed to grow until near complete cell lysis had occurred. Cell debris was pelleted by centrifugation and the media stored at 4° C. For expression, log phase suspension cultures of Sf9 cells were supplemented with 3 μg hemin chloride/ml (Sigma) in 75 mM sodium phosphate and 0.1 N NaOH (pH 7.6) and infected with recombinant baculovirus at an MOI of between 5 and 10 PFU/cell. The addition of hemin to the culture media was required to compensate for the low heme synthetic capability of the insect cells. Cells were harvested at various time intervals (between 24 and 96 hours post infection) by centrifugation (800×g, 10 min), then washed with PBS, and resuspended in 75 mM sodium phosphate buffer (pH 7.4) containing 30% glycerol, 1 mM DTT, and 1 mM EDTA.

Example 7

Limonene Hydroxylase Analysis

Product analysis and other analytical methods—An in situ bioassay was developed to evaluate functional expression of (−)-limonene hydroxylase activity. Expression cultures were incubated in the presence of ~300 μM (−)-(4S)-limonene, which was added to the culture medium immediately following infection. At zero and various time intervals, 50–100 ml culture samples were removed and cells were harvested by centrifugation, washed, and resuspended in 3–6 ml of sodium phosphate buffer as described above. Resuspended cell suspensions were chilled on ice and extracted twice with 3 ml portions of ice cold ether after the addition of 25 nmol camphor as internal standard. The extract was decolorized with activated charcoal, backwashed with water, and the organic phase containing the products was passed through a short column of anhydrous $MgSO_4$ and activated silica. The purified extracts were then concentrated to ~500 μl under $N_2$ and analyzed by capillary GLC (Hewlett-Packard 5890). GLC was performed on 0.25 mm i.d×30 m of fused silica capillary columns coated with superox FA or AT-1000 using "on column" injection and flame ionization detection with $H_2$ as carrier gas at 13.5 psi (programmed from 45° C. (5 min) to 220° C. at 10° C. per min). The identities of the products, (−)-trans-carveol from C-6 hydroxylation and (−)-trans-isopiperitenol from C-3 hydroxlyation, were confirmed by coincidence of retention times with the corresponding authentic standard. Peak quantitation was by electronic integration based on the internal standard.

Functional expression of the (−)-limonene-6-hydroxylase (pSM12.2)(SEQ ID No:1), from spearmint and the (−)-limonene-3-hydroxylase from peppermint (pPM17)(SEQ ID No:3), using the in situ bioassay thus confirmed the identity of the clones. GLC and GLC-MS analysis of Sf9 expression cultures infected with Baculovirus clones pBac12.2 and pBac17.35 verified the production of between 15 and 35 nmol of the expected oxygenated monoterpene product ((−)-trans-carveol from the spearmint clone and (−)-trans-isopiperitenol from the peppermint clone) per 50 ml of expression culture. Non-infected Sf9 control cultures grown under expression conditions and fed limonene substrate, control cultures infected with recombinant baculovirus but not fed limonene, and Sf9 cells alone evidenced no detectable carveol or isopiperitenol production, as expected. Cell free extracts of the transfected cells yielded a typical CO-difference spectrum (Omura et al., *J. Biol. Chem.* 239:2379–2385 [1964]) and afforded a positive Western blot (using antibody directed against the native spearmint 6-hydroxylase) thus demonstrating the recombinant enzymes to resemble their native counterparts, which have been previously isolated and characterized (but not previously purified) from the respective mint species (Karp et al., *Arch. Biochem. Biophys.* 276:219–226 [1990]), and confirming that the isolated genes are those controlling the oxidation pattern of limonene in monoterpene metabolism (Gershenzon et al., *Rec. Adv. Phytochem.* 28:193–229 [1994]).

Example 8

Cloning and Characterization of an Additional cDNA Molecule Encoding Limonene-3-Hydroxylase from Peppermint An additional cDNA molecule called PM2 (SEQ ID No:5), encoding a naturally-occurring limonene-3-hydroxylase variant (SEQ ID No:6), was cloned, concurrently with limonene-3-hydroxylase cDNA PM17 (SEQ ID No:3), from a peppermint cDNA library using the LH-2 fragment (SEQ ID No:52) as a probe. The PM2 cDNA (SEQ ID No:5) exhibits 93% identity with the nucleic acid sequence set forth in SEQ ID No:3 which also encodes a limonene-3-hydroxylase from peppermint (SEQ ID No:4). The limonene-3-hydroxylase (SEQ ID No:6), encoded by the cDNA having the nucleic acid sequence set forth in SEQ ID No:5 exhibits 97% similarity with the limonene-3-hydroxylase (SEQ ID No:4) encoded by the cDNA having the nucleic acid sequence set forth in SEQ ID No:3.

Example 9

Physical Properties of Isolated, Recombinant Limonene-3-Hydroxylase and Limonene-6-Hydroxylase Proteins of the Present Invention Preferred limonene-3-hydroxylase and limonene-6-hydroxylase proteins of the present invention are members of the cytochrome P450 oxygenase superfamily (subfamily Cyp71D) described in Nelson et al., *DNA Cell Biol.* 12:1–51 (1993) and Nelson et al., *Pharmacogenetics* 6: 1–42 (1996), and require oxygen and NADPH or NADH for biological activity. Preferred limonene-3-hydroxylase and limonene-6-hydroxylase proteins of the present invention exhibit pH optima in the range of pH 7.0 to pH 8.0, pI values of pH 7.0+/−1.5, and are about 56 kDa to about 60 kDa in size. Preferred limonene-3-hydroxylase and limonene-6-hydroxylase proteins of the present invention are inhibited by substituted azoles and carbon monoxide (with reversal of inhibition by the latter by blue light having a wavelength of 450 nm), bind tightly to their substrates ($K_m$<50 μM) and exhibit relatively low turnover ($K_{cat}$<100). The preferred substrate of preferred limonene-3-hydroxylase and limonene-6-hydroxylase proteins of the present invention is (−)-limonene, but these enzymes can also utilize (+)-limonene and the dihydrolimonenes. Preferred limonene-3-hydroxylases of the present invention can form both cis and trans C3 hydroxylation products, while preferred limonene-6-hydroxylases of the present invention can form both cis and trans C6 hydroxylation products.

Example 10

Hybridization of Fragment of Spearmint Limonene-6-Hydroxylase cDNA (SEQ ID No:52) to Other Nucleic Acid Sequences of the Present Invention Utilizing Northern blot analysis, the spearmint limonene-6-hydroxylase cDNA fragment set forth in SEQ ID No:52 (fragment LH-2), or its complementary sequence, is capable of hybridizing to other nucleic acids of the present invention under the following conditions: hybridization in 3×SSC at 65° C. for 16 hours. Once hybridized under the foregoing hybridization conditions, the spearmint limonene-6-hydroxylase cDNA fragment set forth in SEQ ID No:52, or its complementary sequence, is capable of remaining hybridized to other nucleic acids of the present invention under the following wash conditions: two washes in 2×SSC at room temperature (20° C. to 25° C.) for 20 minutes per wash, followed by one wash in 0.5×SSC at 50° C. for 30 minutes.

The ability of the nucleic acid molecules of the present invention to hybridize, and to remain hybridized, to the nucleic acid sequence set forth in SEQ ID No:52, or to the complementary sequence of the nucleic acid sequence set forth in SEQ ID No:52, can be determined utilizing the technique of hybridizing radiolabelled nucleic acid probes to nucleic acids immobilized on nitrocellulose filters or nylon membranes as set forth, for example, at pages 9.52 to 9.55 of *Molecular Cloning, A Laboratory Manual* (2nd edition), J. Sambrook, E. F. Fritsch and T. Maniatis eds, the cited pages of which are incorporated herein by reference.

Utilizing the foregoing hybridization and wash conditions, the nucleic acid sequence set forth in SEQ ID No:52, and its antisense complement, were radiolabelled and used to probe a Northern blot, bearing RNA samples from several essential oil plant species, in the following manner. The method of Lewinsohn et al. (Lewinsohn et al., *Plant. Mol. Biol. Rep.* 21: 20–25 (1994)) was utilized to isolate RNA from young leaves of the following essential oil plant species: *Mentha arvensis, Mentha pulegium, Mentha gentilis (gracilis), Nepeta cataria* (unknown chemotype), *Perilla frutescens* (unknown chemotype), *Tanacetum vulgare* (local chemotype), *Pelargonium graveolens* (unknown variety) and *Carum carvi*. 20 µg of total RNA from each of the foregoing species were separated on a 1.5% agarose gel containing 6% formaldehyde.

The gel containing the separated RNA samples was blotted onto Hybond N+ Nylon membrane (Amersham) and was prehybridized for one hour at 42° C. The nucleic acid sequence set forth in SEQ ID No:52 was used as a template for generating a $^{32}$P-labelled hybridization probe. The hybridization and wash conditions were as described in the present Example. Autoradiography revealed that the hybridization probe recognized a single RNA band of 1.6–1.8 kb in each of the samples.

Example 11

Additional Representative Nucleic Acid Molecules Encoding Either Limonene-3-Hydroxylase or Limonene-6-Hydroxylase In addition to the nucleic acid sequence set forth in SEQ ID No:1, examples of representative nucleic acid sequences of the present invention that encode a limonene-6-hydroxylase and which hybridize to the complementary sequence of the nucleic acid sequence disclosed in SEQ ID No:1 under the hybridization conditions set forth in Example 10 (and which remain hybridized under the wash conditions set forth in Example 10) are set forth in SEQ ID No:63 (encoding the limonene-6-hydroxylase variant set forth in SEQ ID No:64); and SEQ ID No:65 (encoding the limonene-6-hydroxylase variant set forth in SEQ ID No:66).

In addition to the nucleic acid sequences set forth in SEQ ID No:3 and SEQ ID No:5, examples of representative nucleic acid sequences of the present invention that encode a limonene-3-hydroxylase and which hybridize to the complementary sequence of the nucleic acid sequence disclosed in SEQ ID No:3 under the hybridization conditions set forth in Example 10 (and which remain hybridized under the wash conditions set forth in Example 10) are set forth in SEQ ID No:67 (encoding the limonene-3-hydroxylase variant set forth in SEQ ID No:68) and SEQ ID No:69 (encoding the limonene-3-hydroxylase variant set forth in SEQ ID No:70).

The nucleic acid sequences set forth in SEQ ID No:63, SEQ ID No:65, SEQ ID No:67 and SEQ ID No:69 were generated using a computer. The protein encoded by the nucleic acid set forth in SEQ ID No:63 is identical to the protein encoded by the nucleic acid set forth in SEQ ID No:1, except that the protein encoded by the nucleic acid set forth in SEQ ID No:63 includes a proline residue at position 228 of the protein sequence set forth in SEQ ID No:64, whereas the protein encoded by the nucleic acid set forth in SEQ ID No:1 has a leucine residue at position 228 of the protein sequence set forth in SEQ ID No:2.

The protein encoded by the nucleic acid set forth in SEQ ID No:65 is identical to the protein encoded by the nucleic acid set forth in SEQ ID No:1, except that the protein encoded by the nucleic acid set forth in SEQ ID No:65 includes a glutamic acid residue at position 117 of the protein sequence set forth in SEQ ID No:66, whereas the protein encoded by the nucleic acid set forth in SEQ ID No:1 has an aspartic acid residue at position 117 of the protein sequence set forth in SEQ ID No:2.

The protein encoded by the nucleic acid set forth in SEQ ID No:67 is identical to the protein encoded by the nucleic acid set forth in SEQ ID No:3, except that the protein encoded by the nucleic acid set forth in SEQ ID No:67 includes a lysine residue at position 289 of the protein sequence set forth in SEQ ID No:68, whereas the protein encoded by the nucleic acid set forth in SEQ ID No:3 has an asparagine residue at position 289 of the protein sequence set forth in SEQ ID No:4.

The protein encoded by the nucleic acid set forth in SEQ ID No:69 is identical to the protein encoded by the nucleic acid set forth in SEQ ID No:3, except that the protein encoded by the nucleic acid set forth in SEQ ID No:69 includes an aspartic acid residue at position 254 of the protein sequence set forth in SEQ ID No:70, whereas the protein encoded by the nucleic acid set forth in SEQ ID No:3 has a glutamic acid residue at position 254 of the protein sequence set forth in SEQ ID No:4.

Example 12

Hybridization Under Stringent Hybridization Conditions

The present invention provides isolated nucleic acid molecules that hybridize under stringent hybridization conditions to a fragment (having a length of at least 15 bases) of any one of the nucleic acid molecules set forth in SEQ ID No:1, SEQ ID No:3, SEQ ID No:5, SEQ ID No:63, SEQ ID No:65, SEQ ID No:67 and SEQ ID No:69. Hybridization under stringent hybridization conditions is achieved as follows. Nitrocellulose membranes are washed three to five times in 3×SSC with 0.1% SDS at room temperature and prehybridized for one hour at 37° C. in 6×SSC, 5×Denhart's solution, 0.05% sodium pyrophosphate, 0.5% SDS and 100 µg/ml boiled herring sperm DNA. High stringency hybridization is conducted in 6×SSC, 1×Denhart's solution, 0.1 mg/ml yeast tRNA, 0.05% sodium pyrophosphate at 45° C.

for twenty four to forty eight hours. The filters are washed three to five times for ten minutes per wash in 6×SSC, 0.5% sodium pyrophosphate at room temperature, and once for 30 minutes in 6×SSC, 0.05% sodium phosphate at 55° C. Low stringency hybridization is identical to high stringency hybridization, except that the hybridization temperature is 35° C. and the last wash is conducted at 50° C. instead of 55° C.

Presently preferred fragments useful for hybridizing to isolated nucleic acid molecules of the present invention include: nucleic acid residues 1274–1288 of SEQ ID No:1; nucleic acid residues 1301–1315 of SEQ ID No:1 and nucleic acid residues 1385–1399 of SEQ ID No:1.

The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

A 50×stock solution of Denhart's solution contains 5 g Ficoll (Type 400, Pharmacia), 5 g of polyvinylpyrrolidone, 5 g of bovine serum albumin (Fraction V, Sigma) and water to 500 ml.

While the preferred embodiments of the invention have been illustrated and described, it will be appreciated that various changes can be made therein without departing from the spirit and scope of the invention. For example, sequence variations from those described and claimed herein as deletions, substitutions, mutations, insertions and the like are intended to be within the scope of the claims except insofar as limited by the prior art.

The embodiments of the invention in which an exclusive property or privilege is claimed are defined as follows:

1. An isolated nucleic acid molecule that hybridizes to a nucleic acid molecule having the nucleic acid sequence set forth in SEQ ID No:52, or the complementary sequence of the nucleic acid sequence set forth in SEQ ID No:52, under hybridization conditions of 3xSSC at 65° C. for 16 hours, said isolated nucleic acid molecule remaining hybridized to a nucleic acid molecule having the nucleic acid sequence set forth in SEQ ID No:52, or the complementary sequence of the nucleic acid sequence set forth in SEQ ID No:52, under wash conditions of 0.5xSSC at 50° C. for 30 minutes.

2. An isolated nucleic acid molecule of claim 1 encoding limonene-6-hydroxylase.

3. An isolated nucleic acid molecule of claim 2 encoding limonene-6-hydroxylase from a genus selected from the group consisting of Mentha, Nepeta, Perilla, Tanacetum, Pelargonium and Carum.

4. An isolated nucleic acid molecule of claim 1 encoding limonene-3-hydroxylase.

5. An isolated nucleic acid molecule of claim 4 encoding limonene-3-hydroxylase from a genus selected from the group consisting of Mentha, Nepeta, Perilla, Tanacetum, Pelargonium and Carum.

6. An isolated nucleic acid molecule of claim 1 which encodes the amino acid sequence of SEQ ID No:6.

7. An isolated nucleic acid molecule of claim 1 comprising the nucleic acid sequence set forth in SEQ ID No:5.

8. A replicable expression vector comprising a nucleic acid molecule that hybridizes to a nucleic acid molecule consisting of the nucleic acid sequence set forth in SEQ ID No:52, or the complementary sequence of the nucleic acid sequence set forth in SEQ ID No:52, under hybridization conditions of 3xSSC at 65° C. for 16 hours, said hybridizing nucleic acid molecule remaining hybridized to said nucleic acid molecule consisting of the nucleic acid sequence set forth in SEQ ID No:52, or the complementary sequence of the nucleic acid sequence set forth in SEQ ID No:52, under wash conditions of 0.5xSSC at 50° C. for 30 minutes.

9. A replicable expression vector of claim 8 wherein said nucleic acid molecule that hybridizes to a nucleic acid molecule consisting of the nucleic acid sequence set forth in SEQ ID No:52, or the complementary sequence of the nucleic acid sequence set forth in SEQ ID No:52, encodes a limonene-6-hydroxylase.

10. A replicable expression vector of claim 8 wherein said nucleic acid molecule that hybridizes to a nucleic acid molecule consisting of the nucleic acid sequence set forth in SEQ ID No:52, or the complementary sequence of the nucleic acid sequence set forth in SEQ ID No:52, encodes a limonene-3-hydroxylase.

11. A replicable expression vector of claim 8 wherein said nucleic acid molecule that hybridizes to a nucleic acid molecule consisting of the nucleic acid sequence set forth in SEQ ID No:52, or the complementary sequence of the nucleic acid sequence set forth in SEQ ID No:52, comprises the sequence of SEQ ID No:5.

12. A host cell comprising a vector of claim 8.

13. A host cell of claim 12 wherein said host cell is a plant cell.

14. An isolated nucleic acid molecule that hybridizes to any one of the nucleic acid molecules set forth in SEQ ID No:1, SEQ ID No:3, SEQ ID No:5, SEQ ID No:63, SEQ ID No:65, SEQ ID No:67 and SEQ ID No:69, or to the complementary sequence of any one of the nucleic acid molecules set forth in SEQ ID No:1, SEQ ID No:3, SEQ ID No:5, SEQ ID No:63, SEQ ID No:65, SEQ ID No:67, and SEQ ID No:69, under hybridization conditions of 3xSSC at 65° C. for 16 hours, said isolated nucleic acid molecule remaining hybridized to any one of the nucleic acid molecules set forth in SEQ ID No:1, SEQ ID No:3, SEQ ID No:5, SEQ ID No:63, SEQ ID No:65, SEQ ID No:67 and SEQ ID No:69, or to the complementary sequence of any one of the nucleic acid molecules set forth in SEQ ID No:1, SEQ ID No:3, SEQ ID No:5, SEQ ID No:63, SEQ ID No:65, SEQ ID No:67 and SEQ ID No:69, under wash conditions of 0.5xSSC at 50° C. for 30 minutes.

15. A method of altering the production of limonene-6-hydroxylase in a suitable host cell comprising introducing into the host cell an expression vector of claim 8 wherein said nucleic acid molecule that hybridizes to a nucleic acid molecule consisting of the nucleic acid sequence set forth in SEQ ID No:52, or the complementary sequence of the nucleic acid sequence set forth in SEQ ID No:52, encodes a protein having the biological activity of the protein of SEQ ID No:2, said introduction of the expression vector into the host cell occurring under conditions enabling expression of the protein in the host cell.

16. A method of altering the production of limonene-3-hydroxylase in a suitable host cell comprising introducing into the host cell an expression vector of claim 8 wherein said nucleic acid molecule that hybridizes to a nucleic acid molecule consisting of the nucleic acid sequence set forth in SEQ ID No:52, or the complementary sequence of the nucleic acid sequence set forth in SEQ ID No:52, encodes a protein having the biological activity of the protein of SEQ ID No:4, said introduction of the expression vector into the host cell occurring under conditions enabling expression of the protein in the host cell.

* * * * *

SEQUENCE LISTING

<160> NUMBER OF SEQ ID NOS: 70

<210> SEQ ID NO 1
<211> LENGTH: 1762
<212> TYPE: DNA
<213> ORGANISM: Mentha spicata
<220> FEATURE:
<221> NAME/KEY: CDS
<222> LOCATION: (20)..(1507)

<400> SEQUENCE: 1

```
aaaaaactaa aaagaaaca atg gag ctc gac ctt ttg tcg gca att ata atc      52
                    Met Glu Leu Asp Leu Leu Ser Ala Ile Ile Ile
                     1               5                  10 ctt gtg gca acc tac atc gta tcc ctc cta atc aac caa tgg cga aaa     100
Leu Val Ala Thr Tyr Ile Val Ser Leu Leu Ile Asn Gln Trp Arg Lys
                 15                  20                  25 tcg aaa tcc caa caa aac cta cct ccg agc cct ccg aag ctg ccg gtg     148
Ser Lys Ser Gln Gln Asn Leu Pro Pro Ser Pro Pro Lys Leu Pro Val
             30                  35                  40 atc ggc cac ctc cac ttc ctg tgg gga ggg ctt ccc cag cac gtg ttt     196
Ile Gly His Leu His Phe Leu Trp Gly Gly Leu Pro Gln His Val Phe
         45                  50                  55 agg agc ata gcc cag aag tac ggg ccg gtg gcg cac gtg cag ctg gga     244
Arg Ser Ile Ala Gln Lys Tyr Gly Pro Val Ala His Val Gln Leu Gly
 60                  65                  70                  75 gaa gtg tac tcg gtg gtg ctg tcg tcg gcg gag gca gcg aag cag gcg     292
Glu Val Tyr Ser Val Val Leu Ser Ser Ala Glu Ala Ala Lys Gln Ala
                 80                  85                  90 atg aag gtg ctg gac ccg aac ttc gcc gac cgg ttc gac ggc atc ggg     340
Met Lys Val Leu Asp Pro Asn Phe Ala Asp Arg Phe Asp Gly Ile Gly
             95                 100                 105 tcc agg acc atg tgg tac gac aaa gat gac atc atc ttc agc cct tac     388
Ser Arg Thr Met Trp Tyr Asp Lys Asp Asp Ile Ile Phe Ser Pro Tyr
        110                 115                 120 aac gat cac tgg cgc cag atg cgg agg atc tgc gtg aca gag ctg ctg     436
Asn Asp His Trp Arg Gln Met Arg Arg Ile Cys Val Thr Glu Leu Leu
    125                 130                 135 agc ccg aag aac gtc agg tcc ttc ggg tac ata agg cag gag gag atc     484
Ser Pro Lys Asn Val Arg Ser Phe Gly Tyr Ile Arg Gln Glu Glu Ile
140                 145                 150                 155 gag cgc ctc atc cgg ctc ctc ggg tcg tcg ggg gga gcg ccg gtc gac     532
Glu Arg Leu Ile Arg Leu Leu Gly Ser Ser Gly Gly Ala Pro Val Asp
                160                 165                 170
```

```
gtg acg gag gag gtg tcg aag atg tcg tgt gtc gtc gtg tgc agg gcg        580
Val Thr Glu Glu Val Ser Lys Met Ser Cys Val Val Val Cys Arg Ala
        175                 180                 185 gcg ttc ggg agt gtg ctc aag gac cag ggt tcg ttg gcg gag ttg gtg        628
Ala Phe Gly Ser Val Leu Lys Asp Gln Gly Ser Leu Ala Glu Leu Val
        190                 195                 200 aag gag tcg ctg gca ttg gcg tcc ggg ttt gag ctg gcg gat ctc tac        676
Lys Glu Ser Leu Ala Leu Ala Ser Gly Phe Glu Leu Ala Asp Leu Tyr
205                 210                 215 cct tcc tca tgg ctc ctc aac ctg ctt agc ttg aac aag tac agg ttg        724
Pro Ser Ser Trp Leu Leu Asn Leu Leu Ser Leu Asn Lys Tyr Arg Leu
220                 225                 230                 235 cag agg atg cgc cgc cgc ctc gat cac atc ctt gat ggg ttc ctg gag        772
Gln Arg Met Arg Arg Arg Leu Asp His Ile Leu Asp Gly Phe Leu Glu
                240                 245                 250 gag cat agg gag aag aag agc ggc gag ttt gga ggc gag gac atc gtc        820
Glu His Arg Glu Lys Lys Ser Gly Glu Phe Gly Gly Glu Asp Ile Val
                255                 260                 265 gac gtt ctt ttc agg atg cag aag ggc agc gac atc aaa att ccc att        868
Asp Val Leu Phe Arg Met Gln Lys Gly Ser Asp Ile Lys Ile Pro Ile
                270                 275                 280 act tcc aat tgc atc aag ggt ttc att ttc gac acc ttc tcc gcg gga        916
Thr Ser Asn Cys Ile Lys Gly Phe Ile Phe Asp Thr Phe Ser Ala Gly
                285                 290                 295 gct gaa acg tct tcg acg acc atc tca tgg gcg ttg tcg gaa ctg atg        964
Ala Glu Thr Ser Ser Thr Thr Ile Ser Trp Ala Leu Ser Glu Leu Met
300                 305                 310                 315 agg aat ccg gcg aag atg gcc aag gtg cag gcg gag gta aga gag gcg       1012
Arg Asn Pro Ala Lys Met Ala Lys Val Gln Ala Glu Val Arg Glu Ala
                320                 325                 330 ctc aag gga aag aca gtc gtg gat ttg agc gag gtg caa gag cta aaa       1060
Leu Lys Gly Lys Thr Val Val Asp Leu Ser Glu Val Gln Glu Leu Lys
                335                 340                 345 tac ctg aga tcg gtg tta aag gag act ctg agg ctg cac cct ccc ttt       1108
Tyr Leu Arg Ser Val Leu Lys Glu Thr Leu Arg Leu His Pro Pro Phe
                350                 355                 360 cca tta atc cca aga caa tcc agg gaa gaa tgc gag gtt aac ggg tac       1156
Pro Leu Ile Pro Arg Gln Ser Arg Glu Glu Cys Glu Val Asn Gly Tyr
365                 370                 375 acg att ccg gcc aaa act aga atc ttc atc aac gtc tgg gct atc gga       1204
Thr Ile Pro Ala Lys Thr Arg Ile Phe Ile Asn Val Trp Ala Ile Gly
380                 385                 390                 395 agg gat ccc caa tac tgg gaa gat ccc gac acc ttc cgc cct gag aga       1252
Arg Asp Pro Gln Tyr Trp Glu Asp Pro Asp Thr Phe Arg Pro Glu Arg
                400                 405                 410 ttc gat gag gtt tcc agg gat ttc atg gga aac gat ttc gag ttc atc       1300
Phe Asp Glu Val Ser Arg Asp Phe Met Gly Asn Asp Phe Glu Phe Ile
                415                 420                 425 cca ttc ggg gcg ggt cga aga atc tgc ccc ggt tta cat ttc ggg ctg       1348
Pro Phe Gly Ala Gly Arg Arg Ile Cys Pro Gly Leu His Phe Gly Leu
                430                 435                 440 gca aat gtt gag atc cca ttg gcg caa ctc ctc tac cac ttc gac tgg       1396
Ala Asn Val Glu Ile Pro Leu Ala Gln Leu Leu Tyr His Phe Asp Trp
                445                 450                 455 aaa ttg cca caa gga atg act gat gcc gac ttg gac atg acg gag acc       1444
Lys Leu Pro Gln Gly Met Thr Asp Ala Asp Leu Asp Met Thr Glu Thr
460                 465                 470                 475 cca ggt ctt tct ggg cca aaa aag aaa aat gtt tgc ttg gtt ccc aca       1492
Pro Gly Leu Ser Gly Pro Lys Lys Lys Asn Val Cys Leu Val Pro Thr
                480                 485                 490
```

-continued

```
ctc tat aaa agt cct taaccactaa gaagttagca taataagaca tctaaaattg    1547
Leu Tyr Lys Ser Pro
            495
tcataatcat ctaattattg ttacacttct tctatcatgt cattttgaga agtgtcttat    1607
agaggtggcc acggttccgg ttccagttcg gaagcggaac cgaaccatca gttacggttc    1667
tcagcaagaa gcgaaccgtc ccgcccccc tactgtgttt gagatataaa acacataaaa    1727
taaaataaaa aaaacgctat tttttttaa aaaaa                              1762
```

<210> SEQ ID NO 2
<211> LENGTH: 496
<212> TYPE: PRT
<213> ORGANISM: Mentha spicata

<400> SEQUENCE: 2

```
Met Glu Leu Asp Leu Leu Ser Ala Ile Ile Ile Leu Val Ala Thr Tyr
 1               5                  10                  15

Ile Val Ser Leu Leu Ile Asn Gln Trp Arg Lys Ser Lys Ser Gln Gln
                20                  25                  30

Asn Leu Pro Pro Ser Pro Pro Lys Leu Pro Val Ile Gly His Leu His
            35                  40                  45

Phe Leu Trp Gly Gly Leu Pro Gln His Val Phe Arg Ser Ile Ala Gln
        50                  55                  60

Lys Tyr Gly Pro Val Ala His Val Gln Leu Gly Glu Val Tyr Ser Val
65                  70                  75                  80

Val Leu Ser Ser Ala Glu Ala Ala Lys Gln Ala Met Lys Val Leu Asp
                85                  90                  95

Pro Asn Phe Ala Asp Arg Phe Asp Gly Ile Gly Ser Arg Thr Met Trp
            100                 105                 110

Tyr Asp Lys Asp Asp Ile Ile Phe Ser Pro Tyr Asn Asp His Trp Arg
        115                 120                 125

Gln Met Arg Arg Ile Cys Val Thr Glu Leu Leu Ser Pro Lys Asn Val
    130                 135                 140

Arg Ser Phe Gly Tyr Ile Arg Gln Glu Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
            180                 185                 190

Leu Lys Asp Gln Gly Ser Leu Ala Glu Leu Val Lys Glu Ser Leu Ala
        195                 200                 205

Leu Ala Ser Gly Phe Glu Leu Ala Asp Leu Tyr Pro Ser Ser Trp Leu
    210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Glu Phe Gly Gly Glu Asp Ile Val Asp Val Leu Phe Arg
            260                 265                 270

Met Gln Lys Gly Ser Asp Ile Lys Ile Pro Ile Thr Ser Asn Cys Ile
        275                 280                 285

Lys Gly Phe Ile Phe Asp Thr Phe Ser Ala Gly Ala Glu Thr Ser Ser
    290                 295                 300

Thr Thr Ile Ser Trp Ala Leu Ser Glu Leu Met Arg Asn Pro Ala Lys
305                 310                 315                 320
```

```
Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
                355                 360                 365

Gln Ser Arg Glu Glu Cys Glu Val Asn Gly Tyr Thr Ile Pro Ala Lys
            370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
                420                 425                 430

Arg Arg Ile Cys Pro Gly Leu His Phe Gly Leu Ala Asn Val Glu Ile
                435                 440                 445

Pro Leu Ala Gln Leu Leu Tyr His Phe Asp Trp Lys Leu Pro Gln Gly
        450                 455                 460

Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
                485                 490                 495

<210> SEQ ID NO 3
<211> LENGTH: 1665
<212> TYPE: DNA
<213> ORGANISM: Mentha piperita
<220> FEATURE:
<221> NAME/KEY: CDS
<222> LOCATION: (19)..(1518)

<400> SEQUENCE: 3
agaaaataaa ataaaata atg gag ctt cag att tcg tcg gcg att ata atc      51
                   Met Glu Leu Gln Ile Ser Ser Ala Ile Ile Ile
                    1               5                   10 ctt gta gta acc tac acc ata tcc ctc cta ata atc aag caa tgg cga     99
Leu Val Val Thr Tyr Thr Ile Ser Leu Leu Ile Ile Lys Gln Trp Arg
            15                  20                  25 aaa ccg aaa ccc caa gag aac ctg cct ccg ggc ccg ccg aag ctg ccg    147
Lys Pro Lys Pro Gln Glu Asn Leu Pro Pro Gly Pro Pro Lys Leu Pro
            30                  35                  40 ctg atc ggg cac ctc cac ctc cta tgg ggg aag ctg ccg cag cac gcg    195
Leu Ile Gly His Leu His Leu Leu Trp Gly Lys Leu Pro Gln His Ala
        45                  50                  55 ctg gcc agc gtg gcg aag cag tac ggc cca gtg gcg cac gtg cag ctc    243
Leu Ala Ser Val Ala Lys Gln Tyr Gly Pro Val Ala His Val Gln Leu
60                  65                  70                  75 ggc gag gtg ttc tcc gtc gtg ctc tcg tcc cgc gag gcc acg aag gag    291
Gly Glu Val Phe Ser Val Val Leu Ser Ser Arg Glu Ala Thr Lys Glu
                80                  85                  90 gcg atg aag ctg gtg gac ccg gcc tgc gcg gac cgg ttc gag agc atc    339
Ala Met Lys Leu Val Asp Pro Ala Cys Ala Asp Arg Phe Glu Ser Ile
            95                  100                 105 ggg acg aag atc atg tgg tac gac aac gac gac atc atc ttc agc ccc    387
Gly Thr Lys Ile Met Trp Tyr Asp Asn Asp Asp Ile Ile Phe Ser Pro
        110                 115                 120 tac agc gtg cac tgg cgc cag atg cgg aag atc tgc gtc tcc gag ctc    435
Tyr Ser Val His Trp Arg Gln Met Arg Lys Ile Cys Val Ser Glu Leu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 125 |     |     |     | 130 |     |     |     |     | 135 |     |     |     |     |      |
| ctc | agc | gcc | cgc | aac | gtc | cgc | tcc | ttc | ggc | ttc | atc | agg | cag | gac | gag | 483  |
| Leu | Ser | Ala | Arg | Asn | Val | Arg | Ser | Phe | Gly | Phe | Ile | Arg | Gln | Asp | Glu |      |
| 140 |     |     |     | 145 |     |     |     |     | 150 |     |     |     |     | 155 |     |      |
| gtg | tcc | cgc | ctc | ctc | ggc | cac | ctc | cgc | tcg | gcc | gcg | gcg | ggg | gag |     | 531  |
| Val | Ser | Arg | Leu | Leu | Gly | His | Leu | Arg | Ser | Ser | Ala | Ala | Ala | Gly | Glu |      |
|     |     |     |     | 160 |     |     |     |     | 165 |     |     |     |     | 170 |     |      |
| gcc | gtg | gac | ctc | acg | gag | cgg | ata | gcg | acg | ctg | acg | tgc | tcc | atc | atc | 579  |
| Ala | Val | Asp | Leu | Thr | Glu | Arg | Ile | Ala | Thr | Leu | Thr | Cys | Ser | Ile | Ile |      |
|     |     |     | 175 |     |     |     |     | 180 |     |     |     |     | 185 |     |     |      |
| tgc | agg | gcg | gcg | ttc | ggg | agc | gtg | atc | agg | gac | cac | gag | gag | ctg | gtg | 627  |
| Cys | Arg | Ala | Ala | Phe | Gly | Ser | Val | Ile | Arg | Asp | His | Glu | Glu | Leu | Val |      |
|     |     | 190 |     |     |     |     | 195 |     |     |     |     | 200 |     |     |     |      |
| gag | ctg | gtg | aag | gac | gcc | ctc | agc | atg | gcg | tcc | ggg | ttc | gag | ctc | gcc | 675  |
| Glu | Leu | Val | Lys | Asp | Ala | Leu | Ser | Met | Ala | Ser | Gly | Phe | Glu | Leu | Ala |      |
|     | 205 |     |     |     |     | 210 |     |     |     |     | 215 |     |     |     |     |      |
| gac | atg | ttc | ccc | tcc | tcc | aag | ctc | ctc | aac | ttg | ctc | tgc | tgg | aac | aag | 723  |
| Asp | Met | Phe | Pro | Ser | Ser | Lys | Leu | Leu | Asn | Leu | Leu | Cys | Trp | Asn | Lys |      |
| 220 |     |     |     |     | 225 |     |     |     |     | 230 |     |     |     |     | 235 |      |
| agc | aag | ctg | tgg | agg | atg | cgc | cgc | cgc | gtc | gac | gcc | atc | ctc | gag | gcc | 771  |
| Ser | Lys | Leu | Trp | Arg | Met | Arg | Arg | Arg | Val | Asp | Ala | Ile | Leu | Glu | Ala |      |
|     |     |     |     | 240 |     |     |     |     | 245 |     |     |     |     | 250 |     |      |
| atc | gtg | gag | gag | cac | aag | ctc | aag | aag | agc | ggc | gag | ttt | ggc | ggc | gag | 819  |
| Ile | Val | Glu | Glu | His | Lys | Leu | Lys | Lys | Ser | Gly | Glu | Phe | Gly | Gly | Glu |      |
|     |     |     | 255 |     |     |     |     | 260 |     |     |     |     | 265 |     |     |      |
| gac | att | att | gac | gta | ctc | ttt | agg | atg | cag | aag | gat | agc | cag | atc | aaa | 867  |
| Asp | Ile | Ile | Asp | Val | Leu | Phe | Arg | Met | Gln | Lys | Asp | Ser | Gln | Ile | Lys |      |
|     |     | 270 |     |     |     |     | 275 |     |     |     |     | 280 |     |     |     |      |
| gtc | ccc | atc | acc | acc | aac | gcc | atc | aaa | gcc | ttc | atc | ttc | gac | acg | ttc | 915  |
| Val | Pro | Ile | Thr | Thr | Asn | Ala | Ile | Lys | Ala | Phe | Ile | Phe | Asp | Thr | Phe |      |
|     | 285 |     |     |     |     | 290 |     |     |     |     | 295 |     |     |     |     |      |
| tca | gcg | ggg | acc | gag | aca | tca | tca | acc | acc | acc | ctg | tgg | gtg | atg | gcg | 963  |
| Ser | Ala | Gly | Thr | Glu | Thr | Ser | Ser | Thr | Thr | Thr | Leu | Trp | Val | Met | Ala |      |
| 300 |     |     |     |     | 305 |     |     |     |     | 310 |     |     |     |     | 315 |      |
| gag | ctg | atg | agg | aat | cca | gag | gtg | atg | gcg | aaa | gcg | cag | gcg | gag | gtg | 1011 |
| Glu | Leu | Met | Arg | Asn | Pro | Glu | Val | Met | Ala | Lys | Ala | Gln | Ala | Glu | Val |      |
|     |     |     |     | 320 |     |     |     |     | 325 |     |     |     |     | 330 |     |      |
| aga | gcg | gcg | ctg | aag | ggg | aag | acg | gac | tgg | gac | gtg | gac | gac | gtg | cag | 1059 |
| Arg | Ala | Ala | Leu | Lys | Gly | Lys | Thr | Asp | Trp | Asp | Val | Asp | Asp | Val | Gln |      |
|     |     |     | 335 |     |     |     |     | 340 |     |     |     |     | 345 |     |     |      |
| gag | ctt | aag | tac | atg | aaa | tcg | gtg | gtg | aag | gag | acg | atg | agg | atg | cac | 1107 |
| Glu | Leu | Lys | Tyr | Met | Lys | Ser | Val | Val | Lys | Glu | Thr | Met | Arg | Met | His |      |
|     |     | 350 |     |     |     |     | 355 |     |     |     |     | 360 |     |     |     |      |
| cct | ccg | atc | ccg | ttg | atc | ccg | aga | tca | tgc | aga | gaa | gaa | tgc | gag | gtc | 1155 |
| Pro | Pro | Ile | Pro | Leu | Ile | Pro | Arg | Ser | Cys | Arg | Glu | Glu | Cys | Glu | Val |      |
|     | 365 |     |     |     |     | 370 |     |     |     |     | 375 |     |     |     |     |      |
| aac | ggg | tac | acg | att | ccg | aat | aag | gcc | aga | atc | atg | atc | aac | gtg | tgg | 1203 |
| Asn | Gly | Tyr | Thr | Ile | Pro | Asn | Lys | Ala | Arg | Ile | Met | Ile | Asn | Val | Trp |      |
| 380 |     |     |     |     | 385 |     |     |     |     | 390 |     |     |     |     | 395 |      |
| tcc | atg | ggt | agg | aat | cct | ctc | tac | tgg | gaa | aaa | ccc | gag | acc | ttt | tgg | 1251 |
| Ser | Met | Gly | Arg | Asn | Pro | Leu | Tyr | Trp | Glu | Lys | Pro | Glu | Thr | Phe | Trp |      |
|     |     |     |     | 400 |     |     |     |     | 405 |     |     |     |     | 410 |     |      |
| ccc | gaa | agg | ttt | gac | caa | gtc | tcg | agg | gat | ttc | atg | gga | aac | gat | ttc | 1299 |
| Pro | Glu | Arg | Phe | Asp | Gln | Val | Ser | Arg | Asp | Phe | Met | Gly | Asn | Asp | Phe |      |
|     |     |     | 415 |     |     |     |     | 420 |     |     |     |     | 425 |     |     |      |
| gag | ttc | atc | cca | ttt | gga | gct | gga | aga | aga | atc | tgc | ccc | ggt | ttg | aat | 1347 |
| Glu | Phe | Ile | Pro | Phe | Gly | Ala | Gly | Arg | Arg | Ile | Cys | Pro | Gly | Leu | Asn |      |
|     |     | 430 |     |     |     |     | 435 |     |     |     |     | 440 |     |     |     |      |
| ttc | ggg | ttg | gca | aat | gtt | gag | gtc | cca | ttg | gca | cag | ctt | ctt | tac | cac | 1395 |

```
                                                                    -continued Phe Gly Leu Ala Asn Val Glu Val Pro Leu Ala Gln Leu Leu Tyr His
            445                 450                 455 ttc gac tgg aag ttg gcg gaa gga atg aac cct tcc gat atg gac atg    1443
Phe Asp Trp Lys Leu Ala Glu Gly Met Asn Pro Ser Asp Met Asp Met
460                 465                 470                 475 tct gag gca gaa ggc ctt acc gga ata aga aag aac aat ctt cta ctc    1491
Ser Glu Ala Glu Gly Leu Thr Gly Ile Arg Lys Asn Asn Leu Leu Leu
                480                 485                 490 gtt ccc aca ccc tac gat cct tcc tca tgatcaatta atactcttta          1538
Val Pro Thr Pro Tyr Asp Pro Ser Ser
                495                 500 atttgctcct ttgaataaag agtgcatata catatatgat atatacacat acacacacat   1598
atactatata tgtatatgta gctttgggct atgaatatag aaattatgta aaaaaataa    1658 aaaggaa                                                             1665

<210> SEQ ID NO 4
<211> LENGTH: 500
<212> TYPE: PRT
<213> ORGANISM: Mentha piperita

<400> SEQUENCE: 4

Met Glu Leu Gln Ile Ser Ser Ala Ile Ile Leu Val Val Thr Tyr
  1               5                  10                  15

Thr Ile Ser Leu Leu Ile Ile Lys Gln Trp Arg Lys Pro Lys Pro Gln
                 20                  25                  30

Glu Asn Leu Pro Pro Gly Pro Pro Lys Leu Pro Leu Ile Gly His Leu
             35                  40                  45

His Leu Leu Trp Gly Lys Leu Pro Gln His Ala Leu Ala Ser Val Ala
         50                  55                  60

Lys Gln Tyr Gly Pro Val Ala His Val Gln Leu Gly Glu Val Phe Ser
     65                  70                  75                  80

Val Val Leu Ser Ser Arg Glu Ala Thr Lys Glu Ala Met Lys Leu Val
                 85                  90                  95

Asp Pro Ala Cys Ala Asp Arg Phe Glu Ser Ile Gly Thr Lys Ile Met
            100                 105                 110

Trp Tyr Asp Asn Asp Asp Ile Ile Phe Ser Pro Tyr Ser Val His Trp
        115                 120                 125

Arg Gln Met Arg Lys Ile Cys Val Ser Glu Leu Leu Ser Ala Arg Asn
    130                 135                 140

Val Arg Ser Phe Gly Phe Ile Arg Gln Asp Glu Val Ser Arg Leu Leu
145                 150                 155                 160

Gly His Leu Arg Ser Ser Ala Ala Gly Glu Ala Val Asp Leu Thr
                165                 170                 175

Glu Arg Ile Ala Thr Leu Thr Cys Ser Ile Ile Cys Arg Ala Ala Phe
            180                 185                 190

Gly Ser Val Ile Arg Asp His Glu Glu Leu Val Glu Leu Val Lys Asp
        195                 200                 205

Ala Leu Ser Met Ala Ser Gly Phe Glu Leu Ala Asp Met Phe Pro Ser
    210                 215                 220

Ser Lys Leu Leu Asn Leu Leu Cys Trp Asn Lys Ser Lys Leu Trp Arg
225                 230                 235                 240

Met Arg Arg Arg Val Asp Ala Ile Leu Glu Ala Ile Val Glu Glu His
                245                 250                 255

Lys Leu Lys Lys Ser Gly Glu Phe Gly Gly Glu Asp Ile Ile Asp Val
            260                 265                 270
```

```
Leu Phe Arg Met Gln Lys Asp Ser Gln Ile Lys Val Pro Ile Thr Thr
            275                 280                 285

Asn Ala Ile Lys Ala Phe Ile Phe Asp Thr Phe Ser Ala Gly Thr Glu
            290                 295                 300

Thr Ser Ser Thr Thr Thr Leu Trp Val Met Ala Glu Leu Met Arg Asn
305                 310                 315                 320

Pro Glu Val Met Ala Lys Ala Gln Ala Glu Val Arg Ala Ala Leu Lys
                325                 330                 335

Gly Lys Thr Asp Trp Asp Val Asp Val Gln Glu Leu Lys Tyr Met
                340                 345                 350

Lys Ser Val Val Lys Glu Thr Met Arg Met His Pro Pro Ile Pro Leu
                355                 360                 365

Ile Pro Arg Ser Cys Arg Glu Glu Cys Glu Val Asn Gly Tyr Thr Ile
            370                 375                 380

Pro Asn Lys Ala Arg Ile Met Ile Asn Val Trp Ser Met Gly Arg Asn
385                 390                 395                 400

Pro Leu Tyr Trp Glu Lys Pro Glu Thr Phe Trp Pro Glu Arg Phe Asp
                405                 410                 415

Gln Val Ser Arg Asp Phe Met Gly Asn Asp Phe Glu Phe Ile Pro Phe
                420                 425                 430

Gly Ala Gly Arg Arg Ile Cys Pro Gly Leu Asn Phe Gly Leu Ala Asn
            435                 440                 445

Val Glu Val Pro Leu Ala Gln Leu Leu Tyr His Phe Asp Trp Lys Leu
            450                 455                 460

Ala Glu Gly Met Asn Pro Ser Asp Met Asp Met Ser Glu Ala Glu Gly
465                 470                 475                 480

Leu Thr Gly Ile Arg Lys Asn Asn Leu Leu Leu Val Pro Thr Pro Tyr
                485                 490                 495

Asp Pro Ser Ser
            500

<210> SEQ ID NO 5
<211> LENGTH: 1515
<212> TYPE: DNA
<213> ORGANISM: Mentha piperita
<220> FEATURE:
<221> NAME/KEY: CDS
<222> LOCATION: (1)..(1494)

<400> SEQUENCE: 5 atg gag ctc ctc cag ctt tgg tcg gcg ctt ata atc ctc gta gta acc      48
Met Glu Leu Leu Gln Leu Trp Ser Ala Leu Ile Ile Leu Val Val Thr
1               5                   10                  15 tac acc ata tcc ctc cta atc aac caa tgg cga aaa ccg aaa ccc caa      96
Tyr Thr Ile Ser Leu Leu Ile Asn Gln Trp Arg Lys Pro Lys Pro Gln
                20                  25                  30 ggg aag ttc ccc ccg ggc ccg ccg agg ctg ccg ctg atc ggg cac ctc     144
Gly Lys Phe Pro Pro Gly Pro Pro Arg Leu Pro Leu Ile Gly His Leu
            35                  40                  45 cac ctc ctg tgg ggg aag ctg ccg cag cac gcg ctg gcc agc gtg gcg     192
His Leu Leu Trp Gly Lys Leu Pro Gln His Ala Leu Ala Ser Val Ala
        50                  55                  60 aag gag tac ggc ccc gtg gcc cac gtg cag ctg ggt gag gtg ttc tcc     240
Lys Glu Tyr Gly Pro Val Ala His Val Gln Leu Gly Glu Val Phe Ser
65                  70                  75                  80 gtc gtc ctt tcg tcg cgg gag gcg acg aag gag gcg atg aag ctg gta     288
Val Val Leu Ser Ser Arg Glu Ala Thr Lys Glu Ala Met Lys Leu Val
```

```
                     85                    90                    95
gac ccg gcg tgc gcg aac cgg ttc gag agc atc ggg acg agg atc atg       336
Asp Pro Ala Cys Ala Asn Arg Phe Glu Ser Ile Gly Thr Arg Ile Met
            100                 105                 110 tgg tac gac aac gag gac atc atc ttc agc ccc tac agc gag cac tgg       384
Trp Tyr Asp Asn Glu Asp Ile Ile Phe Ser Pro Tyr Ser Glu His Trp
            115                 120                 125 cgc cag atg cgc aag atc tgc gtc tcc gag ctc ctc tcc tcc cgc aac       432
Arg Gln Met Arg Lys Ile Cys Val Ser Glu Leu Leu Ser Ser Arg Asn
        130                 135                 140 gtc cgc tcc ttc ggc ttc atc cgg cag gac gag gtg tcg cgc ctc ctc       480
Val Arg Ser Phe Gly Phe Ile Arg Gln Asp Glu Val Ser Arg Leu Leu
145                 150                 155                 160 cgc cac ctc cgc tcy tcg gca ggg gcg gcc gtg gac atg acg gag agg       528
Arg His Leu Arg Xaa Ser Ala Gly Ala Ala Val Asp Met Thr Glu Arg
                165                 170                 175 ata gag acg ctg acg tgc tcc atc atc tgc agg gcg gcg ttc ggg agc       576
Ile Glu Thr Leu Thr Cys Ser Ile Ile Cys Arg Ala Ala Phe Gly Ser
            180                 185                 190 gtg atc agg gac aac gcg gag ctg gtg ggg ctg gtc aag gac gcg ctc       624
Val Ile Arg Asp Asn Ala Glu Leu Val Gly Leu Val Lys Asp Ala Leu
        195                 200                 205 agc atg gcc tcg ggg ttc gag ctc gcc gac atg ttc ccc tcc tcc aag       672
Ser Met Ala Ser Gly Phe Glu Leu Ala Asp Met Phe Pro Ser Ser Lys
        210                 215                 220 ctc ctc aac ctc ctc tgc tgg aac aag agc aag ctc tgg agg atg cgc       720
Leu Leu Asn Leu Leu Cys Trp Asn Lys Ser Lys Leu Trp Arg Met Arg
225                 230                 235                 240 cgc cgc gtc gac acc atc ctc gag gcc atc gtc gac gag cac aag ttc       768
Arg Arg Val Asp Thr Ile Leu Glu Ala Ile Val Asp Glu His Lys Phe
                245                 250                 255 aag aag agc ggc gag ttc ggc ggc gag gac atc atc gac gtc ctc ttc       816
Lys Lys Ser Gly Glu Phe Gly Gly Glu Asp Ile Ile Asp Val Leu Phe
            260                 265                 270 agg atg cag aag gcc acc cag atc aaa gtc ccc atc acc acc aac tcc       864
Arg Met Gln Lys Ala Thr Gln Ile Lys Val Pro Ile Thr Thr Asn Ser
        275                 280                 285 atc aaa gcc ttc atc ttc gat acg ttc tca gca ggg act gag aca tcc       912
Ile Lys Ala Phe Ile Phe Asp Thr Phe Ser Ala Gly Thr Glu Thr Ser
        290                 295                 300 tca acc acc acc cta tgg gtg ctg gcg gag ctg atg agg aac ccg gca       960
Ser Thr Thr Thr Leu Trp Val Leu Ala Glu Leu Met Arg Asn Pro Ala
305                 310                 315                 320 gtg atg gcg aaa gcg cag gcg gag gtg aga gcg gca ctg aag gag aag      1008
Val Met Ala Lys Ala Gln Ala Glu Val Arg Ala Ala Leu Lys Glu Lys
                325                 330                 335 acg aac tgg gac gtg gat gat gtg caa gag ctt aag tac atg aaa tcg      1056
Thr Asn Trp Asp Val Asp Asp Val Gln Glu Leu Lys Tyr Met Lys Ser
            340                 345                 350 gtg gtg aag gag acg atg agg atg cac cct ccg atc ccg ttg atc ccg      1104
Val Val Lys Glu Thr Met Arg Met His Pro Pro Ile Pro Leu Ile Pro
        355                 360                 365 aga tca tgc aga gaa gaa tgc gtg gtt aac ggg tat acg att ccg aac      1152
Arg Ser Cys Arg Glu Glu Cys Val Val Asn Gly Tyr Thr Ile Pro Asn
        370                 375                 380 aag gcc aga atc atg atc aac gtc tgg tcc atg ggc agg aat cct ctc      1200
Lys Ala Arg Ile Met Ile Asn Val Trp Ser Met Gly Arg Asn Pro Leu
385                 390                 395                 400 tac tgg gaa aaa ccc gat acc ttt tgg ccc gaa agg ttt gac caa gtt      1248
```

|  |  |  |  |  |  |  |  |  |  |  |  |  |
|---|---|---|---|---|---|---|---|---|---|---|---|---|
| Tyr | Trp | Glu | Lys 405 | Pro | Asp | Thr | Phe | Trp 410 | Pro | Glu | Arg | Phe | Asp | Gln 415 | Val |

```
tca aag gat ttc atg gga aat gat ttc gag ttc gtc ccg ttc gga gcg     1296
Ser Lys Asp Phe Met Gly Asn Asp Phe Glu Phe Val Pro Phe Gly Ala
        420                 425                 430 gga aga aga atc tgc ccc ggc ttg aac ttc ggg tcg gca aac gtt gag     1344
Gly Arg Arg Ile Cys Pro Gly Leu Asn Phe Gly Ser Ala Asn Val Glu
        435                 440                 445 gtt cca ttg gcg cag ctt ctt tac cac ttc gac tgg aag ttg gcg gaa     1392
Val Pro Leu Ala Gln Leu Leu Tyr His Phe Asp Trp Lys Leu Ala Glu
450                 455                 460 gga atg aaa cct tct gat atg gac atg tct gag gcg gaa ggc ctt acc     1440
Gly Met Lys Pro Ser Asp Met Asp Met Ser Glu Ala Glu Gly Leu Thr
465                 470                 475                 480 gga ata cta aag aac aat ctt ctt ctt gtt ccc aca ccc tac gat cct     1488
Gly Ile Leu Lys Asn Asn Leu Leu Leu Val Pro Thr Pro Tyr Asp Pro
                485                 490                 495 tcc tca tgatcaatca tcttttgctc c                                     1515
Ser Ser
```

<210> SEQ ID NO 6
<211> LENGTH: 498
<212> TYPE: PRT
<213> ORGANISM: Mentha piperita

<400> SEQUENCE: 6

```
Met Glu Leu Leu Gln Leu Trp Ser Ala Leu Ile Ile Leu Val Val Thr
 1               5                  10                  15

Tyr Thr Ile Ser Leu Leu Ile Asn Gln Trp Arg Lys Pro Lys Pro Gln
                20                  25                  30

Gly Lys Phe Pro Pro Gly Pro Pro Arg Leu Pro Leu Ile Gly His Leu
            35                  40                  45

His Leu Leu Trp Gly Lys Leu Pro Gln His Ala Leu Ala Ser Val Ala
        50                  55                  60

Lys Glu Tyr Gly Pro Val Ala His Val Gln Leu Gly Glu Val Phe Ser
 65                  70                  75                  80

Val Val Leu Ser Ser Arg Glu Ala Thr Lys Glu Ala Met Lys Leu Val
                85                  90                  95

Asp Pro Ala Cys Ala Asn Arg Phe Glu Ser Ile Gly Thr Arg Ile Met
            100                 105                 110

Trp Tyr Asp Asn Glu Asp Ile Ile Phe Ser Pro Tyr Ser Glu His Trp
        115                 120                 125

Arg Gln Met Arg Lys Ile Cys Val Ser Glu Leu Leu Ser Ser Arg Asn
    130                 135                 140

Val Arg Ser Phe Gly Phe Ile Arg Gln Asp Glu Val Ser Arg Leu Leu
145                 150                 155                 160

Arg His Leu Arg Xaa Ser Ala Gly Ala Ala Val Asp Met Thr Glu Arg
                165                 170                 175

Ile Glu Thr Leu Thr Cys Ser Ile Ile Cys Arg Ala Ala Phe Gly Ser
            180                 185                 190

Val Ile Arg Asp Asn Ala Glu Leu Val Gly Leu Val Lys Asp Ala Leu
        195                 200                 205

Ser Met Ala Ser Gly Phe Glu Leu Ala Asp Met Phe Pro Ser Ser Lys
    210                 215                 220

Leu Leu Asn Leu Leu Cys Trp Asn Lys Ser Lys Leu Trp Arg Met Arg
225                 230                 235                 240
```

```
                                 -continued

Arg Arg Val Asp Thr Ile Leu Glu Ala Ile Val Asp Glu His Lys Phe
                245                 250                 255

Lys Lys Ser Gly Glu Phe Gly Gly Asp Ile Ile Asp Val Leu Phe
            260                 265                 270

Arg Met Gln Lys Ala Thr Gln Ile Lys Val Pro Ile Thr Thr Asn Ser
            275                 280                 285

Ile Lys Ala Phe Ile Phe Asp Thr Phe Ser Ala Gly Thr Glu Thr Ser
        290                 295                 300

Ser Thr Thr Thr Leu Trp Val Leu Ala Glu Leu Met Arg Asn Pro Ala
305                 310                 315                 320

Val Met Ala Lys Ala Gln Ala Glu Val Arg Ala Ala Leu Lys Glu Lys
                325                 330                 335

Thr Asn Trp Asp Val Asp Asp Val Gln Glu Leu Lys Tyr Met Lys Ser
                340                 345                 350

Val Val Lys Glu Thr Met Arg Met His Pro Pro Ile Pro Leu Ile Pro
            355                 360                 365

Arg Ser Cys Arg Glu Glu Cys Val Val Asn Gly Tyr Thr Ile Pro Asn
        370                 375                 380

Lys Ala Arg Ile Met Ile Asn Val Trp Ser Met Gly Arg Asn Pro Leu
385                 390                 395                 400

Tyr Trp Glu Lys Pro Asp Thr Phe Trp Pro Glu Arg Phe Asp Gln Val
                405                 410                 415

Ser Lys Asp Phe Met Gly Asn Asp Phe Glu Phe Val Pro Phe Gly Ala
            420                 425                 430

Gly Arg Arg Ile Cys Pro Gly Leu Asn Phe Gly Ser Ala Asn Val Glu
        435                 440                 445

Val Pro Leu Ala Gln Leu Leu Tyr His Phe Asp Trp Lys Leu Ala Glu
    450                 455                 460

Gly Met Lys Pro Ser Asp Met Asp Met Ser Glu Ala Glu Gly Leu Thr
465                 470                 475                 480

Gly Ile Leu Lys Asn Asn Leu Leu Val Pro Thr Pro Tyr Asp Pro
                485                 490                 495

Ser Ser

<210> SEQ ID NO 7
<211> LENGTH: 21
<212> TYPE: PRT
<213> ORGANISM: Mentha spicata

<400> SEQUENCE: 7

Met Glu Leu Asp Leu Leu Ser Ala Ile Ile Leu Val Ala Thr Tyr
1               5                   10                  15

Ile Val Ser Leu Leu
            20

<210> SEQ ID NO 8
<211> LENGTH: 24
<212> TYPE: PRT
<213> ORGANISM: Mentha spicata

<400> SEQUENCE: 8

Glu Val Asn Gly Tyr Thr Ile Pro Ala Lys Thr Arg Ile Phe Ile Asn
1               5                   10                  15

Val Trp Ala Ile Gly Arg Asp Pro
            20
```

```
<210> SEQ ID NO 9
<211> LENGTH: 25
<212> TYPE: PRT
<213> ORGANISM: Mentha spicata

<400> SEQUENCE: 9

Val Ser Lys Met Ser Cys Val Val Cys Arg Ala Ala Phe Gly Ser
 1               5                  10                  15

Val Leu Lys Asp Gln Gly Ser Leu Ala
            20                  25

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: primer 1.AC
<220> FEATURE:
<221> NAME/KEY: misc_feature
<222> LOCATION: (1)..(14)
<223> OTHER INFORMATION: Oligonucleotide primer designed against 5' end
      of fragment V-8.1

<400> SEQUENCE: 10
gtnwsnaara tgwc                                                        14

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: primer 1.AG
<220> FEATURE:
<221> NAME/KEY: misc_feature
<222> LOCATION: (1)..(14)
<223> OTHER INFORMATION: Oligonucleotide primer used to clone
      limonene-6-hydroxylase wherein n at positions 3
      and 6 represent I

<400> SEQUENCE: 11
gtnwsnaara tgwg                                                        14

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: primer 1.B
<220> FEATURE:
<221> NAME/KEY: misc_feature
<222> LOCATION: (1)..(20)
<223> OTHER INFORMATION: Oligonucleotide primer used to clone
      limonene-6-hydroxylase wherein n at positions 6
      and 9 represent I

<400> SEQUENCE: 12
gcytcnswnc cytgrtcytt                                                  20

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: primer 1.C
<220> FEATURE:
<221> NAME/KEY: misc_feature
<222> LOCATION: (1)..(20)
<223> OTHER INFORMATION: Oligonucleotide primer designed against central
      region of V-8.1 peptide
```

-continued

<400> SEQUENCE: 13
gtgtgtcgtc gtgtgcaggg cggcgttcg                                29

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: primer 2.AA
<220> FEATURE:
<221> NAME/KEY: misc_feature
<222> LOCATION: (1)..(19)
<223> OTHER INFORMATION: Oligonucleotide primer 2.AA designed against
      amino terminus of V-8.2 peptide wherein n at positions
      9, 15 and 18 represents I, G or A

<400> SEQUENCE: 14
atggarytng ayytnytna                                           19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: primer 2.AT
<220> FEATURE:
<221> NAME/KEY: misc_feature
<222> LOCATION: (1)..(19)
<223> OTHER INFORMATION: oligonucleotide primer used to clone
      limonene-6-hydroxylase wherein n at positions 9,
      15 and 18 represents I, G, or A

<400> SEQUENCE: 15
atggarytng ayytnytnt                                           19

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: primer 2.B
<220> FEATURE:
<221> NAME/KEY: misc_feature
<222> LOCATION: (1)..(17)
<223> OTHER INFORMATION: Oligonucleotide primer designed against 3' end
      of V-8.2 peptide wherein n at positions 3, 9, 12 and
      15 represents I

<400> SEQUENCE: 16
tcnatrtang tngcnac                                             17

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: primer 3.A
<220> FEATURE:
<221> NAME/KEY: misc_feature
<222> LOCATION: (1)..(20)
<223> OTHER INFORMATION: Oligonucleotide primer designed against 5' end
      of V-8.3 peptide wherein n at positions 9, and 15
      represents I

<400> SEQUENCE: 17
atggargtna ayggntayac                                          20

<210> SEQ ID NO 18
<211> LENGTH: 19

```
<212> TYPE: DNA
<213> ORGANISM: Artificial Sequence
<220> FEATURE:
<223> OTHER INFORMATION: Description of Artificial Sequence: primer 3.B
<220> FEATURE:
<221> NAME/KEY: misc_feature
<222> LOCATION: (1)..(19)
<223> OTHER INFORMATION: Oligonucleotide primer that primes the polyA
      tail on cDNA molecules

<400> SEQUENCE: 18
tttttttttt tttttttth                                                 19

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: primer 3.C
<220> FEATURE:
<221> NAME/KEY: misc_feature
<222> LOCATION: (1)..(41)
<223> OTHER INFORMATION: Primer designed to 3' end of peptide V-8.3
      wherein n at positions 6, 12, 18, 27, 30 36 and 39
      represents I

<400> SEQUENCE: 19
ccdatngcda tnacrttnat raadatnckn gtyttngcng g                        41

<210> SEQ ID NO 20
<211> LENGTH: 655
<212> TYPE: DNA
<213> ORGANISM: Mentha spicata

<400> SEQUENCE: 20
cgtgtgtcgt cgtgtgcagg gcggcgttcg ggagtgtgct caaggaccag ggttcgttgg     60
cggagttggt gaaggagtcg ctggcattgg cgtccgggtt tgagctggcg gatctctacc   120
cttcctcatg gctcctcaac ctgcttagct tgaacaagta caggttgcag aggatgcgcc   180
gccgcctcga tcacatcctt gatgggttcc tggaggagca tagggagaag aagagcggcg   240
agttgtgagg cgaggacatc gtcgacgttc ttttcaggat gcagaagggc agcgacatca   300
aaattcccat tacttccaat tgcatcaagg gtttcatttt cgacaccttc tccgcgggag   360
ctgaaacgtc ttcgacgacc atctcatggg cgttgtcgga actgatgagg aatccggcga   420
agatggccaa ggtgcaggcg gaggtaagag aggcgctcaa gggaaagaca gtcgtggatt   480
tgagcgaggt gcaagagcta aaatacctga gatcggtgtt aaaggagact ctgaggctgc   540 accctcccctt tccattaatc ccaagacaat ccagggaaga atgcgaggtt aacgggtaca   600
cgattccggc caaaactaga atcttcatca acgtctgggc tatcggaagg gatcc        655

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: primer
      22CR3
<220> FEATURE:
<221> NAME/KEY: misc_feature
<222> LOCATION: (1)..(24)
<223> OTHER INFORMATION: Sequencing primer

<400> SEQUENCE: 21
cacgacatct tcgacacctc ctcc                                           24
```

```
<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: primer
      22CF1
<220> FEATURE:
<221> NAME/KEY: misc_feature
<222> LOCATION: (1)..(22)
<223> OTHER INFORMATION: Sequencing primer

<400> SEQUENCE: 22
gcaacctaca tcgtatccct cc                                              22

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: primer
      NTREV1
<220> FEATURE:
<221> NAME/KEY: misc_feature
<222> LOCATION: (1)..(24)
<223> OTHER INFORMATION: sequencing primer

<400> SEQUENCE: 23
ggctcggagg taggttttgt tggg                                            24

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: primer
      NTREV2
<220> FEATURE:
<221> NAME/KEY: misc_feature
<222> LOCATION: (1)..(27)
<223> OTHER INFORMATION: sequencing primer

<400> SEQUENCE: 24
gattaggagg gatacgatgt aggttgc                                         27

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence:
      primer
      11A4.25R6
<220> FEATURE:
<221> NAME/KEY: misc_feature
<222> LOCATION: (1)..(22)
<223> OTHER INFORMATION: sequencing primer

<400> SEQUENCE: 25
ctgggctcag cagctctgtc aa                                              22

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: primer
      4.25R5
<220> FEATURE:
<221> NAME/KEY: misc_feature
```

```
<222> LOCATION: (1)..(18)
<223> OTHER INFORMATION: sequencing primer

<400> SEQUENCE: 26
gggctcagca gctctctc                                                 18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: primer
      4.25R3
<220> FEATURE:
<221> NAME/KEY: misc_feature
<222> LOCATION: (1)..(20)
<223> OTHER INFORMATION: sequencing primer

<400> SEQUENCE: 27
cttcaccaac tccgccaacg                                               20

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence:
      primer
      11A4.25R2
<220> FEATURE:
<221> NAME/KEY: misc_feature
<222> LOCATION: (1)..(19)
<223> OTHER INFORMATION: sequencing primer

<400> SEQUENCE: 28
gctcttcttc tccctatgc                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence:
      primer
      11A4.25R
<220> FEATURE:
<221> NAME/KEY: misc_feature
<222> LOCATION: (1)..(19)
<223> OTHER INFORMATION: sequencing primer

<400> SEQUENCE: 29
tagctcttgc acctcgctc                                                19

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: primer
      11A1f4
<220> FEATURE:
<221> NAME/KEY: misc_feature
<222> LOCATION: (1)..(25)
<223> OTHER INFORMATION: sequencing primer

<400> SEQUENCE: 30
ttcgggagtg tgctcaagga ccagg                                         25

<210> SEQ ID NO 31
```

```
<211> LENGTH: 20
<212> TYPE: DNA
<213> ORGANISM: Artificial Sequence
<220> FEATURE:
<223> OTHER INFORMATION: Description of Artificial Sequence: primer
      11A1F3
<220> FEATURE:
<221> NAME/KEY: misc_feature
<222> LOCATION: (1)..(20)
<223> OTHER INFORMATION: sequencing primer

<400> SEQUENCE: 31
gttggtgaag gagttcgctg                                                    20

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: primer
      11a1f2
<220> FEATURE:
<221> NAME/KEY: misc_feature
<222> LOCATION: (1)..(17)
<223> OTHER INFORMATION: sequencing primer

<400> SEQUENCE: 32
cttacaacga tcactgg                                                       17

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:
      primer
      S12.2PF1
<220> FEATURE:
<221> NAME/KEY: misc_feature
<222> LOCATION: (1)..(24)
<223> OTHER INFORMATION: sequencing primer

<400> SEQUENCE: 33
gacatcgtcg acgttctttt cagg                                               24

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence:
      primer
      S12.2PF2
<220> FEATURE:
<221> NAME/KEY: misc_feature
<222> LOCATION: (1)..(23)
<223> OTHER INFORMATION: sequencing primer

<400> SEQUENCE: 34
ctaccacttc gactggaaat tgc                                                23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence:
      primer
      S12.2PF3
<220> FEATURE:
<221> NAME/KEY: misc_feature
```

```
<222> LOCATION: (1)..(23)
<223> OTHER INFORMATION: sequencing primer

<400> SEQUENCE: 35
ctgagatcgg tgttaaagga gac                                               23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence:
      primer
      S12.2PR1
<220> FEATURE:
<221> NAME/KEY: misc_feature
<222> LOCATION: (1)..(23)
<223> OTHER INFORMATION: sequencing primer

<400> SEQUENCE: 36
gccacctcta taagacactc ctc                                               23

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence:
      primer
      S12-2PR2
<220> FEATURE:
<221> NAME/KEY: misc_feature
<222> LOCATION: (1)..(19)
<223> OTHER INFORMATION: sequencing primer

<400> SEQUENCE: 37
gatctcaaca tttgccagc                                                    19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: primer
      S12BF
<220> FEATURE:
<221> NAME/KEY: misc_feature
<222> LOCATION: (1)..(19)
<223> OTHER INFORMATION: sequencing primer

<400> SEQUENCE: 38
gaaaccatgg agctcgacc                                                    19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: primer P
      17.1F2
<220> FEATURE:
<221> NAME/KEY: misc_feature
<222> LOCATION: (1)..(19)
<223> OTHER INFORMATION: sequencing primer

<400> SEQUENCE: 39
cgacgacatc atcttcagc                                                    19

<210> SEQ ID NO 40
```

```
<211> LENGTH: 24
<212> TYPE: DNA
<213> ORGANISM: Artificial Sequence
<220> FEATURE:
<223> OTHER INFORMATION: Description of Artificial Sequence: primer
      P17.F1
<220> FEATURE:
<221> NAME/KEY: misc_feature
<222> LOCATION: (1)..(24)
<223> OTHER INFORMATION: sequencing primer

<400> SEQUENCE: 40
agtacggtcc agtggtgcac gtgc                                           24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      primer
      P17.1.2F3
<220> FEATURE:
<221> NAME/KEY: misc_feature
<222> LOCATION: (1)..(24)
<223> OTHER INFORMATION: sequencing primer

<400> SEQUENCE: 41
gaggagctgg tggagctggt gaag                                           24

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence:
      primer
      P17.1.2F5
<220> FEATURE:
<221> NAME/KEY: misc_feature
<222> LOCATION: (1)..(23)
<223> OTHER INFORMATION: sequencing primer

<400> SEQUENCE: 42
cgagatcatg cagagaagaa tgc                                            23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: primer
      P17R1
<220> FEATURE:
<221> NAME/KEY: misc_feature
<222> LOCATION: (1)..(23)
<223> OTHER INFORMATION: sequencing primer

<400> SEQUENCE: 43
atgggacctc aacatttggc aac                                            23

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: primer P
      17.1R2
<220> FEATURE:
<221> NAME/KEY: misc_feature
<222> LOCATION: (1)..(19)
```

<223> OTHER INFORMATION: sequencing primer

<400> SEQUENCE: 44
atgttcttgg ccttattcg                                            19

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence:
      primer
      P17.1.2R4
<220> FEATURE:
<221> NAME/KEY: misc_feature
<222> LOCATION: (1)..(25)
<223> OTHER INFORMATION: sequencing primer

<400> SEQUENCE: 45
cagagcaagt tgaggagctt ggagg                                     25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence:
      primer
      P17.1.2F4
<220> FEATURE:
<221> NAME/KEY: misc_feature
<222> LOCATION: (1)..(25)
<223> OTHER INFORMATION: sequencing primer

<400> SEQUENCE: 46
ccatcaccac caacgccatc aaagc                                     25

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      primer
      P17.1.2R6
<220> FEATURE:
<221> NAME/KEY: misc_feature
<222> LOCATION: (1)..(20)
<223> OTHER INFORMATION: sequencing primer

<400> SEQUENCE: 47
gtactgcttc gccacgctgg                                           20

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: primer
      BLUT3
<220> FEATURE:
<221> NAME/KEY: misc_feature
<222> LOCATION: (1)..(25)
<223> OTHER INFORMATION: sequencing primer

<400> SEQUENCE: 48
cgcgcaatta accctcacta aaggg                                     25

<210> SEQ ID NO 49

```
<211> LENGTH: 16
<212> TYPE: DNA
<213> ORGANISM: Artificial Sequence
<220> FEATURE:
<223> OTHER INFORMATION: Description of Artificial Sequence:
      primer
      11A4.10F
<220> FEATURE:
<221> NAME/KEY: misc_feature
<222> LOCATION: (1)..(16)
<223> OTHER INFORMATION: sequencing primer

<400> SEQUENCE: 49
gctgaatggg caatgg                                                     16

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:
      primer
      11A.1F-A
<220> FEATURE:
<221> NAME/KEY: misc_feature
<222> LOCATION: (1)..(18)
<223> OTHER INFORMATION: sequencing primer

<400> SEQUENCE: 50
cacctccact tcctgtgg                                                   18

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence:
      primer
      P17.1.2R5
<220> FEATURE:
<221> NAME/KEY: misc_feature
<222> LOCATION: (1)..(25)
<223> OTHER INFORMATION: sequencing primer

<400> SEQUENCE: 51
gctgaagagc tcggagacgc agatc                                           25

<210> SEQ ID NO 52
<211> LENGTH: 480
<212> TYPE: DNA
<213> ORGANISM: Mentha spicata

<400> SEQUEN
       CE: 52 cggcaattat aatccttgtg gcaacctaca tcgtatccct cctaatcaac caatggcgaa      60
aatcgaaatc ccaacaaaac ctacctccga gccctccgaa gctgccggtg atcgccacc     120 tccacttcct gtggggaggg cttccccagc acgtgtttag gagcatagcc cagaagtacg    180
ggccggtggc gcacgtgcag cttactcggt ggtgctgtcg tcggcggagg cagcgaagca    240
ggcgatgaag gtgctggacc cgaacttcgc cgaccggttc gacggcatcg ggtccaggac    300
catgtggtac gacaaagatg acatcatctt cagcccttac aacgatcact ggcgccagat    360
gcggaggatc tgcgtgacag agctgctgag cccgaagaac gtcaggtcct tcgggtacat    420
aaggcaggag gagatcgagc gctgctcggg tcgtcggggg gagcgccggt cgacgtgacg    480

<210> SEQ ID NO 53
```

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: primer 22CF
<220> FEATURE:
<221> NAME/KEY: misc_feature
<222> LOCATION: (1)..(22)
<223> OTHER INFORMATION: sequencing primer

<400> SEQUENCE: 53
gcaacctaca tcgtatccct cc                                          22

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: primer
      4.25R3
<220> FEATURE:
<221> NAME/KEY: misc_feature
<222> LOCATION: (1)..(20)
<223> OTHER INFORMATION: sequencing primer

<400> SEQUENCE: 54
cttcaccaac tccgccaacg                                             20

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: primer
      P17START
<220> FEATURE:
<221> NAME/KEY: misc_feature
<222> LOCATION: (1)..(18)
<223> OTHER INFORMATION: sequencing primer

<400> SEQUENCE: 55
atggagcttc agatttcg                                               18

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: primer
      P17RSTOP
<220> FEATURE:
<221> NAME/KEY: misc_feature
<222> LOCATION: (1)..(21)
<223> OTHER INFORMATION: sequencing primer

<400> SEQUENCE: 56
gcactcttta ttcaaaggag c                                           21

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: primer
      S12BF
<220> FEATURE:
<221> NAME/KEY: misc_feature
<222> LOCATION: (1)..(19)
<223> OTHER INFORMATION: sequencing primer

<400> SEQUENCE: 57

```
gaaaccatgg agctcgacc                                              19
```

```
<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: primer
      S12BR
<220> FEATURE:
<221> NAME/KEY: misc_feature
<222> LOCATION: (1)..(20)
<223> OTHER INFORMATION: sequencing primer

<400> SEQUENCE: 58
tatgctaagc ttcttagtgg                                             20
```

```
<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: primer
      BAC4PCRF
<220> FEATURE:
<221> NAME/KEY: misc_feature
<222> LOCATION: (1)..(24)
<223> OTHER INFORMATION: sequencing primer

<400> SEQUENCE: 59
tttactgttt tcgtaacagt tttg                                        24
```

```
<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: primer
      BAC4PCRR
<220> FEATURE:
<221> NAME/KEY: misc_feature
<222> LOCATION: (1)..(21)
<223> OTHER INFORMATION: sequencing primer

<400> SEQUENCE: 60
caacaacgca cagaatctag c                                           21
```

```
<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: primer
      BAC3PCRF
<220> FEATURE:
<221> NAME/KEY: misc_feature
<222> LOCATION: (1)..(24)
<223> OTHER INFORMATION: sequencing primer

<400> SEQUENCE: 61
tttactgttt tcgtaacagt tttg                                        24
```

```
<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: primer
      BAC3PCR-R
```

-continued

```
<220> FEATURE:
<221> NAME/KEY: misc_feature
<222> LOCATION: (1)..(21)
<223> OTHER INFORMATION: sequencing primer

<400> SEQUENCE: 62
caacaacgca cagaatctag c                                              21

<210> SEQ ID NO 63
<211> LENGTH: 1762
<212> TYPE: DNA
<213> ORGANISM: Artificial Sequence
<220> FEATURE:
<223> OTHER INFORMATION: Description of Artificial Sequence:
      computer-generated nucleic acid sequence
<220> FEATURE:
<221> NAME/KEY: CDS
<222> LOCATION: (20)..(1507)
<223> OTHER INFORMATION: Computer-generated nucleic acid sequence
      encoding limonene-6-hydroxylase variant

<400> SEQUENCE: 63
aaaaaactaa aagaaaca atg gag ctc gac ctt ttg tcg gca att ata atc      52
                    Met Glu Leu Asp Leu Leu Ser Ala Ile Ile Ile
                     1               5                  10 ctt gtg gca acc tac atc gta tcc ctc cta atc aac caa tgg cga aaa    100
Leu Val Ala Thr Tyr Ile Val Ser Leu Leu Ile Asn Gln Trp Arg Lys
            15                  20                  25 tcg aaa tcc caa caa aac cta cct ccg agc cct ccg aag ctg ccg gtg    148
Ser Lys Ser Gln Gln Asn Leu Pro Pro Ser Pro Pro Lys Leu Pro Val
         30                  35                  40 atc ggc cac ctc cac ttc ctg tgg gga ggg ctt ccc cag cac gtg ttt    196
Ile Gly His Leu His Phe Leu Trp Gly Gly Leu Pro Gln His Val Phe
 45                  50                  55 agg agc ata gcc cag aag tac ggg ccg gtg gcg cac gtg cag ctg gga    244
Arg Ser Ile Ala Gln Lys Tyr Gly Pro Val Ala His Val Gln Leu Gly
 60                  65                  70                  75 gaa gtg tac tcg gtg gtg ctg tcg tcg gcg gag gca gcg aag cag gcg    292
Glu Val Tyr Ser Val Val Leu Ser Ser Ala Glu Ala Ala Lys Gln Ala
                 80                  85                  90 atg aag gtg ctg gac ccg aac ttc gcc gac cgg ttc gac ggc atc ggg    340
Met Lys Val Leu Asp Pro Asn Phe Ala Asp Arg Phe Asp Gly Ile Gly
             95                 100                 105 tcc agg acc atg tgg tac gac aaa gat gac atc atc ttc agc cct tac    388
Ser Arg Thr Met Trp Tyr Asp Lys Asp Asp Ile Ile Phe Ser Pro Tyr
        110                 115                 120 aac gat cac tgg cgc cag atg cgg agg atc tgc gtg aca gag ctg ctg    436
Asn Asp His Trp Arg Gln Met Arg Arg Ile Cys Val Thr Glu Leu Leu
    125                 130                 135 agc ccg aag aac gtc agg tcc ttc ggg tac ata agg cag gag gag atc    484
Ser Pro Lys Asn Val Arg Ser Phe Gly Tyr Ile Arg Gln Glu Glu Ile
140                 145                 150                 155 gag cgc ctc atc cgg ctg ctc ggg tcg tcg ggg gga gcg ccg gtc gac    532
Glu Arg Leu Ile Arg Leu Leu Gly Ser Ser Gly Gly Ala Pro Val Asp
                160                 165                 170 gtg acg gag gag gtg tcg aag atg tcg tgt gtc gtc gtg tgc agg gcg    580
Val Thr Glu Glu Val Ser Lys Met Ser Cys Val Val Val Cys Arg Ala
            175                 180                 185 gcg ttc ggg agt gtg ctc aag gac cag ggt tcg ttg gcg gag ttg gtg    628
Ala Phe Gly Ser Val Leu Lys Asp Gln Gly Ser Leu Ala Glu Leu Val
        190                 195                 200 aag gag tcg ctg gca ttg gcg tcc ggg ttt gag ctg gcg gat ctc tac    676
Lys Glu Ser Leu Ala Leu Ala Ser Gly Phe Glu Leu Ala Asp Leu Tyr
```

```
             205                 210                 215
cct tcc tca tgg ctc ctc aac ctg cct agc ttg aac aag tac agg ttg      724
Pro Ser Ser Trp Leu Leu Asn Leu Pro Ser Leu Asn Lys Tyr Arg Leu
220                 225                 230                 235 cag agg atg cgc cgc cgc ctc gat cac atc ctt gat ggg ttc ctg gag      772
Gln Arg Met Arg Arg Arg Leu Asp His Ile Leu Asp Gly Phe Leu Glu
                240                 245                 250 gag cat agg gag aag aag agc ggc gag ttt gga ggc gag gac atc gtc      820
Glu His Arg Glu Lys Lys Ser Gly Glu Phe Gly Gly Glu Asp Ile Val
            255                 260                 265 gac gtt ctt ttc agg atg cag aag ggc agc gac atc aaa att ccc att      868
Asp Val Leu Phe Arg Met Gln Lys Gly Ser Asp Ile Lys Ile Pro Ile
        270                 275                 280 act tcc aat tgc atc aag ggt ttc att ttc gac acc ttc tcc gcg gga      916
Thr Ser Asn Cys Ile Lys Gly Phe Ile Phe Asp Thr Phe Ser Ala Gly
    285                 290                 295 gct gaa acg tct tcg acg acc atc tca tgg gcg ttg tcg gaa ctg atg      964
Ala Glu Thr Ser Ser Thr Thr Ile Ser Trp Ala Leu Ser Glu Leu Met
300                 305                 310                 315 agg aat ccg gcg aag atg gcc aag gtg cag gcg gag gta aga gag gcg     1012
Arg Asn Pro Ala Lys Met Ala Lys Val Gln Ala Glu Val Arg Glu Ala
                320                 325                 330 ctc aag gga aag aca gtc gtg gat ttg agc gag gtg caa gag cta aaa     1060
Leu Lys Gly Lys Thr Val Val Asp Leu Ser Glu Val Gln Glu Leu Lys
            335                 340                 345 tac ctg aga tcg gtg tta aag gag act ctg agg ctg cac cct ccc ttt     1108
Tyr Leu Arg Ser Val Leu Lys Glu Thr Leu Arg Leu His Pro Pro Phe
        350                 355                 360 cca tta atc cca aga caa tcc agg gaa gaa tgc gag gtt aac ggg tac     1156
Pro Leu Ile Pro Arg Gln Ser Arg Glu Glu Cys Glu Val Asn Gly Tyr
    365                 370                 375 acg att ccg gcc aaa act aga atc ttc atc aac gtc tgg gct atc gga     1204
Thr Ile Pro Ala Lys Thr Arg Ile Phe Ile Asn Val Trp Ala Ile Gly
380                 385                 390                 395 agg gat ccc caa tac tgg gaa gat ccc gac acc ttc cgc cct gag aga     1252
Arg Asp Pro Gln Tyr Trp Glu Asp Pro Asp Thr Phe Arg Pro Glu Arg
                400                 405                 410 ttc gat gag gtt tcc agg gat ttc atg gga aac gat ttc gag ttc atc     1300
Phe Asp Glu Val Ser Arg Asp Phe Met Gly Asn Asp Phe Glu Phe Ile
            415                 420                 425 cca ttc ggg gcg ggt cga aga atc tgc ccc ggt tta cat ttc ggg ctg     1348
Pro Phe Gly Ala Gly Arg Arg Ile Cys Pro Gly Leu His Phe Gly Leu
        430                 435                 440 gca aat gtt gag atc cca ttg gcg caa ctg ctc tac cac ttc gac tgg     1396
Ala Asn Val Glu Ile Pro Leu Ala Gln Leu Leu Tyr His Phe Asp Trp
    445                 450                 455 aaa ttg cca caa gga atg act gat gcc gac ttg gac atg acg gag acc     1444
Lys Leu Pro Gln Gly Met Thr Asp Ala Asp Leu Asp Met Thr Glu Thr
460                 465                 470                 475 cca ggt ctt tct ggg cca aaa aag aaa aat gtt tgc ttg gtt ccc aca     1492
Pro Gly Leu Ser Gly Pro Lys Lys Lys Asn Val Cys Leu Val Pro Thr
                480                 485                 490 ctc tat aaa agt cct taaccactaa gaagttagca taataagaca tctaaaattg     1547
Leu Tyr Lys Ser Pro
            495 tcataatcat ctaattattg ttacacttct tctatcatgt cattttgaga agtgtcttat     1607 agaggtggcc acggttccgg ttccagttcg gaagcggaac cgaaccatca gttacggttc     1667 tcagcaagaa gcgaaccgtc ccgccccccc tactgtgttt gagatataaa acacataaaa     1727
```

-continued

```
taaaataaaa aaaacgctat ttttttttaa aaaaa                              1762
```

<210> SEQ ID NO 64
<211> LENGTH: 496
<212> TYPE: PRT
<213> ORGANISM: Artificial Sequence

<400> SEQUENCE: 64

```
Met Glu Leu Asp Leu Leu Ser Ala Ile Ile Ile Leu Val Ala Thr Tyr
  1               5                  10                  15

Ile Val Ser Leu Leu Ile Asn Gln Trp Arg Lys Ser Lys Ser Gln Gln
                 20                  25                  30

Asn Leu Pro Pro Ser Pro Pro Lys Leu Pro Val Ile Gly His Leu His
             35                  40                  45

Phe Leu Trp Gly Gly Leu Pro Gln His Val Phe Arg Ser Ile Ala Gln
         50                  55                  60

Lys Tyr Gly Pro Val Ala His Val Gln Leu Gly Glu Val Tyr Ser Val
 65                  70                  75                  80

Val Leu Ser Ser Ala Glu Ala Ala Lys Gln Ala Met Lys Val Leu Asp
                 85                  90                  95

Pro Asn Phe Ala Asp Arg Phe Asp Gly Ile Gly Ser Arg Thr Met Trp
            100                 105                 110

Tyr Asp Lys Asp Asp Ile Ile Phe Ser Pro Tyr Asn Asp His Trp Arg
        115                 120                 125

Gln Met Arg Arg Ile Cys Val Thr Glu Leu Leu Ser Pro Lys Asn Val
    130                 135                 140

Arg Ser Phe Gly Tyr Ile Arg Gln Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
            180                 185                 190

Leu Lys Asp Gln Gly Ser Leu Ala Glu Leu Val Lys Glu Ser Leu Ala
        195                 200                 205

Leu Ala Ser Gly Phe Glu Leu Ala Asp Leu Tyr Pro Ser Ser Trp Leu
    210                 215                 220

Leu Asn Leu Pro Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Glu Phe Gly Gly Glu Asp Ile Val Asp Val Leu Phe Arg
            260                 265                 270

Met Gln Lys Gly Ser Asp Ile Lys Ile Pro Ile Thr Ser Asn Cys Ile
        275                 280                 285

Lys Gly Phe Ile Phe Asp Thr Phe Ser Ala Gly Ala Glu Thr Ser Ser
    290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
        355                 360                 365
```

```
Gln Ser Arg Glu Glu Cys Glu Val Asn Gly Tyr Thr Ile Pro Ala Lys
    370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Val Ser
                405                 410                 415

Arg Asp Phe Met Gly Asn Asp Phe Glu Phe Ile Pro Phe Gly Ala Gly
                420                 425                 430

Arg Arg Ile Cys Pro Gly Leu His Phe Gly Leu Ala Asn Val Glu Ile
            435                 440                 445

Pro Leu Ala Gln Leu Leu Tyr His Phe Asp Trp Lys Leu Pro Gln Gly
    450                 455                 460

Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
                485                 490                 495

<210> SEQ ID NO 65
<211> LENGTH: 1762
<212> TYPE: DNA
<213> ORGANISM: Artificial Sequence
<220> FEATURE:
<223> OTHER INFORMATION: Description of Artificial Sequence:
      computer-generated nucleic acid sequence encoding
      limonene-6-hydroxylase
<220> FEATURE:
<221> NAME/KEY: misc_feature
<222> LOCATION: (1)..(1762)
<223> OTHER INFORMATION: computer-generated nucleic acid sequence
      encoding spearmint limonene-6-hydroxylase variant
<220> FEATURE:
<221> NAME/KEY: CDS
<222> LOCATION: (20)..(1507)

<400> SEQUENCE: 65
aaaaaactaa aagaaaaca atg gag ctc gac ctt ttg tcg gca att ata atc        52
                    Met Glu Leu Asp Leu Leu Ser Ala Ile Ile Ile
                      1               5                  10 ctt gtg gca acc tac atc gta tcc ctc cta atc aac caa tgg cga aaa        100
Leu Val Ala Thr Tyr Ile Val Ser Leu Leu Ile Asn Gln Trp Arg Lys
                15                  20                  25 tcg aaa tcc caa caa aac cta cct ccg agc cct ccg aag ctg ccg gtg        148
Ser Lys Ser Gln Gln Asn Leu Pro Pro Ser Pro Pro Lys Leu Pro Val
            30                  35                  40 atc ggc cac ctc cac ttc ctg tgg gga ggg ctt ccc cag cac gtg ttt        196
Ile Gly His Leu His Phe Leu Trp Gly Gly Leu Pro Gln His Val Phe
        45                  50                  55 agg agc ata gcc cag aag tac ggg ccg gtg gcg cac gtg cag ctg gga        244
Arg Ser Ile Ala Gln Lys Tyr Gly Pro Val Ala His Val Gln Leu Gly
 60                  65                  70                  75 gaa gtg tac tcg gtg gtg ctg tcg tcg gcg gag gca gcg aag cag gcg        292
Glu Val Tyr Ser Val Val Leu Ser Ser Ala Glu Ala Ala Lys Gln Ala
                80                  85                  90 atg aag gtg ctg gac ccg aac ttc gcc gac cgg ttc gac ggc atc ggg        340
Met Lys Val Leu Asp Pro Asn Phe Ala Asp Arg Phe Asp Gly Ile Gly
            95                  100                 105 tcc agg acc atg tgg tac gac aaa gat gag atc atc ttc agc cct tac        388
Ser Arg Thr Met Trp Tyr Asp Lys Asp Glu Ile Ile Phe Ser Pro Tyr
        110                 115                 120 aac gat cac tgg cgc cag atg cgg agg atc tgc gtg aca gag ctg ctg        436
Asn Asp His Trp Arg Gln Met Arg Arg Ile Cys Val Thr Glu Leu Leu
```

-continued

|  |  |  |  |  |  |  |  |  |  |  |  |  |  |  |  |
|---|---|---|---|---|---|---|---|---|---|---|---|---|---|---|---|
|  | 125 |  |  |  | 130 |  |  |  |  | 135 |  |  |  |  |  |
| agc | ccg | aag | aac | gtc | agg | tcc | ttc | ggg | tac | ata | agg | cag | gag | gag | atc | 484 |
| Ser | Pro | Lys | Asn | Val | Arg | Ser | Phe | Gly | Tyr | Ile | Arg | Gln | Glu | Glu | Ile |  |
| 140 |  |  |  |  | 145 |  |  |  |  | 150 |  |  |  |  | 155 |  |
| gag | cgc | ctc | atc | cgg | ctg | ctc | ggg | tcg | tcg | ggg | gga | gcg | ccg | gtc | gac | 532 |
| Glu | Arg | Leu | Ile | Arg | Leu | Leu | Gly | Ser | Ser | Gly | Gly | Ala | Pro | Val | Asp |  |
|  |  |  | 160 |  |  |  |  | 165 |  |  |  |  | 170 |  |  |  |
| gtg | acg | gag | gag | gtg | tcg | aag | atg | tcg | tgt | gtc | gtc | gtg | tgc | agg | gcg | 580 |
| Val | Thr | Glu | Glu | Val | Ser | Lys | Met | Ser | Cys | Val | Val | Val | Cys | Arg | Ala |  |
|  |  | 175 |  |  |  |  | 180 |  |  |  |  | 185 |  |  |  |  |
| gcg | ttc | ggg | agt | gtg | ctc | aag | gac | cag | ggt | tcg | ttg | gcg | gag | ttg | gtg | 628 |
| Ala | Phe | Gly | Ser | Val | Leu | Lys | Asp | Gln | Gly | Ser | Leu | Ala | Glu | Leu | Val |  |
|  |  | 190 |  |  |  |  | 195 |  |  |  |  | 200 |  |  |  |  |
| aag | gag | tcg | ctg | gca | ttg | gcg | tcc | ggg | ttt | gag | ctg | gcg | gat | ctc | tac | 676 |
| Lys | Glu | Ser | Leu | Ala | Leu | Ala | Ser | Gly | Phe | Glu | Leu | Ala | Asp | Leu | Tyr |  |
| 205 |  |  |  |  | 210 |  |  |  |  | 215 |  |  |  |  |  |  |
| cct | tcc | tca | tgg | ctc | ctc | aac | ctg | ctt | agc | ttg | aac | aag | tac | agg | ttg | 724 |
| Pro | Ser | Ser | Trp | Leu | Leu | Asn | Leu | Leu | Ser | Leu | Asn | Lys | Tyr | Arg | Leu |  |
| 220 |  |  |  |  | 225 |  |  |  |  | 230 |  |  |  |  | 235 |  |
| cag | agg | atg | cgc | cgc | cgc | ctc | gat | cac | atc | ctt | gat | ggg | ttc | ctg | gag | 772 |
| Gln | Arg | Met | Arg | Arg | Arg | Leu | Asp | His | Ile | Leu | Asp | Gly | Phe | Leu | Glu |  |
|  |  |  | 240 |  |  |  |  | 245 |  |  |  |  | 250 |  |  |  |
| gag | cat | agg | gag | aag | aag | agc | ggc | gag | ttt | gga | ggc | gag | gac | atc | gtc | 820 |
| Glu | His | Arg | Glu | Lys | Lys | Ser | Gly | Glu | Phe | Gly | Gly | Glu | Asp | Ile | Val |  |
|  |  | 255 |  |  |  |  | 260 |  |  |  |  | 265 |  |  |  |  |
| gac | gtt | ctt | ttc | agg | atg | cag | aag | ggc | agc | gac | atc | aaa | att | ccc | att | 868 |
| Asp | Val | Leu | Phe | Arg | Met | Gln | Lys | Gly | Ser | Asp | Ile | Lys | Ile | Pro | Ile |  |
|  |  | 270 |  |  |  |  | 275 |  |  |  |  | 280 |  |  |  |  |
| act | tcc | aat | tgc | atc | aag | ggt | ttc | att | ttc | gac | acc | ttc | tcc | gcg | gga | 916 |
| Thr | Ser | Asn | Cys | Ile | Lys | Gly | Phe | Ile | Phe | Asp | Thr | Phe | Ser | Ala | Gly |  |
| 285 |  |  |  |  | 290 |  |  |  |  | 295 |  |  |  |  |  |  |
| gct | gaa | acg | tct | tcg | acg | acc | atc | tca | tgg | gcg | ttg | tcg | gaa | ctg | atg | 964 |
| Ala | Glu | Thr | Ser | Ser | Thr | Thr | Ile | Ser | Trp | Ala | Leu | Ser | Glu | Leu | Met |  |
| 300 |  |  |  |  | 305 |  |  |  |  | 310 |  |  |  |  | 315 |  |
| agg | aat | ccg | gcg | aag | atg | gcc | aag | gtg | cag | gcg | gag | gta | aga | gag | gcg | 1012 |
| Arg | Asn | Pro | Ala | Lys | Met | Ala | Lys | Val | Gln | Ala | Glu | Val | Arg | Glu | Ala |  |
|  |  |  | 320 |  |  |  |  | 325 |  |  |  |  | 330 |  |  |  |
| ctc | aag | gga | aag | aca | gtc | gtg | gat | ttg | agc | gag | gtg | caa | gag | cta | aaa | 1060 |
| Leu | Lys | Gly | Lys | Thr | Val | Val | Asp | Leu | Ser | Glu | Val | Gln | Glu | Leu | Lys |  |
|  |  | 335 |  |  |  |  | 340 |  |  |  |  | 345 |  |  |  |  |
| tac | ctg | aga | tcg | gtg | tta | aag | gag | act | ctg | agg | ctg | cac | cct | ccc | ttt | 1108 |
| Tyr | Leu | Arg | Ser | Val | Leu | Lys | Glu | Thr | Leu | Arg | Leu | His | Pro | Pro | Phe |  |
|  |  | 350 |  |  |  |  | 355 |  |  |  |  | 360 |  |  |  |  |
| cca | tta | atc | cca | aga | caa | tcc | agg | gaa | gaa | tgc | gag | gtt | aac | ggg | tac | 1156 |
| Pro | Leu | Ile | Pro | Arg | Gln | Ser | Arg | Glu | Glu | Cys | Glu | Val | Asn | Gly | Tyr |  |
|  | 365 |  |  |  |  | 370 |  |  |  |  | 375 |  |  |  |  |  |
| acg | att | ccg | gcc | aaa | act | aga | atc | ttc | atc | aac | gtc | tgg | gct | atc | gga | 1204 |
| Thr | Ile | Pro | Ala | Lys | Thr | Arg | Ile | Phe | Ile | Asn | Val | Trp | Ala | Ile | Gly |  |
| 380 |  |  |  |  | 385 |  |  |  |  | 390 |  |  |  |  | 395 |  |
| agg | gat | ccc | caa | tac | tgg | gaa | gat | ccc | gac | acc | ttc | cgc | cct | gag | aga | 1252 |
| Arg | Asp | Pro | Gln | Tyr | Trp | Glu | Asp | Pro | Asp | Thr | Phe | Arg | Pro | Glu | Arg |  |
|  |  |  | 400 |  |  |  |  | 405 |  |  |  |  | 410 |  |  |  |
| ttc | gat | gag | gtt | tcc | agg | gat | ttc | atg | gga | aac | gat | ttc | gag | ttc | atc | 1300 |
| Phe | Asp | Glu | Val | Ser | Arg | Asp | Phe | Met | Gly | Asn | Asp | Phe | Glu | Phe | Ile |  |
|  |  |  | 415 |  |  |  |  | 420 |  |  |  |  | 425 |  |  |  |
| cca | ttc | ggg | gcg | ggt | cga | aga | atc | tgc | ccc | ggt | tta | cat | ttc | ggg | ctg | 1348 |
| Pro | Phe | Gly | Ala | Gly | Arg | Arg | Ile | Cys | Pro | Gly | Leu | His | Phe | Gly | Leu |  |
|  |  | 430 |  |  |  |  | 435 |  |  |  |  | 440 |  |  |  |  |
| gca | aat | gtt | gag | atc | cca | ttg | gcg | caa | ctg | ctc | tac | cac | ttc | gac | tgg | 1396 |

| | | | | | | | | | | | | |
|---|---|---|---|---|---|---|---|---|---|---|---|---|
|Ala|Asn|Val|Glu|Ile|Pro|Leu|Ala|Gln|Leu|Leu|Tyr|His|Phe|Asp|Trp|
| |445| | | |450| | | | |455| | | | | |

```
aaa ttg cca caa gga atg act gat gcc gac ttg gac atg acg gag acc      1444
Lys Leu Pro Gln Gly Met Thr Asp Ala Asp Leu Asp Met Thr Glu Thr
460                 465                 470                 475 cca ggt ctt tct ggg cca aaa aag aaa aat gtt tgc ttg gtt ccc aca      1492
Pro Gly Leu Ser Gly Pro Lys Lys Lys Asn Val Cys Leu Val Pro Thr
                    480                 485                 490 ctc tat aaa agt cct taaccactaa gaagttagca taataagaca tctaaaattg      1547
Leu Tyr Lys Ser Pro
            495 tcataatcat ctaattattg ttacacttct tctatcatgt cattttgaga agtgtcttat    1607 agaggtggcc acggttccgg ttccagttcg gaagcggaac cgaaccatca gttacggttc    1667 tcagcaagaa gcgaaccgtc ccgcccccc tactgtgttt gagatataaa acacataaaa    1727 taaaataaaa aaaacgctat ttttttttaa aaaaa                                1762

<210> SEQ ID NO 66
<211> LENGTH: 496
<212> TYPE: PRT
<213> ORGANISM: Artificial Sequence

<400> SEQUENCE: 66

Met Glu Leu Asp Leu Leu Ser Ala Ile Ile Ile Leu Val Ala Thr Tyr
1               5                   10                  15

Ile Val Ser Leu Leu Ile Asn Gln Trp Arg Lys Ser Lys Ser Gln Gln
                20                  25                  30

Asn Leu Pro Pro Ser Pro Pro Lys Leu Pro Val Ile Gly His Leu His
            35                  40                  45

Phe Leu Trp Gly Gly Leu Pro Gln His Val Phe Arg Ser Ile Ala Gln
        50                  55                  60

Lys Tyr Gly Pro Val Ala His Val Gln Leu Gly Glu Val Tyr Ser Val
65                  70                  75                  80

Val Leu Ser Ser Ala Glu Ala Lys Gln Ala Met Lys Val Leu Asp
                85                  90                  95

Pro Asn Phe Ala Asp Arg Phe Asp Gly Ile Gly Ser Arg Thr Met Trp
            100                 105                 110

Tyr Asp Lys Asp Glu Ile Ile Phe Ser Pro Tyr Asn Asp His Trp Arg
        115                 120                 125

Gln Met Arg Arg Ile Cys Val Thr Glu Leu Leu Ser Pro Lys Asn Val
130                 135                 140

Arg Ser Phe Gly Tyr Ile Arg Gln Glu Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Cys Arg Ala Ala Phe Gly Ser Val
            180                 185                 190

Leu Lys Asp Gln Gly Ser Leu Ala Glu Leu Val Lys Glu Ser Leu Ala
        195                 200                 205

Leu Ala Ser Gly Phe Glu Leu Ala Asp Leu Tyr Pro Ser Ser Trp Leu
    210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255
```

```
Lys Ser Gly Glu Phe Gly Gly Glu Asp Ile Val Asp Val Leu Phe Arg
            260                 265                 270

Met Gln Lys Gly Ser Asp Ile Lys Ile Pro Ile Thr Ser Asn Cys Ile
            275                 280                 285

Lys Gly Phe Ile Phe Asp Thr Phe Ser Ala Gly Ala Glu Thr Ser Ser
            290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
            355                 360                 365

Gln Ser Arg Glu Glu Cys Glu Val Asn Gly Tyr Thr Ile Pro Ala Lys
            370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
                420                 425                 430

Arg Arg Ile Cys Pro Gly Leu His Phe Gly Leu Ala Asn Val Glu Ile
            435                 440                 445

Pro Leu Ala Gln Leu Leu Tyr His Phe Asp Trp Lys Leu Pro Gln Gly
            450                 455                 460

Met Thr Asp Ala Asp Leu Asp Met Thr Glu Thr Pro Gly Leu Ser Gly
465                 470                 475                 480

Pro Lys Lys Lys Asn Val Cys Leu Val Pro Thr Leu Tyr Lys Ser Pro
                485                 490                 495

<210> SEQ ID NO 67
<211> LENGTH: 1665
<212> TYPE: DNA
<213> ORGANISM: Artificial Sequence
<220> FEATURE:
<223> OTHER INFORMATION: Description of Artificial Sequence:
      computer-generated nucleic acid sequence encoding
      limonene-3-hydroxylase
<220> FEATURE:
<221> NAME/KEY: misc_feature
<222> LOCATION: (1)..(1665)
<223> OTHER INFORMATION: computer-generated nucleic acid sequence
      encoding limonene-3-hydroxylase variant
<220> FEATURE:
<221> NAME/KEY: CDS
<222> LOCATION: (19)..(1518)

<400> SEQUENCE: 67
agaaaataaa ataaaata atg gag ctt cag att tcg tcg gcg att ata atc        51
                    Met Glu Leu Gln Ile Ser Ser Ala Ile Ile Ile
                     1               5                  10 ctt gta gta acc tac acc ata tcc ctc cta ata atc aag caa tgg cga       99
Leu Val Val Thr Tyr Thr Ile Ser Leu Leu Ile Ile Lys Gln Trp Arg
            15                  20                  25 aaa ccg aaa ccc caa gag aac ctg cct ccg ggc ccg ccg aag ctg ccg      147
Lys Pro Lys Pro Gln Glu Asn Leu Pro Pro Gly Pro Pro Lys Leu Pro
        30                  35                  40 ctg atc ggg cac ctc cac ctc cta tgg ggg aag ctg ccg cag cac gcg      195
Leu Ile Gly His Leu His Leu Leu Trp Gly Lys Leu Pro Gln His Ala
```

|  |  |
|---|---|
| ctg gcc agc gtg gcg aag cag tac ggc cca gtg gcg cac gtg cag ctc<br>Leu Ala Ser Val Ala Lys Gln Tyr Gly Pro Val Ala His Val Gln Leu<br>60               65                 70               75 | 243 |
| ggc gag gtg ttc tcc gtc gtg ctc tcg tcc cgc gag gcc acg aag gag<br>Gly Glu Val Phe Ser Val Val Leu Ser Ser Arg Glu Ala Thr Lys Glu<br>               80               85               90 | 291 |
| gcg atg aag ctg gtg gac ccg gcc tgc gcg gac cgg ttc gag agc atc<br>Ala Met Lys Leu Val Asp Pro Ala Cys Ala Asp Arg Phe Glu Ser Ile<br>               95              100             105 | 339 |
| ggg acg aag atc atg tgg tac gac aac gac gac atc atc ttc agc ccc<br>Gly Thr Lys Ile Met Trp Tyr Asp Asn Asp Asp Ile Ile Phe Ser Pro<br>           110               115             120 | 387 |
| tac agc gtg cac tgg cgc cag atg cgg aag atc tgc gtc tcc gag ctc<br>Tyr Ser Val His Trp Arg Gln Met Arg Lys Ile Cys Val Ser Glu Leu<br>           125               130             135 | 435 |
| ctc agc gcc cgc aac gtc cgc tcc ttc ggc ttc atc agg cag gac gag<br>Leu Ser Ala Arg Asn Val Arg Ser Phe Gly Phe Ile Arg Gln Asp Glu<br>140               145              150             155 | 483 |
| gtg tcc cgc ctc ctc ggc cac ctc cgc tcc tcg gcc gcg gcg ggg gag<br>Val Ser Arg Leu Leu Gly His Leu Arg Ser Ser Ala Ala Ala Gly Glu<br>                  160             165             170 | 531 |
| gcc gtg gac ctc acg gag cgg ata gcg acg ctg acg tgc tcc atc atc<br>Ala Val Asp Leu Thr Glu Arg Ile Ala Thr Leu Thr Cys Ser Ile Ile<br>               175              180             185 | 579 |
| tgc agg gcg gcg ttc ggg agc gtg atc agg gac cac gag gag ctg gtg<br>Cys Arg Ala Ala Phe Gly Ser Val Ile Arg Asp His Glu Glu Leu Val<br>           190               195             200 | 627 |
| gag ctg gtg aag gac gcc ctc agc atg gcg tcc ggg ttc gag ctc gcc<br>Glu Leu Val Lys Asp Ala Leu Ser Met Ala Ser Gly Phe Glu Leu Ala<br>           205               210             215 | 675 |
| gac atg ttc ccc tcc tcc aag ctc ctc aac ttg ctc tgc tgg aac aag<br>Asp Met Phe Pro Ser Ser Lys Leu Leu Asn Leu Leu Cys Trp Asn Lys<br>220               225              230             235 | 723 |
| agc aag ctg tgg agg atg cgc cgc cgc gtc gac gcc atc ctc gag gcc<br>Ser Lys Leu Trp Arg Met Arg Arg Arg Val Asp Ala Ile Leu Glu Ala<br>               240              245             250 | 771 |
| atc gtg gag gag cac aag ctc aag aag agc ggc gag ttt ggc ggc gag<br>Ile Val Glu Glu His Lys Leu Lys Lys Ser Gly Glu Phe Gly Gly Glu<br>           255               260             265 | 819 |
| gac att att gac gta ctc ttt agg atg cag aag gat agc cag atc aaa<br>Asp Ile Ile Asp Val Leu Phe Arg Met Gln Lys Asp Ser Gln Ile Lys<br>           270               275             280 | 867 |
| gtc ccc atc acc acc aaa gcc atc aaa gcc ttc atc ttc gac acg ttc<br>Val Pro Ile Thr Thr Lys Ala Ile Lys Ala Phe Ile Phe Asp Thr Phe<br>285               290              295 | 915 |
| tca gcg ggg acc gag aca tca tca acc acc acc ctg tgg gtg atg gcg<br>Ser Ala Gly Thr Glu Thr Ser Ser Thr Thr Thr Leu Trp Val Met Ala<br>300               305              310             315 | 963 |
| gag ctg atg agg aat cca gag gtg atg gcg aaa gcg cag gcg gag gtg<br>Glu Leu Met Arg Asn Pro Glu Val Met Ala Lys Ala Gln Ala Glu Val<br>           320               325             330 | 1011 |
| aga gcg gcg ctg aag ggg aag acg gac tgg gac gtg gac gac gtg cag<br>Arg Ala Ala Leu Lys Gly Lys Thr Asp Trp Asp Val Asp Asp Val Gln<br>           335               340             345 | 1059 |
| gag ctt aag tac atg aaa tcg gtg gtg aag gag acg atg agg atg cac<br>Glu Leu Lys Tyr Met Lys Ser Val Val Lys Glu Thr Met Arg Met His<br>           350               355             360 | 1107 |
| cct ccg atc ccg ttg atc ccg aga tca tgc aga gaa gaa tgc gag gtc | 1155 |

```
                                                          Pro Pro Ile Pro Leu Ile Pro Arg Ser Cys Arg Glu Glu Cys Glu Val
                                                              365                 370                 375 aac ggg tac acg att ccg aat aag gcc aga atc atg atc aac gtg tgg                                                      1203
Asn Gly Tyr Thr Ile Pro Asn Lys Ala Arg Ile Met Ile Asn Val Trp
380                 385                 390                 395 tcc atg ggt agg aat cct ctc tac tgg gaa aaa ccc gag acc ttt tgg                                                      1251
Ser Met Gly Arg Asn Pro Leu Tyr Trp Glu Lys Pro Glu Thr Phe Trp
                    400                 405                 410 ccc gaa agg ttt gac caa gtc tcg agg gat ttc atg gga aac gat ttc                                                      1299
Pro Glu Arg Phe Asp Gln Val Ser Arg Asp Phe Met Gly Asn Asp Phe
                415                 420                 425 gag ttc atc cca ttt gga gct gga aga aga atc tgc ccc ggt ttg aat                                                      1347
Glu Phe Ile Pro Phe Gly Ala Gly Arg Arg Ile Cys Pro Gly Leu Asn
            430                 435                 440 ttc ggg ttg gca aat gtt gag gtc cca ttg gca cag ctt ctt tac cac                                                      1395
Phe Gly Leu Ala Asn Val Glu Val Pro Leu Ala Gln Leu Leu Tyr His
        445                 450                 455 ttc gac tgg aag ttg gcg gaa gga atg aac cct tcc gat atg gac atg                                                      1443
Phe Asp Trp Lys Leu Ala Glu Gly Met Asn Pro Ser Asp Met Asp Met
460                 465                 470                 475 tct gag gca gaa ggc ctt acc gga ata aga aag aac aat ctt cta ctc                                                      1491
Ser Glu Ala Glu Gly Leu Thr Gly Ile Arg Lys Asn Asn Leu Leu Leu
                    480                 485                 490 gtt ccc aca ccc tac gat cct tcc tca tgatcaatta atactcttta                                                            1538
Val Pro Thr Pro Tyr Asp Pro Ser Ser
                495                 500 atttgctcct ttgaataaag agtgcatata catatatgat atatacacat acacacacat                                                    1598
atactatata tgtatatgta gctttgggct atgaatatag aaattatgta aaaaaaataa                                                    1658
aaaggaa                                                                                                              1665

<210> SEQ ID NO 68
<211> LENGTH: 500
<212> TYPE: PRT
<213> ORGANISM: Artificial Sequence

<400> SEQUENCE: 68

Met Glu Leu Gln Ile Ser Ser Ala Ile Ile Ile Leu Val Val Thr Tyr
1               5                   10                  15

Thr Ile Ser Leu Leu Ile Ile Lys Gln Trp Arg Lys Pro Lys Pro Gln
            20                  25                  30

Glu Asn Leu Pro Pro Gly Pro Lys Leu Pro Leu Ile Gly His Leu
        35                  40                  45

His Leu Leu Trp Gly Lys Leu Pro Gln His Ala Leu Ala Ser Val Ala
    50                  55                  60

Lys Gln Tyr Gly Pro Val Ala His Val Gln Leu Gly Glu Val Phe Ser
65                  70                  75                  80

Val Val Leu Ser Ser Arg Glu Ala Thr Lys Glu Ala Met Lys Leu Val
                85                  90                  95

Asp Pro Ala Cys Ala Asp Arg Phe Glu Ser Ile Gly Thr Lys Ile Met
            100                 105                 110

Trp Tyr Asp Asn Asp Ile Ile Phe Ser Pro Tyr Ser Val His Trp
        115                 120                 125

Arg Gln Met Arg Lys Ile Cys Val Ser Glu Leu Leu Ser Ala Arg Asn
    130                 135                 140

Val Arg Ser Phe Gly Phe Ile Arg Gln Asp Glu Val Ser Arg Leu Leu
145                 150                 155                 160
```

```
Gly His Leu Arg Ser Ser Ala Ala Gly Glu Ala Val Asp Leu Thr
            165                 170                 175

Glu Arg Ile Ala Thr Leu Thr Cys Ser Ile Ile Cys Arg Ala Ala Phe
            180                 185                 190

Gly Ser Val Ile Arg Asp His Glu Glu Leu Val Glu Leu Val Lys Asp
            195                 200                 205

Ala Leu Ser Met Ala Ser Gly Phe Glu Leu Ala Asp Met Phe Pro Ser
            210                 215                 220

Ser Lys Leu Leu Asn Leu Leu Cys Trp Asn Lys Ser Lys Leu Trp Arg
225                 230                 235                 240

Met Arg Arg Arg Val Asp Ala Ile Leu Glu Ala Ile Val Glu Glu His
                245                 250                 255

Lys Leu Lys Lys Ser Gly Glu Phe Gly Glu Asp Ile Ile Asp Val
            260                 265                 270

Leu Phe Arg Met Gln Lys Asp Ser Gln Ile Lys Val Pro Ile Thr Thr
            275                 280                 285

Lys Ala Ile Lys Ala Phe Ile Phe Asp Thr Phe Ser Ala Gly Thr Glu
290                 295                 300

Thr Ser Ser Thr Thr Thr Leu Trp Val Met Ala Glu Leu Met Arg Asn
305                 310                 315                 320

Pro Glu Val Met Ala Lys Ala Gln Ala Glu Val Arg Ala Ala Leu Lys
                325                 330                 335

Gly Lys Thr Asp Trp Asp Val Asp Val Gln Glu Leu Lys Tyr Met
            340                 345                 350

Lys Ser Val Val Lys Glu Thr Met Arg Met His Pro Pro Ile Pro Leu
            355                 360                 365

Ile Pro Arg Ser Cys Arg Glu Glu Cys Glu Val Asn Gly Tyr Thr Ile
            370                 375                 380

Pro Asn Lys Ala Arg Ile Met Ile Asn Val Trp Ser Met Gly Arg Asn
385                 390                 395                 400

Pro Leu Tyr Trp Glu Lys Pro Glu Thr Phe Trp Pro Glu Arg Phe Asp
                405                 410                 415

Gln Val Ser Arg Asp Phe Met Gly Asn Asp Phe Glu Phe Ile Pro Phe
                420                 425                 430

Gly Ala Gly Arg Arg Ile Cys Pro Gly Leu Asn Phe Gly Leu Ala Asn
            435                 440                 445

Val Glu Val Pro Leu Ala Gln Leu Leu Tyr His Phe Asp Trp Lys Leu
450                 455                 460

Ala Glu Gly Met Asn Pro Ser Asp Met Asp Met Ser Glu Ala Glu Gly
465                 470                 475                 480

Leu Thr Gly Ile Arg Lys Asn Asn Leu Leu Leu Val Pro Thr Pro Tyr
                485                 490                 495

Asp Pro Ser Ser
            500

<210> SEQ ID NO 69
<211> LENGTH: 1665
<212> TYPE: DNA
<213> ORGANISM: Artificial Sequence
<220> FEATURE:
<223> OTHER INFORMATION: Description of Artificial Sequence:
      computer-generated nucleic acid sequence encoding
      limonene-3-hydroxylase
<220> FEATURE:
<221> NAME/KEY: misc_feature
<222> LOCATION: (1)..(1665)
<223> OTHER INFORMATION: computer-generated nucleic acid sequence
``` encoding limonene-3-hydroxylase protein variant
<220> FEATURE:
<221> NAME/KEY: CDS
<222> LOCATION: (19)..(1518)

<400> SEQUENCE: 69

```
agaaaataaa ataaaata atg gag ctt cag att tcg tcg gcg att ata atc         51
                    Met Glu Leu Gln Ile Ser Ser Ala Ile Ile Ile
                     1               5                  10 ctt gta gta acc tac acc ata tcc ctc cta ata atc aag caa tgg cga         99
Leu Val Val Thr Tyr Thr Ile Ser Leu Leu Ile Ile Lys Gln Trp Arg
             15                  20                  25 aaa ccg aaa ccc caa gag aac ctg cct ccg ggc ccg ccg aag ctg ccg        147
Lys Pro Lys Pro Gln Glu Asn Leu Pro Pro Gly Pro Pro Lys Leu Pro
         30                  35                  40 ctg atc ggg cac ctc cac ctc cta tgg ggg aag ctg ccg cag cac gcg        195
Leu Ile Gly His Leu His Leu Leu Trp Gly Lys Leu Pro Gln His Ala
     45                  50                  55 ctg gcc agc gtg gcg aag cag tac ggc cca gtg gcg cac gtg cag ctc        243
Leu Ala Ser Val Ala Lys Gln Tyr Gly Pro Val Ala His Val Gln Leu
 60                  65                  70                  75 ggc gag gtg ttc tcc gtc gtg ctc tcg tcc cgc gag gcc acg aag gag        291
Gly Glu Val Phe Ser Val Val Leu Ser Ser Arg Glu Ala Thr Lys Glu
                 80                  85                  90 gcg atg aag ctg gtg gac ccg gcc tgc gcg gac cgg ttc gag agc atc        339
Ala Met Lys Leu Val Asp Pro Ala Cys Ala Asp Arg Phe Glu Ser Ile
             95                 100                 105 ggg acg aag atc atg tgg tac gac aac gac gac atc atc ttc agc ccc        387
Gly Thr Lys Ile Met Trp Tyr Asp Asn Asp Asp Ile Ile Phe Ser Pro
        110                 115                 120 tac agc gtg cac tgg cgc cag atg cgg aag atc tgc gtc tcc gag ctc        435
Tyr Ser Val His Trp Arg Gln Met Arg Lys Ile Cys Val Ser Glu Leu
    125                 130                 135 ctc agc gcc cgc aac gtc cgc tcc ttc ggc ttc atc agg cag gac gag        483
Leu Ser Ala Arg Asn Val Arg Ser Phe Gly Phe Ile Arg Gln Asp Glu
140                 145                 150                 155 gtg tcc cgc ctc ctc ggc cac ctc cgc tcc tcg gcc gcg gcg ggg gag        531
Val Ser Arg Leu Leu Gly His Leu Arg Ser Ser Ala Ala Ala Gly Glu
                160                 165                 170 gcc gtg gac ctc acg gag cgg ata gcg acg ctg acg tgc tcc atc atc        579
Ala Val Asp Leu Thr Glu Arg Ile Ala Thr Leu Thr Cys Ser Ile Ile
            175                 180                 185 tgc agg gcg gcg ttc ggg agc gtg atc agg gac cac gag gag ctg gtg        627
Cys Arg Ala Ala Phe Gly Ser Val Ile Arg Asp His Glu Glu Leu Val
        190                 195                 200 gag ctg gtg aag gac gcc ctc agc atg gcg tcc ggg ttc gag ctc gcc        675
Glu Leu Val Lys Asp Ala Leu Ser Met Ala Ser Gly Phe Glu Leu Ala
    205                 210                 215 gac atg ttc ccc tcc tcc aag ctc ctc aac ttg ctc tgc tgg aac aag        723
Asp Met Phe Pro Ser Ser Lys Leu Leu Asn Leu Leu Cys Trp Asn Lys
220                 225                 230                 235 agc aag ctg tgg agg atg cgc cgc cgc gtc gac gcc atc ctc gag gcc        771
Ser Lys Leu Trp Arg Met Arg Arg Arg Val Asp Ala Ile Leu Glu Ala
                240                 245                 250 atc gtg gac gag cac aag ctc aag aag agc ggc gag ttt ggc ggc gag        819
Ile Val Asp Glu His Lys Leu Lys Lys Ser Gly Glu Phe Gly Gly Glu
            255                 260                 265 gac att att gac gta ctc ttt agg atg cag aag gat agc cag atc aaa        867
Asp Ile Ile Asp Val Leu Phe Arg Met Gln Lys Asp Ser Gln Ile Lys
        270                 275                 280
```

-continued

| | | | | | | | | | | | | | | | |
|---|---|---|---|---|---|---|---|---|---|---|---|---|---|---|---|
| gtc | ccc | atc | acc | acc | aac | gcc | atc | aaa | gcc | ttc | atc | ttc | gac | acg | ttc | 915 |
| Val | Pro | Ile | Thr | Thr | Asn | Ala | Ile | Lys | Ala | Phe | Ile | Phe | Asp | Thr | Phe |
| 285 | | | | 290 | | | | | 295 | | | | | | |

| tca | gcg | ggg | acc | gag | aca | tca | tca | acc | acc | acc | ctg | tgg | gtg | atg | gcg | 963 |
|---|---|---|---|---|---|---|---|---|---|---|---|---|---|---|---|---|
| Ser | Ala | Gly | Thr | Glu | Thr | Ser | Ser | Thr | Thr | Thr | Leu | Trp | Val | Met | Ala |
| 300 | | | | | 305 | | | | | 310 | | | | | 315 |

| gag | ctg | atg | agg | aat | cca | gag | gtg | atg | gcg | aaa | gcg | cag | gcg | gag | gtg | 1011 |
|---|---|---|---|---|---|---|---|---|---|---|---|---|---|---|---|---|
| Glu | Leu | Met | Arg | Asn | Pro | Glu | Val | Met | Ala | Lys | Ala | Gln | Ala | Glu | Val |
| | | | | 320 | | | | | 325 | | | | | 330 | |

| aga | gcg | gcg | ctg | aag | ggg | aag | acg | gac | tgg | gac | gtg | gac | gac | gtg | cag | 1059 |
|---|---|---|---|---|---|---|---|---|---|---|---|---|---|---|---|---|
| Arg | Ala | Ala | Leu | Lys | Gly | Lys | Thr | Asp | Trp | Asp | Val | Asp | Asp | Val | Gln |
| | | | 335 | | | | | 340 | | | | | 345 | | |

| gag | ctt | aag | tac | atg | aaa | tcg | gtg | gtg | aag | gag | acg | atg | agg | atg | cac | 1107 |
|---|---|---|---|---|---|---|---|---|---|---|---|---|---|---|---|---|
| Glu | Leu | Lys | Tyr | Met | Lys | Ser | Val | Val | Lys | Glu | Thr | Met | Arg | Met | His |
| | | 350 | | | | | 355 | | | | | 360 | | | |

| cct | ccg | atc | ccg | ttg | atc | ccg | aga | tca | tgc | aga | gaa | gaa | tgc | gag | gtc | 1155 |
|---|---|---|---|---|---|---|---|---|---|---|---|---|---|---|---|---|
| Pro | Pro | Ile | Pro | Leu | Ile | Pro | Arg | Ser | Cys | Arg | Glu | Glu | Cys | Glu | Val |
| 365 | | | | | 370 | | | | | 375 | | | | | |

| aac | ggg | tac | acg | att | ccg | aat | aag | gcc | aga | atc | atg | atc | aac | gtg | tgg | 1203 |
|---|---|---|---|---|---|---|---|---|---|---|---|---|---|---|---|---|
| Asn | Gly | Tyr | Thr | Ile | Pro | Asn | Lys | Ala | Arg | Ile | Met | Ile | Asn | Val | Trp |
| 380 | | | | | 385 | | | | | 390 | | | | | 395 |

| tcc | atg | ggt | agg | aat | cct | ctc | tac | tgg | gaa | aaa | ccc | gag | acc | ttt | tgg | 1251 |
|---|---|---|---|---|---|---|---|---|---|---|---|---|---|---|---|---|
| Ser | Met | Gly | Arg | Asn | Pro | Leu | Tyr | Trp | Glu | Lys | Pro | Glu | Thr | Phe | Trp |
| | | | | 400 | | | | | 405 | | | | | 410 | |

| ccc | gaa | agg | ttt | gac | caa | gtc | tcg | agg | gat | ttc | atg | gga | aac | gat | ttc | 1299 |
|---|---|---|---|---|---|---|---|---|---|---|---|---|---|---|---|---|
| Pro | Glu | Arg | Phe | Asp | Gln | Val | Ser | Arg | Asp | Phe | Met | Gly | Asn | Asp | Phe |
| | | | 415 | | | | | 420 | | | | | 425 | | |

| gag | ttc | atc | cca | ttt | gga | gct | gga | aga | aga | atc | tgc | ccc | ggt | ttg | aat | 1347 |
|---|---|---|---|---|---|---|---|---|---|---|---|---|---|---|---|---|
| Glu | Phe | Ile | Pro | Phe | Gly | Ala | Gly | Arg | Arg | Ile | Cys | Pro | Gly | Leu | Asn |
| | | 430 | | | | | 435 | | | | | 440 | | | |

| ttc | ggg | ttg | gca | aat | gtt | gag | gtc | cca | ttg | gca | cag | ctt | ctt | tac | cac | 1395 |
|---|---|---|---|---|---|---|---|---|---|---|---|---|---|---|---|---|
| Phe | Gly | Leu | Ala | Asn | Val | Glu | Val | Pro | Leu | Ala | Gln | Leu | Leu | Tyr | His |
| | 445 | | | | | 450 | | | | | 455 | | | | |

| ttc | gac | tgg | aag | ttg | gcg | gaa | gga | atg | aac | cct | tcc | gat | atg | gac | atg | 1443 |
|---|---|---|---|---|---|---|---|---|---|---|---|---|---|---|---|---|
| Phe | Asp | Trp | Lys | Leu | Ala | Glu | Gly | Met | Asn | Pro | Ser | Asp | Met | Asp | Met |
| 460 | | | | | 465 | | | | | 470 | | | | | 475 |

| tct | gag | gca | gaa | ggc | ctt | acc | gga | ata | aga | aag | aac | aat | ctt | cta | ctc | 1491 |
|---|---|---|---|---|---|---|---|---|---|---|---|---|---|---|---|---|
| Ser | Glu | Ala | Glu | Gly | Leu | Thr | Gly | Ile | Arg | Lys | Asn | Asn | Leu | Leu | Leu |
| | | | | 480 | | | | | 485 | | | | | 490 | |

| gtt | ccc | aca | ccc | tac | gat | cct | tcc | tca | tgatcaatta | atactcttta | | | | | | 1538 |
|---|---|---|---|---|---|---|---|---|---|---|---|---|---|---|---|---|
| Val | Pro | Thr | Pro | Tyr | Asp | Pro | Ser | Ser | | | | | | | |
| | | 495 | | | | | 500 | | | | | | | | | atttgctcct tgaataaag agtgcatata catatatgat atatacacat acacacacat    1598 atactatata tgtatatgta gctttgggct atgaatatag aaattatgta aaaaaaataa    1658 aaaggaa    1665

<210> SEQ ID NO 70
<211> LENGTH: 500
<212> TYPE: PRT
<213> ORGANISM: Artificial Sequence

<400> SEQUENCE: 70

Met Glu Leu Gln Ile Ser Ser Ala Ile Ile Ile Leu Val Val Thr Tyr
1               5                   10                  15

Thr Ile Ser Leu Leu Ile Ile Lys Gln Trp Arg Lys Pro Lys Pro Gln
            20                  25                  30

Glu Asn Leu Pro Pro Gly Pro Pro Lys Leu Pro Leu Ile Gly His Leu
        35                  40                  45

```
His Leu Leu Trp Gly Lys Leu Pro Gln His Ala Leu Ser Val Ala
         50                  55                  60

Lys Gln Tyr Gly Pro Val Ala His Val Gln Leu Gly Glu Val Phe Ser
 65                  70                  75                  80

Val Val Leu Ser Ser Arg Glu Ala Thr Lys Glu Ala Met Lys Leu Val
                 85                  90                  95

Asp Pro Ala Cys Ala Asp Arg Phe Glu Ser Ile Gly Thr Lys Ile Met
            100                 105                 110

Trp Tyr Asp Asn Asp Asp Ile Ile Phe Ser Pro Tyr Ser Val His Trp
            115                 120                 125

Arg Gln Met Arg Lys Ile Cys Val Ser Glu Leu Leu Ser Ala Arg Asn
            130                 135                 140

Val Arg Ser Phe Gly Phe Ile Arg Gln Asp Glu Val Ser Arg Leu Leu
145                 150                 155                 160

Gly His Leu Arg Ser Ser Ala Ala Ala Gly Glu Ala Val Asp Leu Thr
                165                 170                 175

Glu Arg Ile Ala Thr Leu Thr Cys Ser Ile Ile Cys Arg Ala Ala Phe
            180                 185                 190

Gly Ser Val Ile Arg Asp His Glu Glu Leu Val Glu Leu Val Lys Asp
            195                 200                 205

Ala Leu Ser Met Ala Ser Gly Phe Glu Leu Ala Asp Met Phe Pro Ser
    210                 215                 220

Ser Lys Leu Leu Asn Leu Leu Cys Trp Asn Lys Ser Lys Leu Trp Arg
225                 230                 235                 240

Met Arg Arg Arg Val Asp Ala Ile Leu Glu Ala Ile Val Asp Glu His
                245                 250                 255

Lys Leu Lys Lys Ser Gly Glu Phe Gly Gly Glu Asp Ile Ile Asp Val
            260                 265                 270

Leu Phe Arg Met Gln Lys Asp Ser Gln Ile Lys Val Pro Ile Thr Thr
            275                 280                 285

Asn Ala Ile Lys Ala Phe Ile Phe Asp Thr Phe Ser Ala Gly Thr Glu
    290                 295                 300

Thr Ser Ser Thr Thr Thr Leu Trp Val Met Ala Glu Leu Met Arg Asn
305                 310                 315                 320

Pro Glu Val Met Ala Lys Ala Gln Ala Glu Val Arg Ala Ala Leu Lys
                325                 330                 335

Gly Lys Thr Asp Trp Asp Val Asp Val Gln Glu Leu Lys Tyr Met
            340                 345                 350

Lys Ser Val Val Lys Glu Thr Met Arg Met His Pro Pro Ile Pro Leu
            355                 360                 365

Ile Pro Arg Ser Cys Arg Glu Glu Cys Glu Val Asn Gly Tyr Thr Ile
    370                 375                 380

Pro Asn Lys Ala Arg Ile Met Ile Asn Val Trp Ser Met Gly Arg Asn
385                 390                 395                 400

Pro Leu Tyr Trp Glu Lys Pro Glu Thr Phe Trp Pro Glu Arg Phe Asp
                405                 410                 415

Gln Val Ser Arg Asp Phe Met Gly Asn Asp Phe Glu Phe Ile Pro Phe
            420                 425                 430

Gly Ala Gly Arg Arg Ile Cys Pro Gly Leu Asn Phe Gly Leu Ala Asn
            435                 440                 445

Val Glu Val Pro Leu Ala Gln Leu Leu Tyr His Phe Asp Trp Lys Leu
    450                 455                 460

Ala Glu Gly Met Asn Pro Ser Asp Met Asp Met Ser Glu Ala Glu Gly
```

-continued

```
                465                 470                 475                 480
            Leu Thr Gly Ile Arg Lys Asn Asn Leu Leu Leu Val Pro Thr Pro Tyr
                                485                 490                 495

Asp Pro Ser Ser
                        500
```